(12) United States Patent
Ryu et al.

(10) Patent No.: US 12,145,914 B2
(45) Date of Patent: *Nov. 19, 2024

(54) COMPOUND HAVING OXADIAZOLE AND PHARMACEUTICAL COMPOSITION CONTAINING THE SAME

(71) Applicant: SK BIOPHARMACEUTICALS CO., LTD., Gyeonggi-do (KR)

(72) Inventors: Choon Ho Ryu, Gyeonggi-do (KR); Min Soo Han, Gyeonggi-do (KR); Yeo Jin Yoon, Gyeonggi-do (KR); Yu Jin Kim, Gyeonggi-do (KR); Ka Eun Lee, Gyeonggi-do (KR); Ju Young Lee, Gyeonggi-do (KR); Myung Jin Jung, Gyeonggi-do (KR); Eun Hee Baek, Gyeonggi-do (KR); Yu Jin Shin, Gyeonggi-do (KR); Eun Ju Choi, Gyeonggi-do (KR); Young Soon Kang, Gyeonggi-do (KR); Yong Soo Kim, Gyeonggi-do (KR); Yea Mi Song, Gyeonggi-do (KR); Jin Sung Kim, Gyeonggi-do (KR); Hee Jeong Lim, Gyeonggi-do (KR)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/155,924

(22) Filed: Jan. 18, 2023

(65) Prior Publication Data

US 2023/0150955 A1 May 18, 2023

Related U.S. Application Data

(63) Continuation of application No. 17/327,928, filed on May 24, 2021, now Pat. No. 11,603,358, which is a continuation of application No. 16/613,659, filed as application No. PCT/KR2019/012257 on Sep. 20, 2019, now Pat. No. 11,053,208.

(30) Foreign Application Priority Data

Sep. 21, 2018 (KR) .................. 10-2018-0113956

(51) Int. Cl.
  *C07D 271/10* (2006.01)
  *A61K 31/4245* (2006.01)
  *A61P 25/08* (2006.01)

(52) U.S. Cl.
  CPC ........ *C07D 271/10* (2013.01); *A61K 31/4245* (2013.01); *A61P 25/08* (2018.01)

(58) Field of Classification Search
  CPC .... C07D 271/10; A61P 25/08; A61K 31/4245
  See application file for complete search history.

(56) References Cited

U.S. PATENT DOCUMENTS 7,598,279 B2  10/2009  Choi et al.

FOREIGN PATENT DOCUMENTS

| EA | 022458 B1 | 1/2016 |
| EP | 0021121 B1 | 5/1983 |
| EP | 0162036 B1 | 8/1989 |
| RU | 2470917 C2 | 12/2012 |
| WO | WO-2003006467 A1 | 1/2003 |
| WO | WO-2009/099080 A1 | 8/2009 |
| WO | WO-2011/081205 A1 | 7/2011 |
| WO | WO-2017/060488 A1 | 4/2017 |

OTHER PUBLICATIONS

Extended European Search Report from corresponding European Patent Application No. 19863530.2, dated May 18, 2022.
Office Action (Non-Final) from corresponding U.S. Appl. No. 17/327,928, dated Jul. 5, 2022.
Notice of Allowance from corresponding U.S. Appl. No. 17/327,928, dated Nov. 23, 2022.

*Primary Examiner* — Kamal A Saeed
(74) *Attorney, Agent, or Firm* — Harness, Dickey & Pierce, P.L.C.

(57) ABSTRACT

Disclosed are oxadiazole compounds and pharmaceutically acceptable salts thereof. The compounds and pharmaceutically acceptable salts thereof are specifically suitable for the treatment of neurological diseases such as epilepsy.

17 Claims, No Drawings

COMPOUND HAVING OXADIAZOLE AND PHARMACEUTICAL COMPOSITION CONTAINING THE SAME

CROSS-REFERENCE TO RELATED APPLICATIONS

This application is a continuation of U.S. application Ser. No. 17/327,928, filed on May 24, 2021 which is a continuation of U.S. application Ser. No. 16/613,659, filed on 14 Nov. 2019, which is a national phase entry of PCT Application No. PCT/KR2019/012257, filed on 20 Sep. 2019, which claims the benefit and priority to Korean Patent Application No. 10-2018-0113956, filed on 21 Sep. 2018. The entire disclosures of the applications identified in this paragraph are incorporated herein by references.

FIELD

The present invention relates to a novel compound having oxadiazole, which is useful as an antiepileptic drug for the prevention or treatment of epilepsy, a preparation method therefor, a pharmaceutical composition comprising the same, and use thereof as a medicament.

BACKGROUND

Epilepsy is a disease in which epileptic seizures are repeated and continued without specific reasons, and causes brain damage and physical/mental disorders when it becomes chronic. As a result, epilepsy is a fatal disease that gives a great social and economic burden as well as degrading the quality of life. Epilepsy varies depending on its cause or the region in the cerebrum where changes occur, and shows various symptoms from a simple and repetitive body movement which looks meaningless at first glance, to generalized seizures and loss of consciousness. In most cases, the expression of symptoms cannot be predicted because symptoms suddenly appear. The mechanism of an occurrence of epilepsy is known to be caused by an abnormality and an excitation of the cerebral cortex ultimately, and it has been reported that a disease causing lesions in the cerebral is likely to cause seizures as well. However, idiopathic epilepsy—of which the actual cause is not accurately known—occupies 60 to 70%, and congenital diseases, infections, tumors, stroke, degenerative diseases, head damage, and the like, are known as other causes. The prevalence rate of patients with epilepsy is 0.5% of the population (1 per every 200 people), and the World Health Organization (WHO) estimates that there are more than 50 million patients with epilepsy worldwide.

In principle, epilepsy treatment using a drug is preferentially performed, and surgical treatment therapy may be used in the case of refractory epilepsy having no response to a drug. An epilepsy therapeutic agent is a drug that directly acts on the brain, and a drug is differently selected according to the type of seizures. The drugs mostly used are about 10 drugs such as carbamazepine, phenytoin, valproic acid, phenobarbital, topiramate, levetiracetam and the like, and various novel medicines have been developed since 1990. However, although appropriate drugs and appropriate doses have been selected, the proportion of refractory patients whose symptoms are lasting several times a week, reaches 30 to 40% of the total epilepsy patients, and since levetiracetam of UCB which is currently used as a gold standard-reaches only 40 to 58% of the treatment rate of refractory patients, significant improvement in terms of efficacy is required.

In this regard, European Patent No. 0162036 B1 describes the compound (S)-α-ethyl-2-oxo-1-pyrrolidine acetamide which is well known under the generic name, levetiracetam. In addition, International Publication No. WO 2003/006467 discloses a sulfamate derivative useful for epilepsy therapeutic agents, and a representative compound is well known under the generic name, topiramate. European Patent No. 0021121 B1 discloses a 1, 2, 4-triazine derivative useful for epilepsy therapeutic agents, and a representative compound is well known under the generic name, lamotrigine. Most of the existing epilepsy therapeutic agents were developed based on efficacy in the epilepsy animal model, not in the novel drug discovery based on drug targets.

PRIOR ART DOCUMENTS

Patent Documents (Patent document 1) European Patent No. 0162036 B1
(Patent document 2) International Publication No. WO 2003/006467
(Patent document 3) European Patent No. 0021121 B1

SUMMARY

Technical Problem

An object of the present invention is to provide a novel compound represented by Chemical Formula 1, or an optical isomer, a stereoisomer or a pharmaceutically acceptable salt thereof.

Another object of the present invention is to provide a method for preparing a novel compound represented by Chemical Formula 1, or an optical isomer, a stereoisomer or a pharmaceutically acceptable salt thereof.

Still another object of the present invention is to provide a pharmaceutical composition for the prevention or treatment of epilepsy comprising the above compound, optical isomer, stereoisomer, or pharmaceutically acceptable salt thereof, and a method of preparing the same.

Still another object of the present invention is to provide a method for treating epilepsy of a subject by the use of the above compound or optical isomer, stereoisomer or pharmaceutically acceptable salt thereof.

Technical Solution

To achieve the above object, the present invention provides a compound represented by the following Chemical Formula 1, or an optical isomer, a stereoisomer or a pharmaceutically acceptable salt thereof:

[Chemical Formula 1]

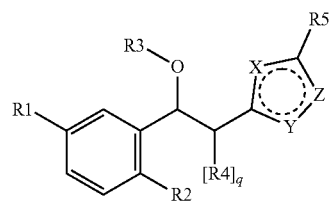

wherein
R1 is selected from the group consisting of the following formulas:

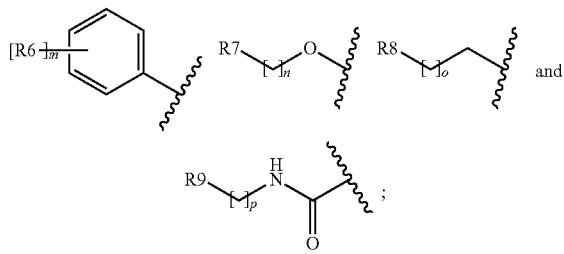

R2 is hydrogen, halo, hydroxy, alkyl, haloalkyl, hydroxyalkyl, alkoxyalkyl, carbamoyloxy, alkoxy, alkylthio, haloalkoxy, or hydroxyalkoxy;

R3 is hydrogen, alkyl, cycloalkyl, haloalkyl, hydroxyalkyl, alkoxyalkyl, carbamoyl, alkylcarbamoyl, dialkylcarbamoyl, carbonyl, or alkylcarbonyl;

R4 is hydrogen, halo, hydroxy, alkyl, haloalkyl, hydroxyalkyl, alkoxyalkyl, carbamoyl, alkylcarbamoyl, or dialkylcarbamoyl;

R5 is hydrogen, halo, hydroxy, alkyl, haloalkyl, hydroxyalkyl, alkoxyalkyl, carbamoyl, alkylcarbamoyl, or dialkylcarbamoyl;

R6, R7, R8 and R9 are each independently hydrogen, halo, alkyl, haloalkyl, hydroxyalkyl, alkoxyalkyl, carbamoyloxyalkyl, alkyl-C(O)O-alkyl, alkoxy, alkylthio, haloalkoxy, hydroxyalkoxy, alkoxy-alkoxy, carbamoyloxyalkoxy, alkyl-C(O)O-alkoxy, amino, dialkylamino, carbonylamino, alkylcarbonylamino, haloalkyl-carbonylamino, or heterocycloalkyl having 1 to 3 nitrogen (N) atoms;

X, Y and Z are each independently selected from the group consisting of nitrogen (N) and oxygen (O), wherein at least one of X, Y and Z is oxygen (O);

m is an integer of 0 to 3;

n, o, and p are each independently an integer of 0 to 5; and q is an integer of 0 to 2.

The compound of Formula 1 according to the present invention may form a pharmaceutically acceptable salt. The pharmaceutically acceptable salts include acid or base addition salts and their stereochemical isomers form. The salt may include any salt that maintains the activity of a parent compound in a subject to be administered and does not cause any undesirable effect, but is not limited thereto. The salts include inorganic salts and organic salts, and may be acid addition salts—for example, acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzenesulfonic acid, benzoic acid, stearic acid, ethanesulfonic acid, lactic acid, bicarbonic acid, bisulfuric acid, bitartaric acid, oxalic acid, butylic acid, calcium edatate, camsylic acid, carbonic acid, chlorobenzoic acid, citric acid, edetic acid, toluenesulfonic acid, edicylinic acid, ecylinic acid, fumaric acid, gluceptic acid, pamoic acid, gluconic acid, glycollarsanylic acid, methyl nitrate, polygalacturonic acid, hexyllisorcynonic acid, malonic acid, hydrabamic acid, hydrochlorinic acid, hydroiodic acid, hydroxynaphtholic acid, isethionic acid, lactobionic acid, mandelic acid, estolinic acid, mucic acid, naphthenic acid, muconic acid, p-nitromethanesulfonic acid, hexamic acid, pantothenic acid, monohydrogen phosphoric acid, dihydrogen phosphoric acid, salicylic acid, sulfamine acid, sulfanilic acid, methanesulfonic acid or theoclic acid. In addition, examples of basic salts include alkali and alkaline earth metal salts such as ammonium salts, lithium salts, sodium salts, potassium salts, magnesium salts, and calcium salts, salts having organic bases such as benzathine, N-methyl-D-glucamine, and hydrabamine salts, and salts having amino acids such as arginine and lysine. In addition, the salt form may be converted into a free form by treatment with an appropriate base or acid. As used herein, the term "additional salt" may be taken to include solvates obtainable from any of the compound represented by Chemical Formula 1 and salts thereof. Examples of these solvates are hydrates or alcoholates. The compound of Chemical Formula 1 according to the present invention may be converted into salt thereof by a conventional method.

Meanwhile, since the compounds according to the present invention may have an asymmetric carbon center and an asymmetric axis or an asymmetric plane, they may exist as substantially pure enantiomers, such as R and S enantiomers, as well as all optical and stereoisomeric forms including mixture racemates, and all isomers and compounds thereof are within the scope of the present invention. With respect to a pure enantiomer, the enantiomeric excess of such enantiomer and pharmaceutically acceptable salt thereof represented by Chemical Formula 1 comprising oxadiazole may be preferably 60% ee or more, more preferably 95% ee ore more, and most preferably 98% ee or more.

The term "ee" refers to an enantiomeric excess. For example, one enantiomer in a particular compound is present as a mixture of enantiomers in the compound in a larger amount than the other enantiomers. Enantiomerically enriched forms may include enantiomeric compounds of a particular compound in which a single enantiomeric concentration in the enantiomeric mixture of the particular compound is at least 50%, more typically at least 60%, 70%, 80%, or 90%, or more (e.g., >95%, >97%, >98%, >99%, >99.5%) with respect to other enantiomers of the compound.

Herein, unless stated otherwise, the compound represented by Chemical Formula 1 is used as a meaning including all of compound represented by Chemical Formula 1, an optical isomer, a stereo isomer and a pharmaceutically acceptable salt thereof.

In defining the compound of Chemical Formula 1 through the present specification, the following concepts are used with respect to substituents.

As used herein, the term "halo," either alone or in combination with additional terms (for example, haloalkyl), refers to a radical of fluorine (F), chlorine (Cl), bromine (Br) or iodine (I).

As used herein, the term "alkyl," either alone or in combination with additional terms (for example, haloalkyl), refers to a radical of a saturated or unsaturated aliphatic hydrocarbon group having 1 to 10, preferably from 1 to 5 carbon atoms of a linear or branched chain, and may include a single bond, a double bond or a triple bond. For example, the alkyl may include such as methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, and 1, 2-dimethylpropyl, but is not limited thereto.

As used herein, the term "cycloalkyl" is a partially or fully saturated single or fused cyclic hydrocarbon, which may be C3-C12-cycloalkyl, and C3-C6-cycloalkyl is preferred, including, but not limited to, for example, cyclopropyl, cyclobutyl, cyclopentyl, cyclohexyl, cyclohexanyl and the like.

As used herein, the term "alkoxy" refers to alkyloxy having 1 to 10, preferably 1 to 5 carbon atoms unless stated otherwise.

As used herein, the term "heterocycloalkyl" refers to a partially or fully saturated hydrocarbon including 1 to 3 nitrogen (N) atoms as ring members, and 3- to 8-membered, or 5- to 8-membered heterocycle is preferred. For example, aziridinyl, azetidinyl, pyrrolidinyl, piperidinyl, imidazolinyl, piperazinyl and the like are included but are not limited thereto.

The alkyl, cycloalkyl, alkoxy and heterocycle and the like may be optionally substituted, for example, with one or more substituents selected from the following groups: hydroxy, halo, alkyl, alkoxy, haloalkyl and haloalkoxy.

As used herein, the term "epilepsy" refers to a disease group in which the epilepsy seizures occur repeatedly and become chronically even though there is no cause factor capable of causing the epilepsy seizures. Epilepsy may be classified into focal onset seizure, generalized onset seizure, and unknown onset seizure. In addition, epilepsy may be specifically focal onset seizure with or without a secondary generalized seizure.

The hydrogen atoms of Chemical Formula 1 of the present invention may be selected from hydrogen, deuterium, and tritium.

According to another embodiment, in Chemical Formula 1,

R1 is selected from the group consisting of following formulas:

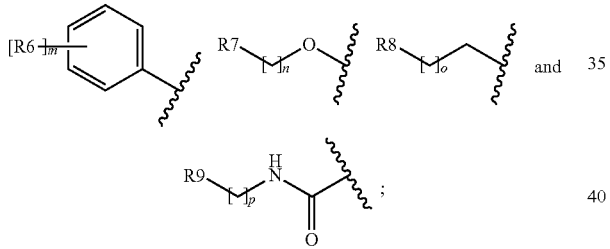

R2 is hydrogen, halo, hydroxy, $C_1$-$C_5$ alkyl, halo-$C_1$-$C_5$ alkyl, hydroxy-$C_1$-$C_5$ alkyl, $C_1$-$C_5$ alkoxy-$C_1$-$C_5$ alkyl, carbamoyloxy, $C_1$-$C_5$ alkoxy, $C_1$-$C_5$ alkylthio, halo-$C_1$-$C_5$ alkoxy, or hydroxy-$C_1$-$C_5$ alkoxy;

R3 is hydrogen, $C_1$-$C_5$ alkyl, $C_3$-$C_6$ cycloalkyl, halo-$C_1$-$C_5$ alkyl, hydroxy-$C_1$-$C_5$ alkyl, $C_1$-$C_5$ alkoxy-$C_1$-$C_5$ alkyl, carbamoyl, $C_1$-$C_5$ alkyl-carbamoyl, di($C_1$-$C_5$ alkyl)-carbamoyl, carbonyl, or $C_1$-$C_5$ alkyl-carbonyl;

R4 is hydrogen, halo, hydroxy, $C_1$-$C_5$ alkyl, halo-$C_1$-$C_5$ alkyl, hydroxy-$C_1$-$C_5$ alkyl, $C_1$-$C_5$ alkoxy-$C_1$-$C_5$ alkyl, carbamoyl, $C_1$-$C_5$ alkyl-carbamoyl, or di($C_1$-$C_5$ alkyl)-carbamoyl;

R5 is hydrogen, halo, hydroxy, $C_1$-$C_5$ alkyl, halo-$C_1$-$C_5$ alkyl, hydroxy-$C_1$-$C_5$ alkyl, $C_1$-$C_5$ alkoxy-$C_1$-$C_5$ alkyl, carbamoyl, $C_1$-$C_5$ alkyl-carbamoyl, or di($C_1$-$C_5$ alkyl)-carbamoyl;

R6, R7, R8 and R9 are each independently hydrogen, halo, $C_1$-$C_5$ alkyl, halo-$C_1$-$C_5$ alkyl, hydroxy-$C_1$-$C_5$ alkyl, $C_1$-$C_5$ alkoxy-$C_1$-$C_5$ alkyl, carbamoyloxy-$C_1$-$C_5$ alkyl, $C_1$-$C_5$ alkyl-C(O)O—$C_1$-$C_5$ alkyl, $C_1$-$C_5$ alkoxy, $C_1$-$C_5$ alkylthio, halo-$C_1$-$C_5$ alkoxy, hydroxy-$C_1$-$C_5$ alkoxy, $C_1$-$C_5$ alkoxy-$C_1$-$C_5$ alkoxy, carbamoyloxy-$C_1$-$C_5$-alkoxy, $C_1$-$C_5$ alkyl-C(O)O—$C_1$-$C_5$ alkoxy, amino, di($C_1$-$C_5$ alkyl)amino, carbonylamino, $C_1$-$C_5$ alkyl-carbonylamino, halo-$C_1$-$C_5$ alkyl-carbonylamino, or a 3- to 8-membered heterocycloalkyl having 1 to 3 nitrogen (N) atoms;

X, Y, Z are each independently selected from the group consisting of nitrogen (N) and oxygen (O), wherein at least one of X, Y or Z is oxygen (O);

m is an integer of 0 to 3;

n, o, and p are each independently an integer of 0 to 5; and q is an integer of 0 to 2.

According to still another embodiment, in Chemical Formula 1,

R1 is selected from the group consisting of following formulas:

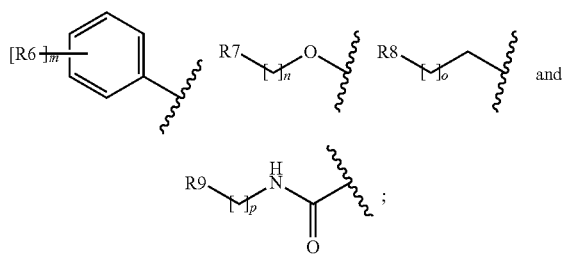

R2 is hydrogen, halo, alkyl, haloalkyl, hydroxyalkyl, alkoxyalkyl, alkoxy, alkylthio, haloalkoxy, or hydroxyalkoxy;

R3 is hydrogen, alkyl, cycloalkyl, haloalkyl, alkoxyalkyl, carbamoyl, alkylcarbamoyl, dialkylcarbamoyl, carbonyl, or alkylcarbonyl;

R4 is hydrogen, halo, alkyl, haloalkyl, alkoxyalkyl, carbamoyl, alkylcarbamoyl, or dialkylcarbamoyl;

R5 is hydrogen, halo, alkyl, haloalkyl, alkoxyalkyl, carbamoyl, alkylcarbamoyl, or dialkylcarbamoyl;

R6, R7, R8 and R9 are each independently hydrogen, halo, alkyl, haloalkyl, alkoxyalkyl, carbamoyloxyalkyl, alkyl-C(O)O-alkyl, alkoxy, alkylthio, haloalkoxy, alkoxy-alkoxy, carbamoyloxy-alkoxy, alkyl-C(O)O-alkoxy, amino, dialkylamino, carbonylamino, alkylcarbonylamino, haloalkyl-carbonylamino, or heterocycloalkyl having 1 or 2 nitrogen (N) atoms;

X, Y, and Z are each independently selected from the group consisting of nitrogen (N) and oxygen (O), wherein one of X, Y or Z is oxygen (O) and the other two are nitrogen (N);

m is an integer of 0 to 3;

n, o, and p are each independently an integer of 0 to 4; and q is an integer of 0 to 2.

According to still another embodiment, in Chemical Formula 1,

R1 is selected from the group consisting of following formulas:

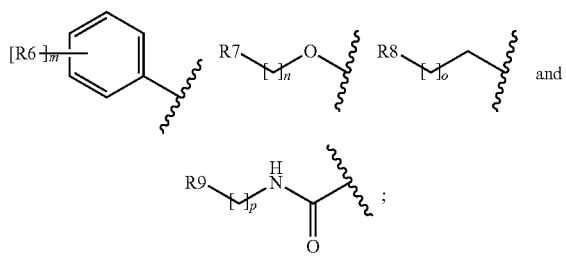

R2 is hydrogen, halo, $C_1$-$C_5$ alkyl, halo-$C_1$-$C_5$ alkyl, hydroxy-$C_1$-$C_5$ alkyl, $C_1$-$C_5$ alkoxy-$C_1$-$C_5$ alkyl, $C_1$-$C_5$ alkoxy, $C_1$-$C_5$ alkylthio, halo-$C_1$-$C_5$ alkoxy, or hydroxy-$C_1$-$C_5$ alkoxy;

R3 is hydrogen, $C_1$-$C_5$ alkyl, $C_3$-$C_6$ cycloalkyl, halo-$C_1$-$C_5$ alkyl, $C_1$-$C_5$ alkoxy-$C_1$-$C_5$ alkyl, carbamoyl, $C_1$-$C_5$ alkyl-carbamoyl, di($C_1$-$C_5$ alkyl)carbamoyl, carbonyl, or $C_1$-$C_5$ alkyl-carbonyl;

R4 is hydrogen, halo, $C_1$-$C_5$ alkyl, halo-$C_1$-$C_5$ alkyl, $C_1$-$C_5$ alkoxy-$C_1$-$C_5$ alkyl, carbamoyl, $C_1$-$C_5$ alkyl-carbamoyl, or di($C_1$-$C_5$ alkyl)-carbamoyl;

R5 is hydrogen, halo, $C_1$-$C_5$ alkyl, halo-$C_1$-$C_5$ alkyl, $C_1$-$C_5$ alkoxy-$C_1$-$C_5$ alkyl, carbamoyl, $C_1$-$C_5$ alkyl-carbamoyl, or di($C_1$-$C_5$ alkyl)-carbamoyl;

R6, R7, R8 and R9 are each independently hydrogen, halo, $C_1$-$C_5$ alkyl, halo-$C_1$-$C_5$ alkyl, $C_1$-$C_5$ alkoxy-$C_1$-$C_5$ alkyl, carbamoyloxy-$C_1$-$C_5$ alkyl, $C_1$-$C_5$ alkyl-C(O)O—$C_1$-$C_5$ alkyl, $C_1$-$C_5$ alkoxy, $C_1$-$C_5$ alkylthio, halo-$C_1$-$C_5$ alkoxy, $C_1$-$C_5$ alkoxy-$C_1$-$C_5$ alkoxy, carbamoyloxy-$C_1$-$C_5$ alkoxy, $C_1$-$C_5$ alkyl-C(O)O—$C_1$-$C_5$ alkoxy, amino, di($C_1$-$C_5$ alkyl)amino, carbonylamino, $C_1$-$C_5$ alkyl-carbonylamino, halo-$C_1$-$C_5$ alkyl-carbonylamino, or a 5- to 8-membered heterocycloalkyl having one or two nitrogen (N) atoms;

X, Y, Z are each independently selected from the group consisting of nitrogen (N) and oxygen (O), wherein one of X, Y or Z is oxygen (O) and the other two are nitrogen (N);

m is an integer of 0 to 3;

n, o, and p are each independently an integer of 0 to 4; and q is an integer of 0 to 2.

According to still another embodiment, in Chemical Formula 1,

R1 is selected from the group consisting of the following formulas:

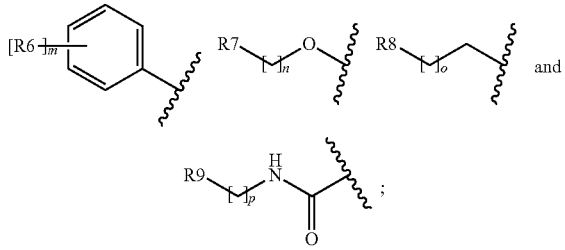

R2 is hydrogen, halo, alkyl, haloalkyl, alkoxyalkyl, alkoxy, or alkylthio;

R3 is hydrogen, alkyl, cycloalkyl, haloalkyl, carbamoyl, alkylcarbamoyl, dialkylcarbamoyl, or carbonyl;

R4 is hydrogen, halo, alkyl, haloalkyl, or alkoxyalkyl;

R5 is hydrogen, halo, alkyl, haloalkyl, or alkoxyalkyl;

R6, R7, R8 and R9 are each independently hydrogen, halo, alkyl, haloalkyl, alkoxyalkyl, alkoxy, alkylthio, haloalkoxy, amino, dialkylamino, alkylcarbonylamino, haloalkyl-carbonylamino, or heterocycloalkyl having one or two nitrogen (N) atoms;

X, Y, Z are each independently selected from the group consisting of nitrogen (N) and oxygen (O), where one of X, Y or Z is oxygen (O) and the other two is nitrogen (N);

m is an integer of 1 to 3;

n, o, and p are each independently an integer of 0 to 4; and q is an integer of 0 to 2.

According to still another embodiment of the present invention, in Chemical Formula 1, R1 is selected from the group consisting of the following formulas;

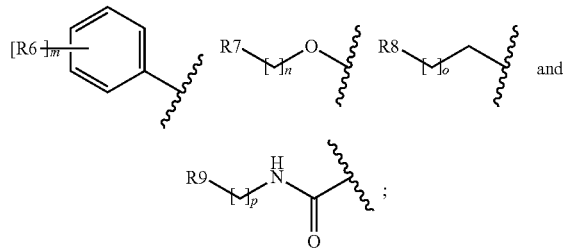

R2 is hydrogen, halo, $C_1$-$C_5$ alkyl, halo-$C_1$-$C_5$ alkyl, $C_1$-$C_5$ alkoxy-$C_1$-$C_5$ alkyl, $C_1$-$C_5$ alkoxy, or $C_1$-$C_5$ alkylthio;

R3 is hydrogen, $C_1$-$C_5$ alkyl, $C_3$-$C_6$ cycloalkyl, halo-$C_1$-$C_5$ alkyl, carbamoyl, $C_1$-$C_5$ alkyl-carbamoyl, di($C_1$-$C_5$ alkyl)carbamoyl, or carbonyl;

R4 is hydrogen, halo, $C_1$-$C_5$ alkyl, halo-$C_1$-$C_5$ alkyl, or $C_1$-$C_5$ alkoxy-$C_1$-$C_5$ alkyl;

R5 is hydrogen, halo, $C_1$-$C_5$ alkyl, halo-$C_1$-$C_5$ alkyl, or $C_1$-$C_5$ alkoxy-$C_1$-$C_5$ alkyl;

R6, R7, R8 and R9 are each independently hydrogen, halo, $C_1$-$C_5$ alkyl, halo-$C_1$-$C_5$ alkyl, $C_1$-$C_5$ alkoxy-$C_1$-$C_5$ alkyl, $C_1$-$C_5$ alkoxy, $C_1$-$C_5$ alkylthio, halo-$C_1$-$C_5$ alkoxy, amino, di($C_1$-$C_5$ alkyl)amino, $C_1$-$C_5$ alkyl-carbonylamino, halo-$C_1$-$C_5$ alkyl-carbonylamino, or a 5- to 8-membered heterocycloalkyl having one or two nitrogen (N) atoms;

X, Y, and Z are each independently selected from the group consisting of nitrogen (N) and oxygen (O), wherein one of X, Y or Z is oxygen (O) and the other two are nitrogen (N);

m is an integer of 1 to 3;

n, o, and p are each independently an integer of 0 to 4; and q is an integer from 0 to 2.

According to still another embodiment, in Chemical Formula 1, R1 is selected from the group consisting of following formulas:

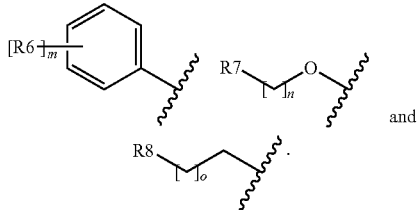

According to still another embodiment, in Chemical Formula 1, R1 is represented by following formula:

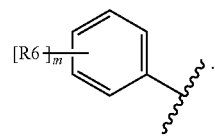

According to still another embodiment of the present invention, in Chemical Formula 1, R6, R7, R8 and R9 are each independently hydrogen, halo, alkyl, haloalkyl, alkoxy, haloalkoxy, dialkylamino, or heterocycloalkyl having 1 to 3 nitrogen (N) atoms.

According to still another embodiment of the present invention, in Chemical Formula 1, R6, R7, R8 and R9 are each independently hydrogen, halo, $C_1$-$C_5$ alkyl, halo-$C_1$-$C_5$ alkyl, $C_1$-$C_5$ alkoxy, halo-$C_1$-$C_5$ alkoxy, di($C_1$-$C_5$ alkyl) amino or 3- to 8-membered heterocycloalkyl having 1 to 3 nitrogen (N) atoms.

According to still another embodiment of the present invention, in Chemical Formula 1, R6, R7 and R8 are each independently halo, alkyl, haloalkyl, alkoxy, or haloalkoxy.

According to still another embodiment of the present invention, in Chemical Formula 1, R6, R7 and R8 are each independently halo, $C_1$-$C_5$ alkyl, halo-$C_1$-$C_5$ alkyl, $C_1$-$C_5$ alkoxy, or halo-$C_1$-$C_5$ alkoxy.

According to still another embodiment of the present invention, in Chemical Formula 1, R6 is halo, haloalkyl, alkoxy, or haloalkoxy.

According to still another embodiment of the present invention, in Chemical Formula 1, R6 is halo, halo-$C_1$-$C_5$ alkyl, $C_1$-$C_5$ alkoxy, or halo-$C_1$-$C_5$ alkoxy.

According to still another embodiment of the present invention, in Chemical Formula 1,
R2 is hydrogen, halo, alkyl or alkoxy;
R3 is hydrogen, alkyl or carbamoyl;
R4 is hydrogen, halo or alkyl; and
R5 is hydrogen or alkyl.

According to still another embodiment of the present invention, in Chemical Formula 1,
R2 is hydrogen, halo, $C_1$-$C_5$ alkyl or $C_1$-$C_5$ alkoxy;
R3 is hydrogen, $C_1$-$C_5$ alkyl or carbamoyl;
R4 is hydrogen, halo or $C_1$-$C_5$ alkyl; and
R5 is hydrogen or $C_1$-$C_5$ alkyl.

According to still another embodiment of the present invention, in Chemical Formula 1, X is oxygen (O), and each of Y and Z is nitrogen (N).

According to still another embodiment of the present invention, in Chemical Formula 1,
m is an integer of 1 or 2;
n, o and p are each independently an integer of 1 to 4; and
q is an integer of 0 or 1.

Representative examples of the compound of Chemical Formula 1 according to the present invention may include compounds shown in Table 1, but are not limited thereto.

TABLE 1

| No. | Compound Name |
|-----|---------------|
| 1 | 1-[5-(4-chlorophenyl)-2-fluoro-phenyl]-2-(5-methyl-1,3,4-oxadiazol-2-yl)ethanol |
| 2 | 1-[2-fluoro-5-[4-(trifluoromethyl)phenyl]phenyl]-2-(5-methyl-1,3,4-oxadiazol-2-yl)ethanol |
| 3 | [1-[2-fluoro-5-[4-(trifluoromethyl)phenyl]phenyl]-2-(5-methyl-1,3,4-oxadiazol-2-yl)ethyl] carbamate |
| 4 | [1-[5-(4-chlorophenyl)-2-fluoro-phenyl]-2-(5-methyl-1,3,4-oxadiazol-2-yl)ethyl] carbamate |
| 5 | 1-[2-fluoro-5-[4-(trifluoromethyl)phenyl]phenyl]-2-(1,3,4-oxadiazol-2-yl)ethanol |
| 6 | 2-(5-methyl-1,3,4-oxadiazol-2-yl)-1-[3-[4-(trifluoromethyl)phenyl]phenyl]ethanol |
| 7 | [2-(5-methyl-1,3,4-oxadiazol-2-yl)-1-[3-[4-(trifluoromethyl)phenyl]phenyl]ethyl] carbamate |
| 8 | 2-(5-methyl-1,3,4-oxadiazol-2-yl)-1-[3-(2,2,3,3-tetrafluoropropoxy)phenyl]ethanol |
| 9 | [2-(5-methyl-1,3,4-oxadiazol-2-yl)-1-[3-(2,2,3,3-tetrafluoropropoxy)phenyl]ethyl] carbamate |
| 10 | 1-[2-fluoro-5-(3,3,3-trifluoropropyl)phenyl]-2-(5-methyl-1,3,4-oxadiazol-2-yl)ethanol |
| 11 | [1-[2-fluoro-5-(3,3,3-trifluoropropyl)phenyl]-2-(5-methyl-1,3,4-oxadiazol-2-yl)ethyl] carbamate |
| 12 | 1-[2-fluoro-5-(3,3,3-trifluoropropyl)phenyl]-2-(1,3,4-oxadiazol-2-yl)ethanol |
| 13 | (1R)-2-(5-methyl-1,3,4-oxadiazol-2-yl)-1-[3-[4-(trifluoromethyl)phenyl]phenyl]ethanol |
| 14 | (1S)-2-(5-methyl-1,3,4-oxadiazol-2-yl)-1-[3-[4-(trifluoromethyl)phenyl]phenyl]ethanol |
| 15 | 1-[2-fluoro-5-(4,4,4-trifluorobutoxy)phenyl]-2-(5-methyl-1,3,4-oxadiazol-2-yl)ethanol |
| 16 | [1-[2-fluoro-5-(4,4,4-trifluorobutoxy)phenyl]-2-(5-methyl-1,3,4-oxadiazol-2-yl)ethyl] carbamate |
| 17 | 1-[2-fluoro-5-(2,2,2-trifluoroethoxy)phenyl]-2-(5-methyl-1,3,4-oxadiazol-2-yl)ethanol |
| 18 | [1-[2-fluoro-5-(2,2,2-trifluoroethoxy)phenyl]-2-(5-methyl-1,3,4-oxadiazol-2-yl)ethyl] carbamate |
| 19 | 2-(5-methyl-1,3,4-oxadiazol-2-yl)-1-[3-(4,4,4-trifluorobutoxy)phenyl]ethanol |
| 20 | [2-(5-methyl-1,3,4-oxadiazol-2-yl)-1-[3-(4,4,4-trifluorobutoxy)phenyl]ethyl] carbamate |
| 21 | 1-(5-butoxy-2-fluoro-phenyl)-2-(5-methyl-1,3,4-oxadiazol-2-yl)ethanol |
| 22 | [1-(5-butoxy-2-fluoro-phenyl)-2-(5-methyl-1,3,4-oxadiazol-2-yl)ethyl] carbamate |
| 23 | 1-[2-fluoro-5-(4,4,4-trifluorobutoxy)phenyl]-2-(1,3,4-oxadiazol-2-yl)ethanol |
| 24 | [1-[2-fluoro-5-(4,4,4-trifluorobutoxy)phenyl]-2-(1,3,4-oxadiazol-2-yl)ethyl] carbamate |
| 25 | 1-(2-fluoro-5-propyl-phenyl)-2-(5-methyl-1,3,4-oxadiazol-2-yl)ethanol |
| 26 | 1-(2-fluoro-5-pentyl-phenyl)-2-(5-methyl-1,3,4-oxadiazol-2-yl)ethanol |
| 27 | [1-(2-fluoro-5-propyl-phenyl)-2-(5-methyl-1,3,4-oxadiazol-2-yl)ethyl] carbamate |
| 28 | [1-(2-fluoro-5-pentyl-phenyl)-2-(5-methyl-1,3,4-oxadiazol-2-yl)ethyl] carbamate |
| 29 | 1-[2-fluoro-5-(4,4,4-trifluorobutyl)phenyl]-2-(1,3,4-oxadiazol-2-yl)ethanol |
| 30 | 1-[2-fluoro-5-(5,5,5-trifluoropentyl)phenyl]-2-(1,3,4-oxadiazol-2-yl)ethanol |
| 31 | 1-[2-fluoro-5-(4,4,4-trifluorobutyl)-phenyl]-2-(5-methyl-1,3,4-oxadiazol-2-yl)ethanol |
| 32 | 1-[2-fluoro-5-(5,5,5-trifluoropentyl)-phenyl]-2-(5-methyl-1,3,4-oxadiazol-2-yl)ethanol |
| 33 | [1-[2-fluoro-5-(4,4,4-trifluorobutyl)phenyl]-2-(5-methyl-1,3,4-oxadiazol-2-yl)ethyl] carbamate |
| 34 | [1-[fluoro-5-(5,5,5-trifluoropentyl)phenyl]-2-(5-methyl-1,3,4-oxadiazol-2-yl)ethyl] carbamate |
| 35 | 1-[2-fluoro-5-[3-(1-piperidyl)propoxy]phenyl]-2-(5-methyl-1,3,4-oxadiazol-2-yl)ethanol |
| 36 | 1-[5-[3-(dimethylamino)propoxy]-2-fluoro-phenyl]-2-(5-methyl-1,3,4-oxadiazol-2-yl)ethanol |
| 37 | 4-fluoro-3-[1-hydroxy-2-(5-methyl-1,3,4-oxadiazol-2-yl)ethyl]-N-(3,3,3-trifluoropropyl)benzamide |
| 38 | [1-[2-fluoro-5-(3,3,3-trifluoropropylcarbamoyl)phenyl]-2-(5-methyl-1,3,4-oxadiazol-2-yl)ethyl] carbamate |
| 39 | 1-[2-chloro-5-(4,4,4-trifluorobutoxy)phenyl]-2-(5-methyl-1,3,4-oxadiazol-2-yl)ethanol |
| 40 | [1-[5-[3-(dimethylamino)propoxy]-2-fluoro-phenyl]-2-(5-methyl-1,3,4-oxadiazol-2-yl)ethyl] carbamate |
| 41 | [1-[2-chloro-5-(4,4,4-trifluorobutoxy)phenyl]-2-(5-methyl-1,3,4-oxadiazol-2-yl)ethyl] carbamate |
| 42 | 2-(5-methyl-1,3,4-oxadiazol-2-yl)-1-[2-methyl-5-[4-(trifluoromethyl)phenyl]phenyl]ethanol |
| 43 | 1-[2-methoxy-5-[4-(trifluoromethyl)phenyl]phenyl]-2-(5-methyl-1,3,4-oxadiazol-2-yl)ethanol |
| 44 | [2-(5-methyl-1,3,4-oxadiazol-2-yl)-1-[2-methyl-5-[4-(trifluoromethyl)phenyl]phenyl]ethyl] carbamate |
| 45 | [1-[2-methoxy-5-[4-(trifluoromethyl)phenyl]phenyl]-2-(5-methyl-1,3,4-oxadiazol-2-yl)ethyl] carbamate |
| 46 | 1-[2-methyl-5-[4-(trifluoromethyl)phenyl]phenyl]-2-(1,3,4-oxadiazol-2-yl)ethanol |
| 47 | 1-[2-methoxy-5-[4-(trifluoromethyl)phenyl]phenyl]-2-(1,3,4-oxadiazole-2-yl)ethanol |

TABLE 1-continued

| No. | Compound Name |
|---|---|
| 48 | 1-[2-chloro-5-[4-(trifluoromethyl)phenyl]phenyl]-2-(5-methyl-1,3,4-oxadiazol-2-yl)ethanol |
| 49 | 1-[2-chloro-5-[4-(trifluoromethyl)phenyl]phenyl]-2-(1,3,4-oxadiazol-2-yl)ethanol |
| 50 | [1-[2-chloro-5-[4-(trifluoromethyl)phenyl]phenyl]-2-(5-methyl-1,3,4-oxadiazol-2-yl)ethyl] carbamate |
| 51 | [1-[2-chloro-5-[4-(trifluoromethyl)phenyl]phenyl]-2-(1,3,4-oxadiazol-2-yl)ethyl] carbamate |
| 52 | 2-(1,3,4-oxadiazol-2-yl)-1-[3-[4-(trifluoromethyl)phenyl]phenyl]ethanol |
| 53 | 2-(5-ethyl-1,3,4-oxadiazol-2-yl)-1-[3-[4-(trifluoromethyl)phenyl]phenyl]ethanol |
| 54 | 2-(5-tert-butyl-1,3,4-oxadiazol-2-yl)-1-[3-[4-(trifluoromethyl)phenyl]phenyl]ethanol |
| 55 | [2-(5-methyl-1,3,4-oxadiazol-2-yl)-1-[3-[4-(trifluoromethyl)phenyl]phenyl]ethyl] acetate |
| 56 | 2-[2-methoxy-2-[3-[4-(trifluoromethyl)phenyl]phenyl]ethyl]-5-methyl-1,3,4-oxadiazole |
| 57 | 1-[3-(4-fluorophenyl)phenyl]-2-(5-methyl-1,3,4-oxadiazol-2-yl)ethanol |
| 58 | 1-[3-(3,4-difluorophenyl)phenyl]-2-(5-methyl-1,3,4-oxadiazol-2-yl)ethanol |
| 59 | 2-(5-methyl-1,3,4-oxadiazol-2-yl)-1-[3-[4-(trifluoromethoxy)phenyl]phenyl]ethanol |
| 60 | 1-[3-(2-methoxy-4-(trifluoromethoxy)phenyl)phenyl]-2-(5-methyl-1,3,4-oxadiazol-2-yl)ethanol |
| 61 | 1-[3-(4-chloro-2-(trifluoromethyl)phenyl)phenyl]-2-(5-methyl-1,3,4-oxadiazol-2-yl)ethanol |
| 62 | 1-[3-(4-chloro-2-methoxy-phenyl)phenyl]-2-(5-methyl-1,3,4-oxadiazol-2-yl)ethanol |
| 63 | 1-[3-(2-chlorophenyl)phenyl]-2-(5-methyl-1,3,4-oxadiazol-2-yl)ethanol |
| 64 | 1-[3-(3-chlorophenyl)phenyl]-2-(5-methyl-1,3,4-oxadiazol-2-yl)ethanol |
| 65 | 1-[3-(4-chlorophenyl)phenyl]-2-(5-methyl-1,3,4-oxadiazol-2-yl)ethanol |
| 66 | 2-fluoro-2-(5-methyl-1,3,4-oxadiazol-2-yl)-1-[3-(4,4,4-trifluorobutoxy)phenyl]ethanol |
| 67 | 2-(5-methyl-1,3,4-oxadiazol-2-yl)-1-[3-(4,4,4-trifluorobutoxy)phenyl]propan-1-ol |
| 68 | [1-[3-[2-methoxy-4-(trifluoromethoxy)phenyl]phenyl]-2-(5-methyl-1,3,4-oxadiazol-2-yl)ethyl] carbamate |
| 69 | [1-[3-[4-chloro-2-(trifluoromethyl)phenyl]phenyl]-2-(5-methyl-1,3,4-oxadiazol-2-yl)ethyl] carbamate |
| 70 | [1-[3-(4-chloro-2-methoxy-phenyl)phenyl]-2-(5-methyl-1,3,4-oxadiazol-2-yl)ethyl] carbamate |
| 71 | [1-[3-(3,4-difluorophenyl)phenyl]-2-(5-methyl-1,3,4-oxadiazol-2-yl)ethyl] carbamate |
| 72 | [1-[3-(4-fluorophenyl)phenyl]-2-(5-methyl-1,3,4-oxadiazol-2-yl)ethyl] carbamate |
| 73 | [1-[3-(2-chlorophenyl)phenyl]-2-(5-methyl-1,3,4-oxadiazol-2-yl)ethyl] carbamate |
| 74 | [1-[3-(3-chlorophenyl)phenyl]-2-(5-methyl-1,3,4-oxadiazol-2-yl)ethyl] carbamate |
| 75 | [1-[3-(4-chlorophenyl)phenyl]-2-(5-methyl-1,3,4-oxadiazol-2-yl)ethyl] carbamate |
| 76 | [1-[3-[2,4-bis(trifluoromethyl)phenyl]phenyl]-2-(5-methyl-1,3,4-oxadiazol-2-yl)ethanol |
| 77 | [1-[3-[2,4-bis(trifluoromethyl)phenyl]phenyl]-2-(5-methyl-1,3,4-oxadiazol-2-yl)ethyl] carbamate |
| 78 | [1-[3-[4-(trifluoromethoxy)phenyl]phenyl]-2-(5-methyl-1,3,4-oxadiazol-2-yl)ethyl] carbamate |
| 79 | [2-fluoro-2-(5-methyl-1,3,4-oxadiazol-2-yl)-1-[3-(4,4,4-trifluorobutoxy)phenyl]ethyl] carbamate |
| 80 | [2-(5-methyl-1,3,4-oxadiazol-2-yl)-1-[3-(4,4,4-trifluorobutoxy)phenyl]propyl] carbamate |
| 81 | 2-(3-methyl-1,2,4-oxadiazol-5-yl)-1-[3-[4-(trifluoromethyl)phenyl]phenyl]ethanol |
| 82 | [2-(3-methyl-1,2,4-oxadiazol-5-yl)-1-[3-[4-(trifluoromethyl)phenyl]phenyl]ethyl] carbamate |
| 83 | 2-(5-methyl-1,2,4-oxadiazol-3-yl)-1-[3-[4-(trifluoromethyl)phenyl]phenyl]ethanol |
| 84 | [2-(5-methyl-1,2,4-oxadiazol-5-yl)-1-[3-[4-(trifluoromethyl)phenyl]phenyl]ethyl] carbamate |
| 85 | (1R)-1-[2-fluoro-5-(4,4,4-trifluorobutoxy)phenyl]-2-(5-methyl-1,3,4-oxadiazol-2-yl)ethanol |
| 86 | (1S)-1-[2-fluoro-5-(4,4,4-trifluorobutoxy)phenyl]-2-(5-methyl-1,3,4-oxadiazol-2-yl)ethanol |

Terms and abbreviations used in the present specification have their original meanings unless stated otherwise.

The present invention also provides a method for preparing a compound of Chemical Formula 1. Hereinafter, a method of preparing the compound of Chemical Formula 1 will be described based on an exemplary reaction scheme for better understanding of the present invention. However, it should be construed that those of ordinary skill in the art may prepare the compound of Chemical Formula 1 by various methods using known compounds based on the structure of Chemical Formula 1 or compounds that may be easily prepared therefrom, and be construed that all the methods may be included in the scope of the present invention. That is, the compound of Chemical Formula 1 may be prepared by arbitrarily combining several synthesis methods described in the present specification or disclosed in the prior art, and thus the following description related to the method of preparing the compound of Chemical Formula 1 is merely illustrative, and if necessary, the order of unit operations may be selectively changed, and the scope of the method of preparing the present invention is not limited thereto.

Hereinafter, M refers to a molar concentration, and N refers to a normal concentration. Description of the terms and abbreviations used in the reaction schemes, preparation examples and examples of the present specification are as follows:

LDA: lithium diisopropylamide
TBDMS: tert-butyldimethylsilyl
PPh3: triphenylphosphine

[Reaction Scheme 1]

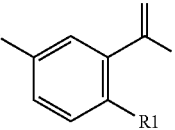

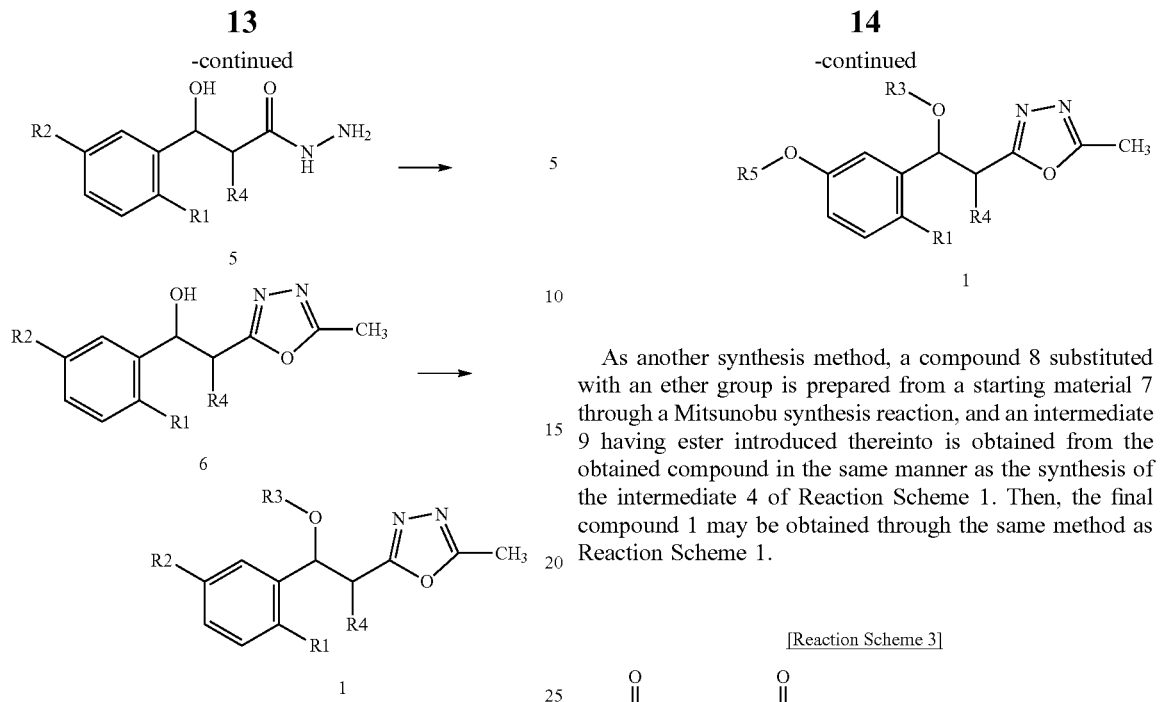

A general synthetic method is to obtain an intermediate 4 in which R2 is introduced from the starting material 2a or 2b through Suzuki coupling synthesis reaction with an intermediate 3 in which ester is introduced. The oxadiazole may be introduced into the intermediate 6 through cyclization reaction using the hydrazide intermediate 5 from the compound, and final compound 1 may be obtained through nucleophilic substitution reaction at the hydroxy group in the final step.

As another synthesis method, a compound 8 substituted with an ether group is prepared from a starting material 7 through a Mitsunobu synthesis reaction, and an intermediate 9 having ester introduced thereinto is obtained from the obtained compound in the same manner as the synthesis of the intermediate 4 of Reaction Scheme 1. Then, the final compound 1 may be obtained through the same method as Reaction Scheme 1.

[Reaction Scheme 3]

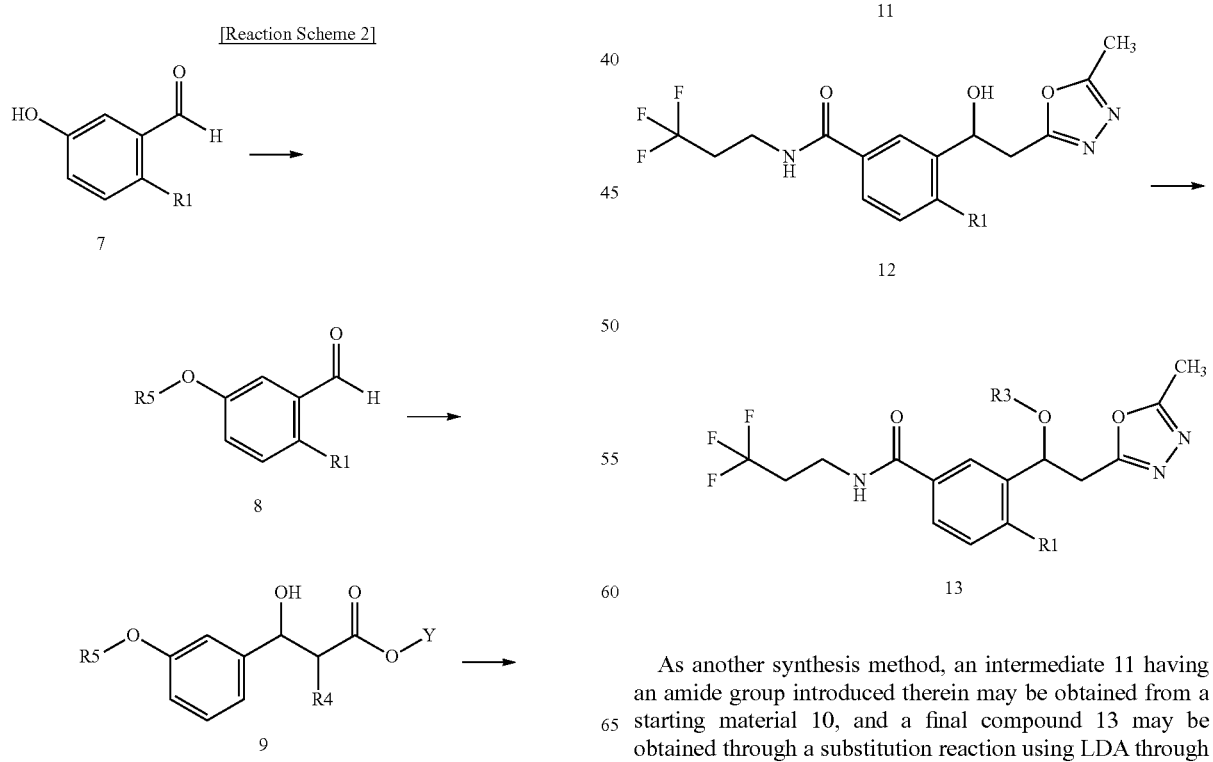

As another synthesis method, an intermediate 11 having an amide group introduced therein may be obtained from a starting material 10, and a final compound 13 may be obtained through a substitution reaction using LDA through an intermediate 12.

[Reaction Scheme 4]

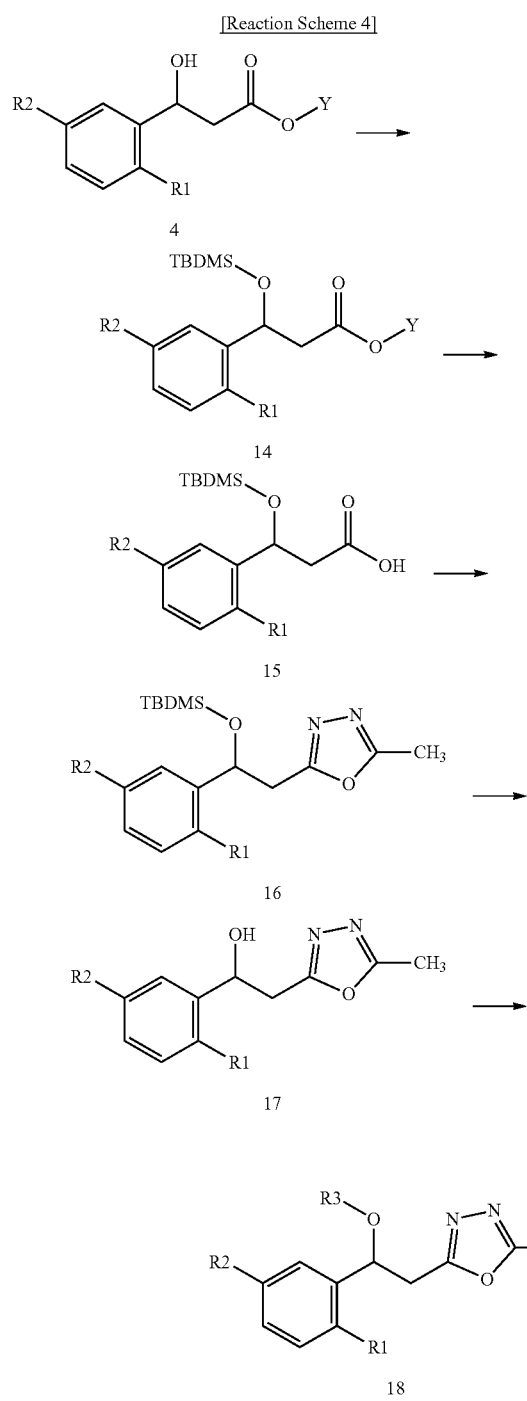

As another synthesis method, an intermediate compound 14 in which a protecting group is introduced to a hydroxy group is obtained using the intermediate compound 4 of Reaction Scheme 1 as a starting material, and then a carboxylic acid intermediate compound 15 is obtained through a hydrolysis reaction. The intermediate 16 into which oxadiazole is introduced is obtained from the compound through a cyclization reaction, and a final compound 18 may be obtained via nucleophilic substitution of the hydroxy group in the last step after deprotection group reaction.

[Reaction Scheme 5]

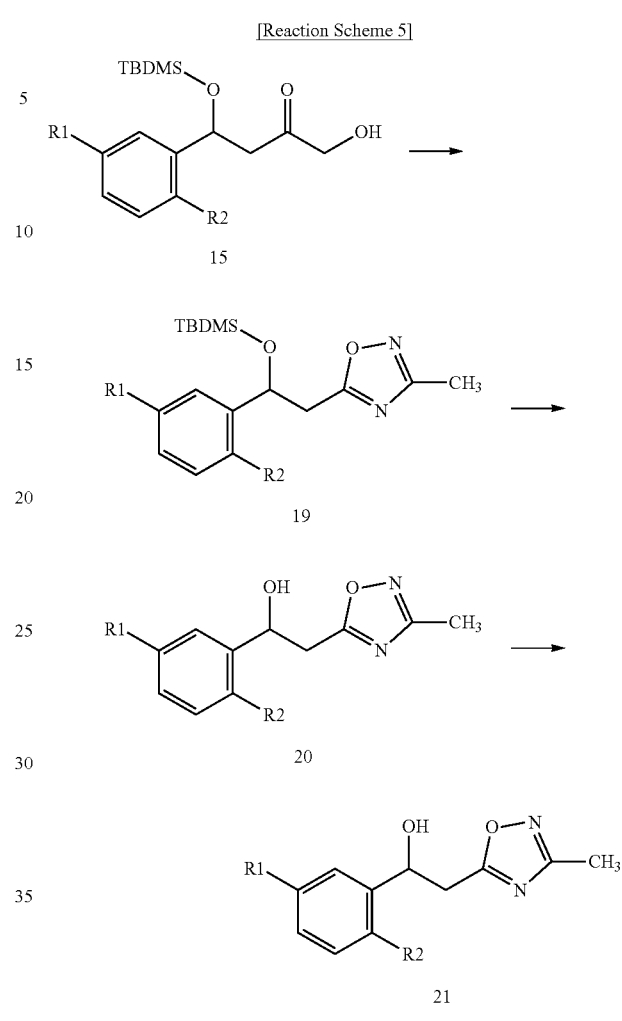

As another synthesis method, an intermediate 19 into which oxadiazole is introduced may be obtained through a cyclization reaction using an intermediate compound 15 of Reaction Scheme 4 as a starting material, and a final compound 21 may be obtained through a nucleophilic substitution reaction with a hydroxy group in a final step after a deprotection group reaction.

[Reaction Scheme 6]

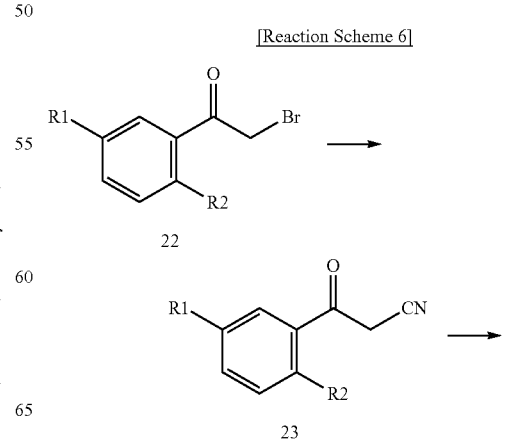

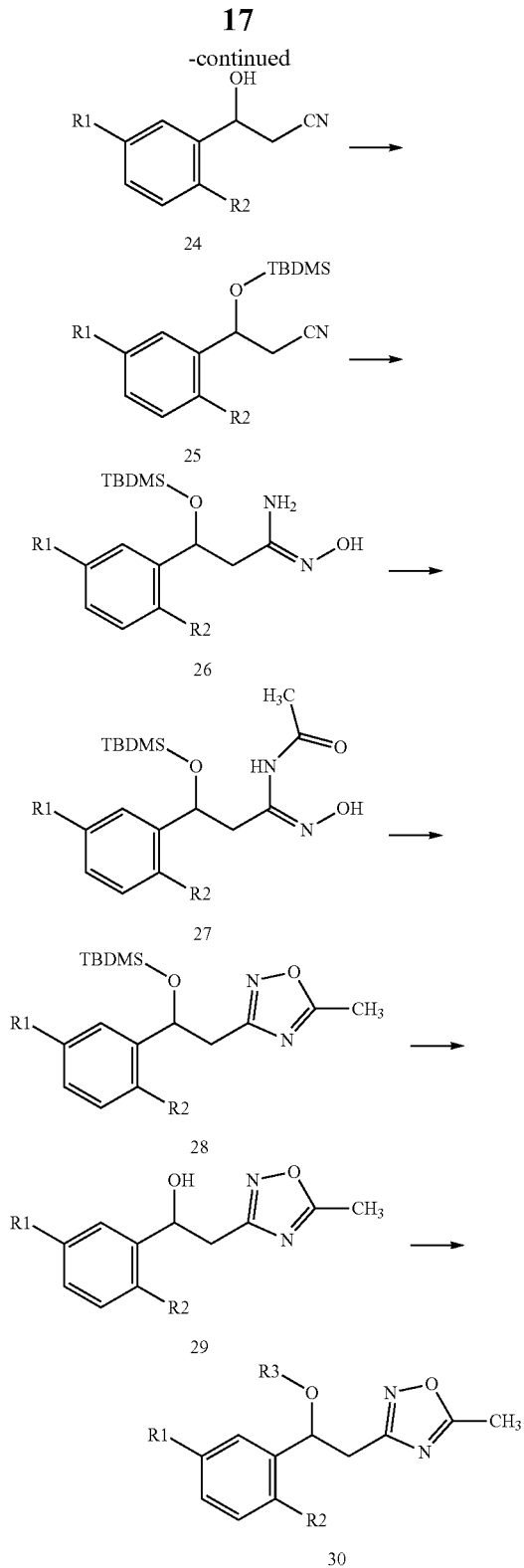

As another synthesis method, an intermediate compound 23 having a nitrile group introduced through a nucleophilic substitution reaction is obtained using compound 22 as a starting material, and then an intermediate compound 24 having a hydroxy group introduced through a reduction reaction is obtained. An intermediate compound 25 in which a protecting group is introduced to a hydroxy group is obtained, an intermediate 28 in which oxadiazole is introduced is obtained through a cyclization reaction of two stages, and a final compound 30 may be obtained through a nucleophilic substitution reaction of a hydroxy group in the final step after a deprotection group reaction.

The compounds that are not specifically described in the preparation method of the present specification are compounds known or compounds that can be easily synthesized from known compounds by known synthesis methods or similar methods.

The compound represented by Chemical Formula 1 obtained by the above method may be separated or purified by various known methods such as recrystallization, iontophoresis, silica gel column chromatography, or ion exchange resin chromatography from reaction product.

As described above, the compounds according to the present invention, starting materials or intermediates for preparation thereof, and the like, may be synthesized by various methods, and these methods should be construed to be included in the scope of the present invention in relation to the preparation of the compound of Chemical Formula 1.

The compound represented by Chemical Formula 1 according to the present invention has an effect of preventing or treating epilepsy. Accordingly, the present invention includes a medicament comprising a therapeutically effective amount of a compound of Chemical Formula 1 as an active ingredient, and a pharmaceutical composition for the prevention or treatment of epilepsy comprising a therapeutically effective amount of a compound of Chemical Formula 1 as an active ingredient, together with a pharmaceutically acceptable carrier. In addition, prodrugs having various forms that are converted to a compound of Chemical Formula 1 as desired in vivo are also within the scope of the present invention.

As used herein, the term "treatment" refers to the interruption, delay or alleviation of disease progression when used in a subject having a symptom.

As used herein, the term "prevention" refers to reduce the possibility of disease or eliminate the possibility of disease.

As used herein, the term "pharmaceutical composition" may include other chemical components, such as carriers, diluents, excipients, and the like in addition to the active compounds according to the present invention. Accordingly, the pharmaceutical composition may include a pharmaceutically acceptable carrier, diluent, excipient, or a combination thereof, if necessary. The pharmaceutical composition facilitates administration of the active compound into the organism. A variety of techniques for administering pharmaceutical compositions comprising a compound are known, in which the techniques includes oral, injection, aerosol, parenteral, and topical administration, but not limited thereto. In addition, the pharmaceutical composition may be sterilized, may further include an adjuvant such as a preservative, a stabilizer, a hydrating or an emulsifying accelerator, a salt for osmotic pressure regulation, and/or a buffer, may further include other therapeutically useful substances, and may be formulated according to conventional methods of mixing, granulating or coating.

As used herein, the term "carrier" refers to a compound that facilitates injection of a compound into a cell or tissue. For example, dimethylsulfoxide (DMSO) is a common carrier for easy input of a large amount of organic compounds into cells or tissues of an organism.

As used herein, the term "diluent" refers to a compound that stabilizes the biologically active form of the compound of interest, and is diluted in water that dissolves the compound. The salt dissolved in the buffer is used as a diluent in the art. A commonly used buffer is phosphate-buffered saline that imitates the salt form of a human body solution. Since the buffer salt is capable of controlling the pH of the solution at low concentrations, the buffer diluent rarely modifies the biological activity of the compound.

As used herein, the term "pharmaceutically acceptable" refers to a property that does not damage biological activity and physical properties of a compound.

The compound of the present invention may be formulated in various pharmaceutical administration forms as desired. When the pharmaceutical composition according to the present invention is prepared, the active ingredient, specifically the compound of Chemical Formula 1, a pharmaceutically acceptable salt or isomer thereof, is mixed with various pharmaceutically acceptable carriers which can be selected according to the formulation to be prepared. For example, the pharmaceutical composition according to the present invention may be formulated as an injectable preparation, an oral preparation, and the like, as desired.

For example, the pharmaceutical composition may be formulated into any dosage form for oral administration, such as tablets, pills, hard/soft capsules, solutions, suspensions, emulsifiers, syrups, granules or elixirs. The formulation for oral administration may include, for example, a pharmaceutically acceptable carrier, such as a diluent, such as lactose, dextrose, sucrose, mannitol, sorbitol, cellulose, and/or glycine, or a lubricant, such as silica, talc, stearic acid, magnesium or calcium salt thereof, and/or polyethylene glycol, in addition to the active ingredient, according to the typical configuration of each formulation.

In addition, when the formulation for oral administration is a tablet, the formulation may include a binder such as magnesium aluminum silicate, starch paste, gelatin, tragacanth, methylcellulose, sodium carboxymethyl cellulose, and/or polyvinylpyrrolidine, and optionally, may include a disintegrant such as starch, agar, alginic acid or a sodium salt thereof, a boiling mixture, and/or an absorbent, a colorant, a flavoring agent, or a sweetening agent.

When the pharmaceutical composition is formulated into a parenteral dosage form, the pharmaceutical composition may be administered by a parenteral administration method such as subcutaneous injection, intravenous injection, intramuscular injection or intrathoracic injection. The pharmaceutical composition may be prepared as a solution or a suspension by mixing an active ingredient—i.e., a compound of Chemical Formula 1 or a pharmaceutically acceptable salt thereof, with a stabilizer or a buffer in water, and the solution or the suspension may be prepared as a unit dosage form of an ampoule or a vial.

The compound of the present invention can be formulated by a known method using a known pharmaceutical carrier and an excipient and can be contained in a unit capacity form or a multi-capacity container. The form of the preparation may be a solution, a suspension or an emulsion in oil or aqueous medium, and may contain a conventional dispersing agent, a suspending agent or a stabilizer. In addition, for example, the dry powder may be dissolved in water from which sterility or exothermic material has been removed and be used. If necessary, the compound according to the present invention or the pharmaceutical composition containing the same may be administered in combination with another therapeutic agent.

The dosage of the compound of Chemical Formula 1 of the present invention may be determined according to a physician's prescription according to factors such as the specific properties of the patient's weight, age and disease, and severity. For example, the compound of Formula 1 of the present invention may be included in the pharmaceutical composition in an effective amount of 0.1 to 500 mg/kg (body weight), preferably 0.5 to 100 mg/kg (body weight) per day, with respect to mammals including humans, and the pharmaceutical composition may be divided once or twice a day and administered via an oral or parenteral route.

Advantageous Effects

The compound of chemical formula 1 according to the present invention has an effect of treating nervous system diseases, and specifically has an effect of anticonvulsant and antiepileptic drug. The compound can provide an excellent anticonvulsant effect in comparison with levetiracetam, topiramate and lamotrigine, at a 6-Hz model which is a refractory focal onset seizure animal model.

DETAILED DESCRIPTION

Hereinafter, the present invention is explained in more detail with the following examples. However, it must be understood that the protection scope of the present disclosure is not limited to the examples.

Example 1: Synthesis of 1-[5-(4-chlorophenyl)-2-fluoro-phenyl]-2-(5-methyl-1,3,4-oxadiazol-2-yl) ethanol

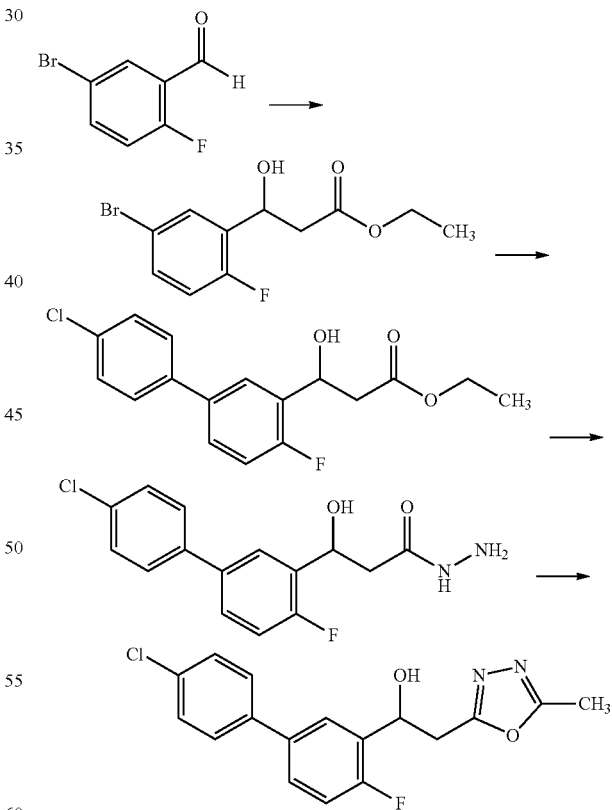

Example 1-1: Synthesis of ethyl 3-(5-bromo-2-fluoro-phenyl)-3-hydroxy-propanoate Diethyl zinc (1.0 M n-hexane solution, 24.3 mL, 24.3 mmol) was slowly added to 100 mL solution of diethyl ether in which 5-bromo-2-fluoro-benzaldehyde (1.9 mL, 16.2 mmol) and ethyl iodoacetate (2.9 mL, 24.3 mmol) were dissolved, under ice bath while maintaining the temperature at 0° C. The reaction mixture was stirred at the same temperature for 1 hour, and then added 100 mL of ethyl acetate, washed with saturated aqueous sodium bicarbonate solution and saturated aqueous sodium chloride solution once each, and dried over anhydrous magnesium sulfate. The light brown oil liquid obtained by removing the solvent by evaporation under reduced pressure was purified by flash chromatography to obtain the title compound in light yellow oil liquid.

Example 1-2: Synthesis of ethyl 3-[5-(4-chlorophenyl)-2-fluoro-phenyl)-3-hydroxy-propanoate 4-Chlorophenylboronic acid (0.8 g, 5.1 mmol), Pd(PPh3)2Cl2 (0.2 g, 0.3 mmol) and 3.4 mL of 2M potassium carbonate aqueous solution were sequentially added to 20 mL solution of 1, 4-dioxane in which ethyl 3-(5-bromo-2-fluoro-phenyl)-3-hydroxy-propanoate (1.0 g, 3.4 mmol) obtained in Example 1-1 was dissolved, and the mixture was stirred at 90° C. for 1 hour. The temperature was lowered to room temperature, 50 mL of ethyl acetate was added to the reaction mixture, and then the mixture was washed with saturated aqueous sodium bicarbonate solution and saturated aqueous sodium chloride solution once each, and the organic layer was dried over anhydrous magnesium sulfate. The dark brown oily liquid obtained by removing the solvent by evaporation under reduced pressure was purified by flash chromatography to obtain the title compound in yellow solid.

Example 1-3: Synthesis of 3-[5-(4-chlorophenyl)-2-fluoro-phenyl)-3-hydroxy-propanhydrazide Hydrazine monohydrate (0.3 g, 6.2 mmol) was added to 20 mL of ethanol dissolved with ethyl 3-[5-(4-chlorophenyl)-2-fluoro-phenyl)-3-hydroxy-propanoate (1 g, 3.1 mmol) obtained in Example 1-2, and heated and refluxed for 18 hours. The reaction mixture was cooled to room temperature and left for about 1 hour to wash the obtained white solid with isopropyl ether, and filter the same to obtain the title compound.

Example 1-4: Synthesis of 1-[5-(4-chlorophenyl)-2-fluoro-phenyl)-2-(5-methyl-1,3,4-oxadiazol-2-yl)ethanol N, N'-dimethylacetamide dimethylacetal (0.6 g, 4.8 mmol) was added to 20 mL of toluene containing 3-[5-(4-chlorophenyl)-2-fluoro-phenyl)-3-hydroxy-propanhydrazide (1 g, 3.2 mmol) obtained in Example 1-3, and heated and refluxed for about 1 hour at 110° C., and para-toluenesulfonic acid (57 mg, 0.3 mmol) was added thereto, and additionally heated and refluxed for about 18 hours. The temperature was lowered to room temperature, 100 mL of ethyl acetate was added to the reaction mixture, and the mixture was sequentially washed with a saturated aqueous ammonium chloride solution, a saturated aqueous sodium bicarbonate solution, and a saturated aqueous sodium chloride solution once each, and then the organic layer was dried over anhydrous magnesium sulfate. The solvent was removed by evaporation under reduced pressure, and isopropyl ether was added to the reaction mixture and left at room temperature for 1 hour to wash the produced white solid with isopropyl ether and filter the same to synthesize the title compound. NMR data of the synthesized title compound are as follows.

$^1$H-NMR (CDCl$_3$, 400 MHz) δ=7.77 (d, J=8.5 Hz, 1H), 7. 50-7. 40 (m, 5H), 7.12 (t, J=11.5 Hz, 1H), 5. 60-5. 58 (m, 1H), 3.56 (d, J=4.5 Hz, 1H), 3. 29-3. 22 (m, 2H), 2.53 (s, 3H).

Example 2: Synthesis of 1-[2-fluoro-5-[4-(trifluoromethyl)phenyl]phenyl]-2-(5-methyl-1,3,4-oxadiazol-2-yl)ethanol

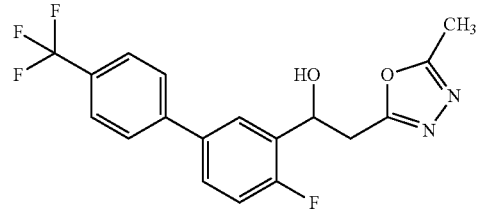 [SMILES: Cc1nnc(CC(O)c2cc(-c3ccc(C(F)(F)F)cc3)ccc2F)o1]

The title compound was synthesized in the same manner as in Example 1, except that 4-trifluoromethylboronic acid was used instead of 4-chlorophenylboronic acid in Example 1-2.

$^1$H-NMR (CDCl$_3$, 400 MHz) δ=7.84 (d, J=8.5 Hz, 1H), 7. 71-7. 66 (m, 4H), 7. 52-7. 45 (m, 1H), 7.16 (t, J=12 Hz, 1H), 5. 20-5. 59 (m, 1H), 3.67 (d, J=5.0 Hz, 1H) 3. 31-3. 23 (m, 2H), 2.53 (s, 3H).

Example 3: Synthesis of [1-[2-fluoro-5-[4-(trifluoromethyl)phenyl]phenyl]-2-(5-methyl-1,3, 4-oxadiazole-2-yl)ethyl] carbamate

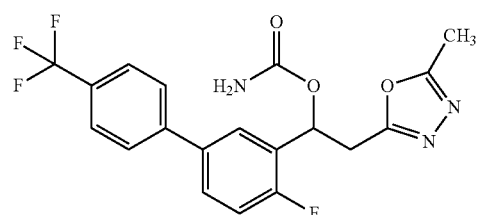

1,1'-Carbonyldiimidazole (0.6 g, 4.0 mmol) was added to 20 mL solution of tetrahydrofuran containing 1-[2-fluoro-5-[4-(trifluoromethyl)phenyl]phenyl]-2-(5-methyl-1, 3, 4-oxadiazole-2-yl)ethanol (1 g, 2.7 mmol) obtained in Example 2, and the mixture was stirred at room temperature for 6 hours. 2 mL of ammonia water was added to the reaction mixture and stirred at the same temperature for 30 minutes, and then 100 mL of ethyl acetate was added, washed with saturated aqueous sodium bicarbonate solution and saturated aqueous sodium chloride solution once each, and dried over anhydrous magnesium sulfate. Light yellow oil liquid obtained by removing the solvent by evaporation under reduced pressure was purified by flash chromatography to obtain the title compound as white solid.

$^1$H-NMR (CDCl$_3$, 400 MHz) δ=7. 70-7. 52 (m, 6H), 7.17 (t, J=11.5 Hz, 1H), 6.37 (brs, 1H), 5. 01 (brs, 2H) 3. 53-3. 37 (m, 3H), 2.53 (s, 3H).

Example 4: Synthesis of [1-[5-(4-chlorophenyl)-2-fluoro-phenyl]-2-(5-methyl-1,3,4-oxadiazol-2-yl)ethyl] carbamate

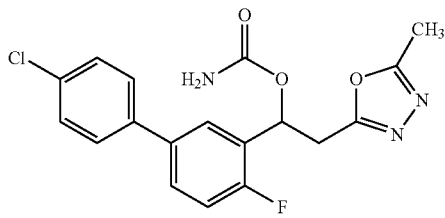 [SMILES: Cc1nnc(CC(OC(N)=O)c2cc(-c3ccc(Cl)cc3)ccc2F)o1]

1-[5-(4-Chlorophenyl)-2-fluoro-phenyl)-2-(5-methyl-1,3,4-oxadiazol-2-yl)ethanol, which was the final compound of Example 1, as a starting material was used in the same manner as in Example 3 to obtained the title compound.

$^1$H-NMR (CDCl$_3$, 400 MHz) δ=7.53 (d, J=8.0 Hz, 1H), 7. 45-7. 38 (m, 4H), 7.13 (m, 1H), 6.34 (brs, 1H), 5.11 (brs, 2H, NH2), 3. 51-3. 35 (m, 2H), 2.47 (s, 3H).

Example 5: Synthesis of 1-[2-fluoro-5-[4-(trifluoromethyl)phenyl]phenyl]-2-(1,3,4-oxadiazol-2-yl)ethanol

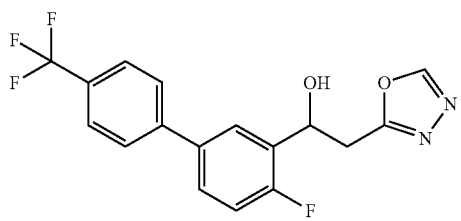 [SMILES: OC(Cc1nnco1)c1cc(-c2ccc(C(F)(F)F)cc2)ccc1F]

The title compound was synthesized in the same manner as in Example 1, except that 4-trifluoromethylboronic acid was used instead of 4-chlorophenylboronic acid in Example 1-2 and N,N'-dimethylformamide dimethylacetal was used instead of N,N'-dimethylacetamide dimethylacetal in Example 1-4.

$^1$H-NMR (CDCl$_3$, 400 MHz) δ=8.40 (s, 1H) 7.83 (d, J=8.5 Hz, 1H), 7. 70-7. 65 (m, 4H), 7.52 (brs, 1H) 7.16 (m, 1H), 5.64 (m, 1H), 3. 70 (brs, 1H), 3. 39-3. 34 (m, 2H).

Example 6: Synthesis of 2-(5-methyl-1,3,4-oxadiazol-2-yl)-1-[3-[4-(trifluoromethyl)phenyl]phenyl]ethanol

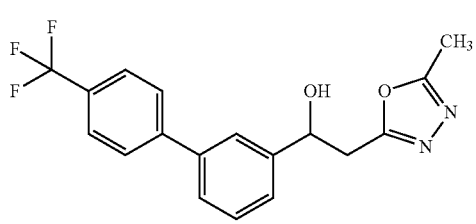

The title compound was synthesized in the same manner as in Example 1, except that 3-bromobenzaldehyde was used as a starting material and 4-trifluoromethylboronic acid was used instead of 4-chlorophenylboronic acid in Example 1-2.

$^1$H-NMR (CDCl$_3$, 400 MHz) δ=7. 70-7. 68 (m, 4H), 7. 57-7. 55 (m, 1H), 7. 51-7. 45 (m, 3H), 5. 37-5. 33 (m, 1H), 3. 34-3. 24 (m, 3H), 2.53 (s, 3H).

Example 7: Synthesis of [2-(5-methyl-1,3,4-oxadiazol-2-yl)-1-[3-[4-(trifluoromethyl)phenyl]phenyl]ethyl]carbamate

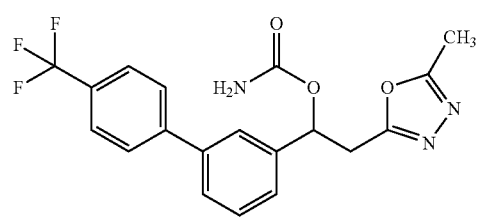 [SMILES: Cc1nnc(CC(OC(N)=O)c2cccc(-c3ccc(C(F)(F)F)cc3)c2)o1]

2-(5-Methyl-1,3,4-oxadiazol-2-yl)-1-[3-[4-(trifluoromethyl)phenyl]phenyl]ethanol, which was the final compound of Example 6, as a starting material was used in the same manner as in Example 3 to obtained the title compound.

$^1$H-NMR (CDCl$_3$, 400 MHz) δ=7.67 (dd, J=10.0, 17.5 Hz, 4H), 7. 58-7. 39 (m, 4H), 6.13 (s, 1H), 4.95 (brs, 2H, NH2), 3. 52-3. 29 (m, 2H), 2.49 (s, 3H).

Example 8: Synthesis of 2-(5-methyl-1,3,4-oxadiazol-2-yl)-1-[3-(2,2,3,3-tetrafluoropropoxy)phenyl]ethanol

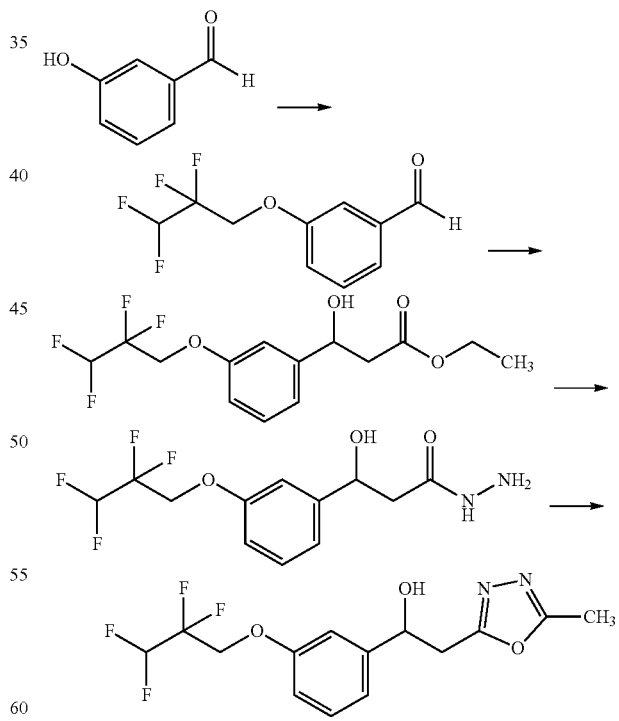

Example 8-1: Synthesis of 3-(2,2,3,3-tetrafluoropropoxy)benzaldehyde 2,2,3,3-Tetrafluoropropanol (1.6 g, 12.3 mmol) was added to 20 mL of tetrahydrofuran in which 3-hydroxybenzaldehyde (1.0 g, 8.2 mmol) and triphenylphosphine (3.2 g, 12.3 mmol) were dissolved, cooled to 0° C. under ice bath, and diisopropyl azdicarboxylate (1.9 g, 9.84 mmol) was slowly added dropwise thereto while maintaining the temperature. The reaction mixture was stirred at room temperature for 18 hours, washed with saturated aqueous sodium bicarbonate solution and saturated aqueous sodium chloride solution once each, and dried over anhydrous magnesium sulfate. The light yellow oil liquid obtained by removing the solvent by evaporation under reduced pressure was purified by flash chromatography to obtain the title compound in a light yellow liquid.

Example 8-2: Synthesis of ethyl 3-hydroxy-[3-(2,2, 3,3-tetrafluoropropoxy)phenyl]propanoate Diethyl zinc (1.0 M n-hexane solution, 6.4 mL, 6.4 mmol) was slowly added to 20 mL of diethyl ether in which 3-(2,2,3,3-tetrafluoropropoxy)benzaldehyde (1.0 g, 4.2 mmol) and ethyl iodoacetate (1.4 g, 6.4 mmol) obtained in Example 8-1 were dissolved under ice bath while maintaining the temperature at 0° C. The reaction mixture was stirred at the same temperature for 1 hour, and then 100 mL of ethyl acetate was added, washed with saturated aqueous sodium bicarbonate solution and saturated aqueous sodium chloride solution once each, and dried over anhydrous magnesium sulfate. The light brown oil liquid obtained by removing the solvent by evaporation under reduced pressure was purified by flash chromatography to obtain the title compound as light yellow oil liquid.

Example 8-3: Synthesis of 3-hydroxy-3-[3-(2,2,3,3-tetrafluoropropoxy)phenyl]propanhydrazide Hydrazine monohydrate (0.3 g, 6.2 mmol) was added to 20 mL of ethanol dissolved with ethyl 3-hydroxy-[3-(2,2,3-tetrafluoropropoxy)phenyl]propanoate (1.0 g, 3.1 mmol) obtained in Example 8-2, and heated and refluxed for 18 hours. The reaction mixture was cooled to room temperature and left for about 1 hour to wash the produced white solid with isopropyl ether, and filter the same to obtain the title compound.

Example 8-4: Synthesis of 2-(5-methyl-1,3,4-oxadiazol-2-yl)-1-[3-(2,2,3,3-tetrafluoropropoxy)phenyl]ethanol N,N'-dimethylacetamide dimethylacetal (0.6 g, 4.8 mmol) was added to 20 mL of toluene containing 3-hydroxy-3-[3-(2,2,3,3-tetrafluoropropoxy)phenyl]propanhydrazide (1.0 g, 3.2 mmol) obtained from Example 8-3, heated and refluxed at 110° C. for about 1 hour, and para-toluenesulfonic acid (57 mg, 0.3 mmol) was added thereto, and heated and refluxed for about 18 hours. The temperature was lowered to room temperature, 100 mL of ethyl acetate was added to the reaction mixture, and then the mixture was sequentially washed with a saturated aqueous ammonium chloride solution, a saturated aqueous sodium bicarbonate solution, and a saturated aqueous sodium chloride solution once each, and the organic layer was dried over anhydrous magnesium sulfate. The solvent was removed by evaporation under reduced pressure, and isopropyl ether was added to the reaction mixture and left at room temperature for 1 hour to wash the produced white solid with isopropyl ether, and filter the same to obtain the title compound.

$^1$H-NMR (CDCl$_3$, 400 MHz) δ=7. 30-6. 85 (m, 4H), 6. 21-5. 94 (t, J=66.5 Hz, 1H), 5. 22-5. 20 (m, 1H), 4. 37 (t, J=14.5 Hz, 2H), 4.15 (s, 1H), 3. 18-3. 16 (m, 2H), 2.48 (s, 3H).

Example 9: Synthesis of [2-(5-methyl-1,3,4-oxadiazol-2-yl)-1-[3-(2,2,3,3-tetrafluoropropoxy)phenyl]ethyl]carbamate

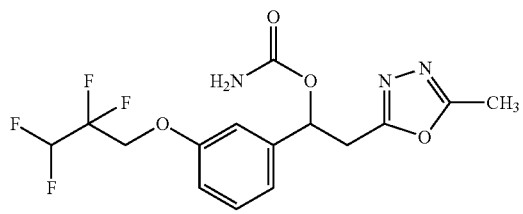 [SMILES: Cc1nnc(CC(OC(N)=O)c2cccc(OCC(F)(F)C(F)F)c2)o1]

2-(5-Methyl-1,3,4-oxadiazol-2-yl)-1-[3-(2,2,3,3-tetrafluoropropoxy)phenyl]ethanol, which is the final compound of Example 8, as a starting material was used in the same manner as in Example 3 to obtain the title compound.

$^1$H-NMR (CDCl$_3$, 400 MHz) δ=7.29 (dd, J=9.0, 18.0 Hz, 1H), 7.29 (dd, J1=9.0, 10.5 Hz, 2H), 6.96 (s, 1H), 6. 20-5. 94 (m, 2H), 4.98 (brs, 2H, NH2), 4.37 (t, J=14.5 Hz, 2H) 4.35 (t, J=14.5 Hz, 2H), 3. 43-3. 41 (m, 1H), 3.24 (d, J=18.5 Hz, 1H), 2.49 (s, 3H).

Example 10: Synthesis of 1-[2-fluoro-5-(3,3,3-trifluoropropyl)phenyl]-2-(5-methyl-1,3,4-oxadiazol-2-yl)ethanol

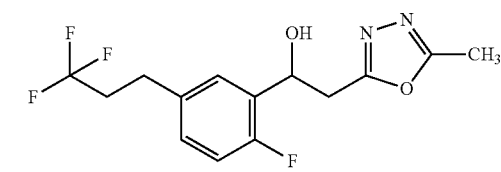 [SMILES: Cc1nnc(CC(O)c2cc(CCC(F)(F)F)ccc2F)o1]

The title compound was synthesized in the same manner as in Example 1, except that 3,3,3-trifluoropropylboronic acid was used instead of 4-chlorophenylboronic acid in Example 1-2.

$^1$H-NMR (CDCl$_3$, 400 MHz) δ=7. 43-7. 41 (m, 1H), 7. 13-7. 11 (m, 1H), 6.99 (t, J=12.0 Hz, 1H), 5. 54-5. 52 (m, 1H), 3.55 (s, 1H), 3.27 (d, J=20.0 Hz, 2H), 3.17 (dd, J1=11.5, 20.0 Hz, 1H), 2.87 (t, J=9.5 Hz, 2H), 2.53 (s, 3H), 2.39 (dd, J1=12.5, 22 Hz, 1H).

Example 11: Synthesis of [1-[2-fluoro-5-(3,3,3-trifluoropropyl)phenyl]-2-(5-methyl-1,3,4-oxadiazol-2-yl)ethyl] carbamate

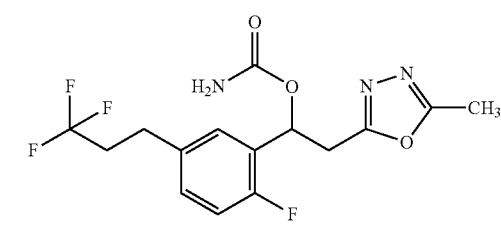 [SMILES: Cc1nnc(CC(OC(N)=O)c2cc(CCC(F)(F)F)ccc2F)o1]

1-[2-Fluoro-5-(3,3,3-trifluoropropyl)phenyl]-2-(5-methyl-1,3,4-oxadiazol-2-yl)ethanol, which is the final compound of Example 10, as a starting material was used in the same manner as in Example 3 to obtain the title compound.

¹H-NMR (CDCl₃, 400 MHz) δ=7.19 (d, J=8.0 Hz, 1H), 7. 14-7. 12 (m, 1H), 7.02 (t, J=11.5 Hz, 1H), 6.28 (brs, 1H), 4.77 (brs, 2H, NH2), 3. 45-3. 35 (m, 2H), 2.85 (t, J=9.5 Hz, 2H), 2.50 (s, 3H), 2.36 (dd, J1=12.5, 22 Hz, 1H).

Example 12: Synthesis of 1-[2-fluoro-5-(3,3,3-trifluoropropyl)phenyl]-2-(1,3,4-oxadiazol-2-yl)ethanol

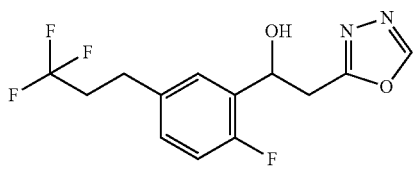 [SMILES: OC(Cc1nnco1)c1cc(CCC(F)(F)F)ccc1F]

The title compound was synthesized in the same manner as in Example 1, except that 3,3,3-trifluoropropylboronic acid was used instead of 4-chlorophenylboronic acid in Example 1-2, and N,N'-dimethylacetamide dimethylacetal was used instead of N,N'-dimethylacetamide dimethylacetal in Example 1-4.

¹H-NMR (CDCl₃, 400 MHz) δ=8.39 (s, 1H), 7.41 (d, J=6.5 Hz, 1H), 7. 13-7. 11 (m, 1H), 7.00 (t, J=12.5 Hz, 1H), 5. 57-5. 55 (m, 1H), 3. 37-3. 28 (m, 2H), 2. 88-2. 84 (m, 3H), 2. 41-2. 34 (m, 2H).

Example 13: Synthesis of (1R)-2-(5-methyl-1,3,4-oxadiazol-2-yl)-1-[3-[4-(trifluoromethyl)phenyl]phenyl]ethanol

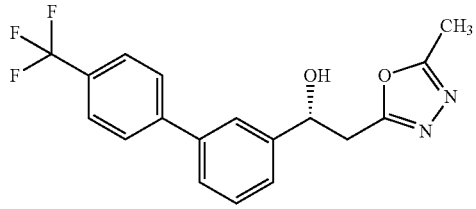

2-(5-Methyl-1,3,4-oxadiazol-2-yl)-1-[3-[4-(trifluoromethyl)phenyl]phenyl]ethanol, which is the final compound of Example 6, as a starting material was used to separate the optical isomer compound by the use of a preparative HPLC device on a chiralpakAD column (2×20 cm), n-hexane:ethylacetate=90:10 at a flow rate of 20 mL/min.

¹H-NMR (CDCl₃, 400 MHz) δ=7. 70-7. 68 (m, 4H), 7. 57-7. 55 (m, 1H), 7. 51-7. 45 (m, 3H), 5. 37-5. 33 (m, 1H), 3. 34-3. 24 (m, 3H), 2.53 (s, 3H).

Example 14: Synthesis of (1S)-2-(5-methyl-1,3,4-oxadiazol-2-yl)-1-[3-[4-(trifluoromethyl)phenyl]phenyl]ethanol

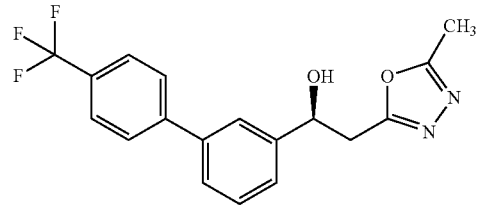 [SMILES: Cc1nnc(C[C@H](O)c2cccc(-c3ccc(C(F)(F)F)cc3)c2)o1]

2-(5-Methyl-1,3,4-oxadiazol-2-yl)-1-[3-[4-(trifluoromethyl)phenyl]phenyl]ethanol, which is the final compound of Example 6, as a starting material was used to separate the optical isomer compound by the use of a preparative HPLC device a chiralpak AD column (2×20 cm), n-hexane:ethyl acetate=90:10 at a flow rate of 20 mL/min.

¹H-NMR (CDCl₃, 400 MHz) δ=7. 70-7. 68 (m, 4H), 7. 57-7. 55 (m, 1H), 7. 51-7. 45 (m, 3H), 5. 37-5. 33 (m, 1H), 3. 34-3. 24 (m, 3H), 2.53 (s, 3H).

Example 15: Synthesis of 1-[2-fluoro-5-(4,4,4-trifluorobutoxy)phenyl]-2-(5-methyl-1,3,4-oxadiazol-2-yl)ethanol

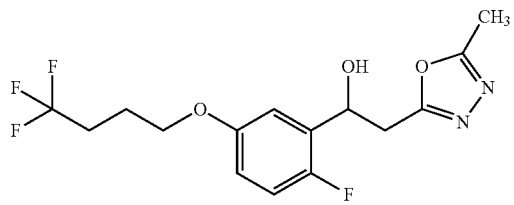 [SMILES: Cc1nnc(CC(O)c2cc(OCCCC(F)(F)F)ccc2F)o1]

The title compound was synthesized in the same manner as in Example 8, except that 2-fluoro-5-hydroxybenzaldehyde was used as a starting material in Example 8-1 and 4,4,4-trifluorobutanol was used instead of 2,2,3,3-tetrafluoropropanol.

¹H-NMR (CDCl₃, 400 MHz) δ=7. 11-7. 09 (m, 1H), 6.99 (d, J=9.6 Hz, 1H), 6. 79-6. 76 (m, 1H), 5. 51-5. 48 (m, 1H), 4. 01-3. 98 (m, 2H), 3.52 (d, J=4.0 Hz, 1H), 3. 28-3. 12 (m, 2H), 2.52 (s, 3H), 2. 34-2. 27 (m, 2H), 2. 07-2. 02 (m, 2H).

Example 16: Synthesis of [1-[2-fluoro-5-(4,4,4-trifluorobutoxy)phenyl]-2-(5-methyl-1,3,4-oxadiazol-2-yl)ethyl] carbamate

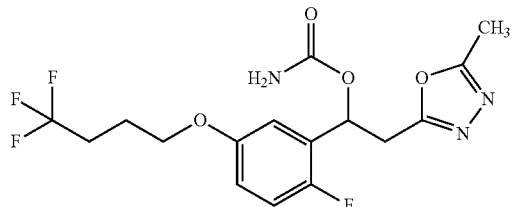

1-[2-Fluoro-5-(4,4,4-trifluorobutoxy)phenyl]-2-(5-methyl-1,3,4-oxadiazol-2-yl)ethanol, which is the final compound of Example 15, as a starting material was used in the same manner as in Example 3 to obtain the title compound.

$^1$H-NMR (CDCl$_3$, 400 MHz) δ=6.98 (t, J=11.5 Hz, 1H), 6.88 (dd, J1=4.0, 7.0 Hz, 1H), 6.25 (dd, J=6.0, 10.5 Hz, 1H), 5.05 (brs, 2H, NH2), 3.96 (t, J=7.5 Hz, 2H) 3.43 (dd, J=10.5, 19.0 Hz, 1H), 3.31 (dd, J=6.0, 19.0 Hz, 1H), 2.49 (s, 3H), 2.31-2.29 (m, 2H), 2.03-2.01 (m, 2H).

Example 17: Synthesis of 1-[2-fluoro-5-(2,2,2-trifluoroethoxy)phenyl]-2-(5-methyl-1,3,4-oxadiazol-2-yl)ethanol

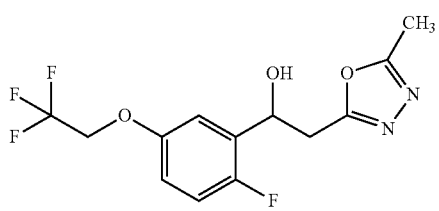 [SMILES: Cc1nnc(CC(O)c2cc(OCC(F)(F)F)ccc2F)o1]

The title compound was synthesized in the same manner as in Example 8, except that 2-fluoro-5-hydroxybenzaldehyde was used as a starting material in Example 8-1, and 2,2,2-trifluoroethanol was used instead of 2,2,3,3-tetrafluoropropanol.

$^1$H-NMR (CDCl$_3$, 400 MHz) δ=7.21-7.19 (m, 1H), 7.01 (t, J=11.5 Hz, 1H), 6.89-6.85 (m, 1H), 5.53-5.49 (m, 1H), 4.35 (q, J=10 Hz, 2H), 3.65 (d, J=5.5 Hz, 1H), 3.27 (dd, J=4.0, 20.5 Hz, 1H), 3.13 (dd, J=11.5, 20.5 Hz, 1H), 2.53 (s, 3H).

Example 18: Synthesis of [1-[2-fluoro-5-(2,2,2-trifluoroethoxy)phenyl]-2-(5-methyl-1,3,4-oxadiazol-2-yl)ethyl] carbamate

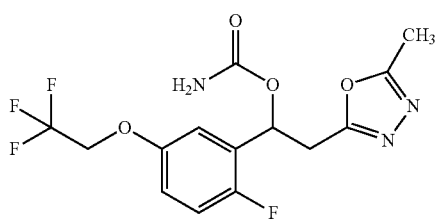 [SMILES: Cc1nnc(CC(OC(N)=O)c2cc(OCC(F)(F)F)ccc2F)o1]

1-[2-Fluoro-5-(2,2,2-trifluoroethoxy)phenyl]-2-(5-methyl-1,3,4-oxadiazol-2-yl)ethanol, which is a final compound of Example 17, as a starting material was used in the same manner as in Example 3 to obtain the title compound.

$^1$H-NMR (CDCl$_3$, 400 MHz) δ=7.03 (t, J=11.5 Hz, 1H), 6.97-6.95 (m, 1H), 6.88-6.84 (m, 1H), 6.29-6.26 (m, 1H), 4.74 (brs, 2H, NH2), 4.31 (q, J=10 Hz, 2H), 3.43 (dd, J=10.5, 19.5 Hz, 1H), 3.34 (dd, J=6.0, 19.5 Hz, 1H), 2.50 (s, 3H).

Example 19: Synthesis of 2-(5-methyl-1,3,4-oxadiazol-2-yl)-1-[3-(4,4,4-trifluorobutoxy)phenyl]ethanol

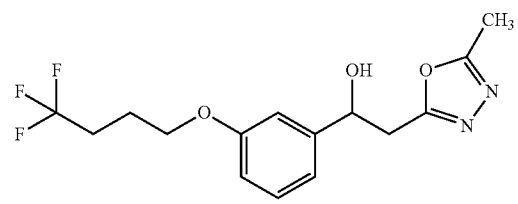 [SMILES: Cc1nnc(CC(O)c2cccc(OCCCC(F)(F)F)c2)o1]

The title compound was synthesized in the same manner as in Example 8, except that 4,4,4-trifluorobutanol was used instead of 2,2,3,3-tetrafluoropropanol in Example 8-1.

$^1$H-NMR (CDCl$_3$, 400 MHz) δ=7.29 (d, J=10.0 Hz, 1H), 6.99-6.97 (m, 2H), 6.84-6.82 (m, 1H), 5.23-5.21 (m, 1H), 4.02 (t, J=7.5 Hz, 2H), 3.32 (d, J=4.5 Hz, 1H) 3.19-3.17 (m, 1H), 2.51 (s, 3H), 2.33-2.31 (m, 2H), 2.05 (m, 2H).

Example 20: Synthesis of [2-(5-methyl-1,3,4-oxadiazol-2-yl)-1-[3-(4,4,4-trifluorobutoxy)phenyl]ethyl] carbamate

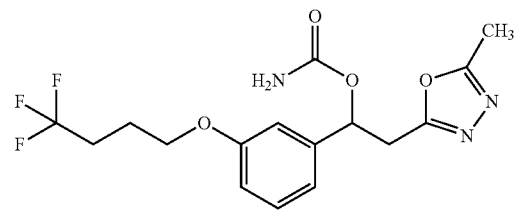 [SMILES: Cc1nnc(CC(OC(N)=O)c2cccc(OCCCC(F)(F)F)c2)o1]

2-(5-Methyl-1,3,4-oxadiazol-2-yl)-1-[3-(4,4,4-trifluorobutoxy)phenyl]ethanol, which is the final compound of Example 19, as a starting material was used in the same manner as in Example 3 to obtain the title compound.

$^1$H-NMR (CDCl$_3$, 400 MHz) δ=7.29 (d, J=10.0 Hz, 1H), 6.95 (d, J=10.0 Hz, 1H) 6.90-6.83 (m, 2H), 6.02 (m, 1H), 4.71 (brs, 2H, NH2), 4.01 (t, J=7.5 Hz, 2H), 3.43 (dd, J=11.0, 19.0 Hz, 1H), 3.26 (dd, J=6.0, 19.0 Hz, 1H), 2.50 (s, 3H), 2.33-2.31 (m, 2H), 2.06-2.04 (m, 2H).

Example 21: Synthesis of 1-(5-butoxy-2-fluorophenyl)-2-(5-methyl-1,3,4-oxadiazol-2-yl)ethanol

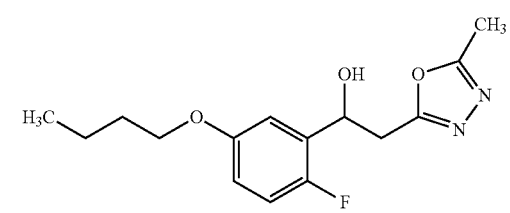 [SMILES: CCCCOc1ccc(F)c(C(O)Cc2nnc(C)o2)c1]

The title compound was synthesized in the same manner as in Example 8, except that n-butanol was used instead of 2,2,3,3-tetrafluoropropanol in Example 8-1.

$^1$H-NMR (CDCl3, 400 MHz) δ=7.11 (s, 1H), 6.94-6.92 (m, 1H), 6.78-6.76 (m, 1H), 5.49-5.47 (m, 1H), 4.04 (s,

1H, OH), 3. 95-3. 93 (m, 2H), 3. 23-3. 21 (m, 2H), 2.56 (s, 3H), 1. 78-1. 76 (m, 2H), 1. 53-1. 51 (m, 2H), 0. 96-0. 94 (m, 3H).

Example 22: Synthesis of [1-(5-butoxy-2-fluoro-phenyl)-2-(5-methyl-1,3,4-oxadiazol-2-yl)ethyl] carbamate

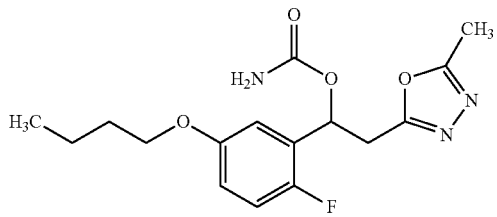 [SMILES: CCCCOc1ccc(F)c(C(Cc2nnc(C)o2)OC(N)=O)c1]

1-(5-Butoxy-2-fluoro-phenyl)-2-(5-methyl-1,3,4-oxadiazol-2-yl)ethanol, which is the final compound of Example 21, as a starting material was used in the same manner as in Example 3 to obtain the title compound.

$^1$H-NMR (CDCl$_3$, 400 MHz) δ=6. 97-6. 95 (m, 1H), 6. 87-6. 85 (m, 1H), 6. 77-6. 75 (m, 1H), 6. 25-6. 23 (m, 1H), 4.78 (s, 2H, NH2), 3. 95-3. 93 (m, 2H), 3. 48-3. 46 (m, 2H), 2.56 (s, 3H), 1. 78-1. 76 (m, 2H), 1. 53-1. 51 (m, 2H), 0. 94-0. 92 (m, 3H).

Example 23: Synthesis of 1-[2-fluoro-5-(4,4,4-trifluorobutoxy)phenyl]-2-(1,3,4-oxadiazol-2-yl)ethanol

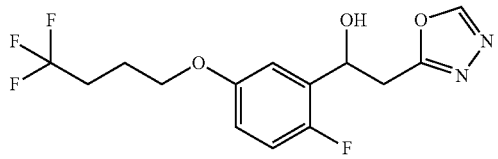 [SMILES: OC(Cc1nnco1)c1cc(OCCCC(F)(F)F)ccc1F]

The title compound was synthesized in the same manner as in Example 8, except that 2-fluoro-5-hydroxybenzaldehyde was used as a starting material in Example 8-1, 4,4,4-trifluorobutanol was used instead of 2,2,3,3-tetrafluoropropanol, and N,N'-dimethylformamide dimethylacetal was used instead of N,N'-dimethylacetamide dimethylacetal in Example 8-4.

$^1$H-NMR (CDCl$_3$, 400 MHz) δ=8.38 (s, 1H), 7.29 (dd, J=4.0, 7.5 Hz, 1H), 6.97 (t, J=11.0 Hz, 1H), 6. 80-6. 77 (m, 1H), 5. 54-5. 52 (m, 1H), 4. 00-3. 98 (m, 2H), 3.56 (d, J=5.0 Hz, 1H), 3.34 (dd, J=4.5, 20.0 Hz, 1H), 3.26 (dd, J=11.0, 20.0 Hz, 1H), 2. 33-2. 31 (m, 2H), 2. 05-2. 03 (m, 2H).

Example 24: Synthesis of [1-[2-fluoro-5-(4,4,4-trifluorobutoxy)phenyl]-2-(1,3,4-oxadiazol-2-yl)ethyl] carbamate

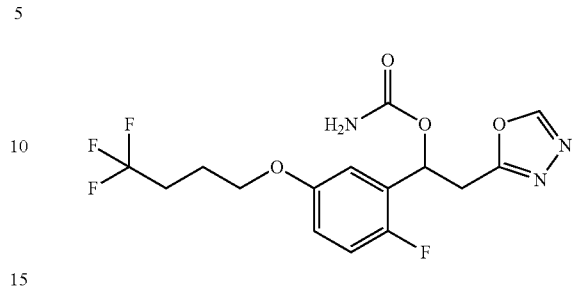

1-[2-Fluoro-5-(4,4,4-trifluorobutoxy)phenyl]-2-(1,3,4-oxadiazol-2-yl)ethanol, which is the final compound of Example 23, as a starting material was used in the same manner as in Example 3 to obtain the title compound.

$^1$H-NMR (CDCl$_3$, 400 MHz) δ=8.36 (s, 1H), 6.90 (t, J=12.0 Hz, 1H), 6. 87-6. 77 (m, 2H), 6.30 (dd, J=6.0, 10.5 Hz, 1H) 4.89 (brs, 2H, NH2), 3.96 (t, J=7.5 Hz, 2H), 3.53 (dd, J=10.5, 19.0 Hz, 1H), 3.42 (dd, J=6.0, 19.0 Hz, 1H), 2. 32-2. 30 (m, 2H), 2. 05-2. 03 (m, 2H).

Example 25: Synthesis of 1-(2-fluoro-5-propyl-phenyl)-2-(5-methyl-1,3,4-oxadiazol-2-yl)ethanol

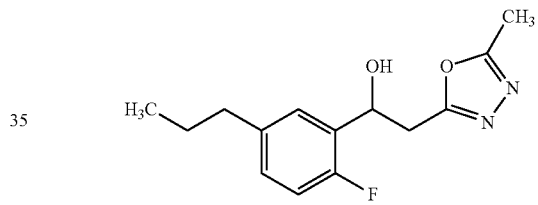

The title compound was synthesized in the same manner as in Example 1, except that normal propyl boronic acid was used instead of 4-chlorophenylboronic acid in Example 1-2.

$^1$H-NMR (CDCl$_3$, 400 MHz) δ=7. 36-7. 33 (m, 1H), 7. 10-7. 06 (m, 1H), 6. 97-6. 92 (m, 1H), 5. 52-5. 48 (m, 1H), 3. 29-3. 16 (m, 2H), 2.58 (t, J=7.6 Hz, 2H), 2.51 (s, 3H), 1. 66-1. 57 (m, 2H), 0. 94-0. 90 (t, J=7.2, 3H).

Example 26: Synthesis of 1-(2-fluoro-5-pentyl-phenyl)-2-(5-methyl-1,3,4-oxadiazol-2-yl)ethanol

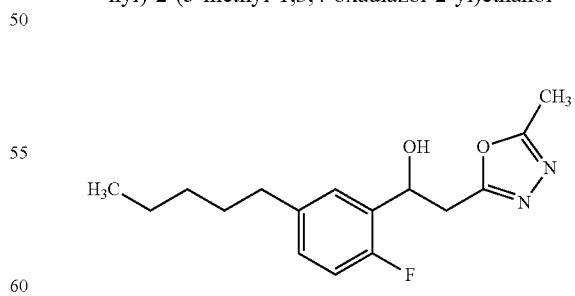

The title compound was synthesized in the same manner as in Example 1, except that N-chlorophenylboronic acid was used instead of 4-chlorophenylboronic acid in Example 1-2.

$^1$H-NMR (CDCl$_3$, 400 MHz) δ=7. 36-7. 34 (m, 1H), 7. 08-7. 06 (m, 1H), 6. 97-6. 92 (m, 1H), 5. 51-5. 48 (m, 1H), 3.25 (brs, 1H), 3. 24-3. 20 (m, 2H), 2.58 (t, J=8.0, 2H), 2.51 (s, 3H), 1. 60-1. 55 (m, 2H*2), 1. 34-1. 30 (m, 2H) 0. 90-0. 87 (t, J=6.8, 3H).

Example 27: Synthesis of [1-(2-fluoro-5-propyl-phenyl)-2-(5-methyl-1,3,4-oxadiazol-2-yl)ethyl] carbamate

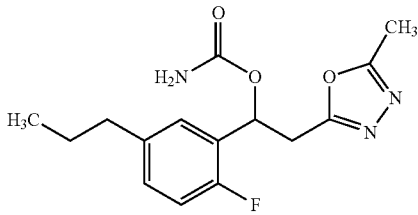 [SMILES: CCCc1ccc(F)c(C(Cc2nnc(C)o2)OC(N)=O)c1]

1-(2-Fluoro-5-propyl-phenyl)-2-(5-methyl-1,3,4-oxadiazol-2-yl)ethanol, which is the final compound of Example 25, as a starting material was used in the same manner as in Example 3 to obtain the title compound.

$^1$H-NMR (CDCl$_3$, 400 MHz) δ=7. 15-7. 12 (m, 1H), 7. 09-7. 08 (m, 1H), 6. 99-6. 94 (m, 1H), 6. 30-6. 26 (m, 1H), 4.13 (brs, 2H), 4.13 (dd, J=15.2, J=8.4, 1H), 3.36 (dd, J=15.2, J=4.8, 1H), 2.57 (t, J=7.6, 2H), 2.49 (s, 3H), 1. 66-1. 54 (m, 2H), 0. 93-0. 89 (t, J=7.2, 3H).

Example 28: Synthesis of [1-(2-fluoro-5-pentyl-phenyl)-2-(5-methyl-1,3,4-oxadiazol-2-yl)ethyl] carbamate

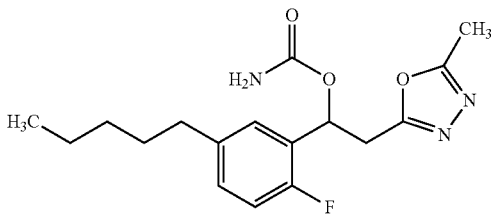 [SMILES: CCCCCc1ccc(F)c(C(Cc2nnc(C)o2)OC(N)=O)c1]

1-(2-Fluoro-5-pentyl-phenyl)-2-(5-methyl-1,3,4-oxadiazol-2-yl)ethanol, which is the final compound of Example 26, as a starting material was used in the same manner as in Example 3 to obtain the title compound.

$^1$H-NMR (CDCl$_3$, 400 MHz) δ=7. 15-7. 13 (m, 1H), 7. 09-7. 08 (m, 1H), 6. 98-6. 94 (m, 1H), 6. 29-6. 26 (m, 1H), 4.63 (brs, 2H), 3.49 (dd, J=15.2, J=8.8, 1H), 3.35 (dd, J=15.2, J=4.4, 1H), 2.56 (t, J=7.6, 2H), 2.49 (s, 3H), 1. 58-1. 54 (m, 2H), 1. 34-1. 25 (m, 2H*2), 0. 91-0. 89 (t, J=7.2, 3H).

Example 29: Synthesis of 1-[2-fluoro-5-(4,4,4-trifluorobutyl)phenyl]-2-(1,3,4-oxadiazol-2-yl)ethanol

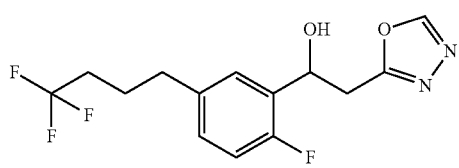 [SMILES: OC(Cc1nnco1)c1cc(CCCC(F)(F)F)ccc1F]

The title compound was synthesized in the same manner as in Example 1, except that 4,4,4-trifluorobutyric acid was used instead of 4-chlorophenylboronic acid in Example 1-2, and N,N'-dimethylacetamide dimethylacetal was used instead of N,N'-dimethylacetamide dimethylacetal in Example 1-4.

$^1$H-NMR (CDCl$_3$, 400 MHz) δ=8.38 (s, 1H), 7. 39-7. 36 (m, 1H), 7. 11-7. 10 (m, 1H), 7. 02-6. 98 (m, 1H), 5. 58-5. 55 (m, 1H), 3. 40-3. 26 (m, 3H), 2. 71-2. 67 (m, 2H), 2. 10-2. 05 (m, 2H), 2. 18-2. 05 (m, 2H), 1. 90-1. 86 (m, 2H).

Example 30: Synthesis of 1-[2-fluoro-5-(5,5,5-trifluoropentyl)phenyl]-2-(1,3,4-oxadiazol-2-yl)ethanol

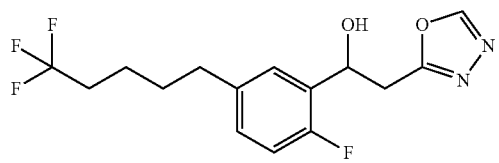 [SMILES: OC(Cc1nnco1)c1cc(CCCCC(F)(F)F)ccc1F]

The title compound was synthesized in the same manner as in Example 1, except that 5,5,5-trifluoropentylboronic acid was used instead of 4-chlorophenylboronic acid in Example 1-2, and N,N'-dimethylacetamide dimethylacetal was used instead of N,N'-dimethylacetamide dimethylacetal in Example 1-4.

$^1$H-NMR (CDCl$_3$, 400 MHz) δ=8.37 (s, 1H), 7.36 (dd, J=2.1, 7.0 Hz, 1H), 7. 12-7. 05 (m, 1H), 6.98 (dd, J=8.4, 10.2 Hz, 1H), 5.55 (dd, J=3.7, 8.3 Hz, 1H), 3. 37-3. 28 (m, 2H), 2.63 (t, J=7.5 Hz, 2H), 2. 1-2. 02 (m, 2H), 1. 73-1. 64 (m, 2H), 1.59 (d, J=7.2 Hz, 2H).

Example 31: Synthesis of 1-[2-fluoro-5-(4,4,4-trifluorobutyl)-phenyl]-2-(5-methyl-1,3,4-oxadiazol-2-yl)ethanol

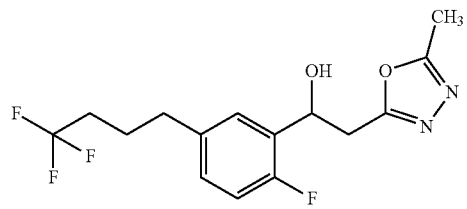 [SMILES: Cc1nnc(CC(O)c2cc(CCCC(F)(F)F)ccc2F)o1]

The title compound was synthesized in the same manner as in Example 1, except that 4,4,4-trifluorobutyric acid was used instead of 4-chlorophenylboronic acid in Example 1-2.

$^1$H-NMR (CDCl$_3$, 400 MHz) δ=7. 40-7. 38 (m, 1H), 7. 12-7. 09 (m, 1H), 7. 02-6. 97 (m, 1H), 5. 55-5. 51 (m, 1H), 3. 48-3. 46 (m, 1H), 3. 28-3. 19 (m, 2H), 2. 70-2. 67 (m, 2H), 2.50 (s, 3H), 2. 18-2. 05 (m, 2H), 1. 92-1. 86 (m, 2H).

Example 32: Synthesis of 1-[2-fluoro-5-(5,5,5-trifluoropentyl)-phenyl]-2-(5-methyl-1,3,4-oxadiazol-2-yl)ethanol

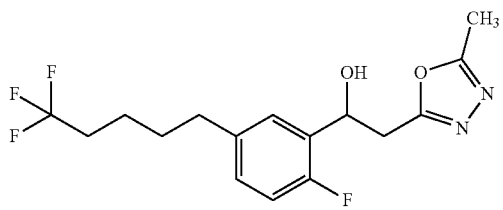 [SMILES: Cc1nnc(CC(O)c2cc(CCCCC(F)(F)F)ccc2F)o1]

The title compound was synthesized in the same manner as in Example 1, except that 5,5,5-trifluoropentylboronic acid was used instead of 4-chlorophenylboronic acid in Example 1-2.

$^1$H-NMR (CDCl$_3$, 400 MHz) δ=7.38 (dd, J=2.1, 7.0 Hz, 1H), 7.08 (ddd, J=2.3, 5.3, 8.1 Hz, 1H), 6.97 (dd, J=8.4, 10.3 Hz, 1H), 5. 56-5. 48 (m, 1H), 3.47 (d, J=4.4 Hz, 1H), 3. 33-3. 15 (m, 2H), 2. 69-2. 59 (m, 2H), 2.53 (s, 3H), 2. 21-2. 03 (m, 2H), 1. 74-1. 61 (m, 4H).

Example 33: Synthesis of [1-[2-fluoro-5-(4,4,4-trifluorobutyl)phenyl]-2-(5-methyl-1,3,4-oxadiazol-2-yl)ethyl] carbamate

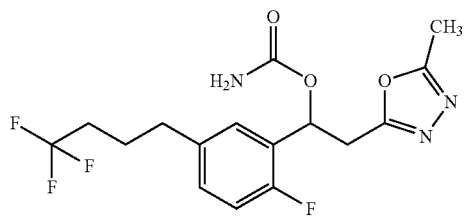 [SMILES: Cc1nnc(CC(OC(N)=O)c2cc(CCCC(F)(F)F)ccc2F)o1]

1-[2-Fluoro-5-(4,4,4-trifluorobutyl)-phenyl]-2-(5-methyl-1,3,4-oxadiazol-2-yl)ethanol, which is the final compound of Example 31, as a starting material was used in the same manner as in Example 3 to obtain the title compound.

$^1$H-NMR (CDCl$_3$, 400 MHz) δ=7. 18-7. 12 (m, 2H), 7. 03-7. 01 (m, 1H), 6. 34-6. 28 (m, 1H), 4. 77-4. 64 (m, 2H), 3. 50-3. 44 (m, 1H), 3. 38-3. 34 (m, 1H), 2. 69-2. 65 (m, 2H), 2.50 (s, 3H), 2. 11-2. 05 (m, 2H), 1. 90-1. 84 (m, 2H).

Example 34: Synthesis of [1-[2-fluoro-5-(5,5,5-trifluoropentyl)phenyl]-2-(5-methyl-1,3,4-oxadiazol-2-yl)ethyl] carbamate

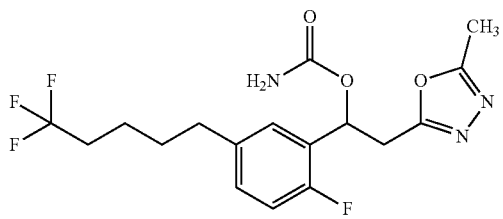 [SMILES: Cc1nnc(CC(OC(N)=O)c2cc(CCCCC(F)(F)F)ccc2F)o1]

1-[2-Fluoro-5-(5,5,5-trifluoropentyl)-phenyl]-2-(5-methyl-1,3,4-oxadiazol-2-yl)ethanol, which is the final compound of Example 32, as a starting material was used in the same manner as in Example 3 to obtain the title compound.

$^1$H-NMR (CDCl$_3$, 400 MHz) δ=7.16 (d, J=5.8 Hz, 1H), 7.09 (d, J=5.0 Hz, 1H), 7. 04-6. 95 (m, 1H), 6.29 (dd, J=4.6, 8.3 Hz, 1H), 4.73 (s, 2H), 3. 55-3. 28 (m, 2H), 2.61 (t, J=7.3 Hz, 2H), 2.50 (s, 3H), 2. 18-2. 03 (m, 2H), 1.64 (dd, J=7.8, 15.9 Hz, 4H).

Example 35: Synthesis of 1-[2-fluoro-5-[3-(1-piperidyl)propoxy]phenyl]-2-(5-methyl-1,3,4-oxadiazol-2-yl)ethanol

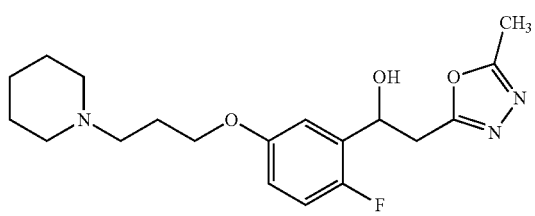 [SMILES: Cc1nnc(CC(O)c2cc(OCCCN3CCCCC3)ccc2F)o1]

The title compound was synthesized in the same manner as in Example 8, except that 2-fluoro-5-hydroxybenzaldehyde was used as a starting material in Example 8-1, and 3-(1-piperidyl)propan-1-ol was used instead of 2,2,3,3-tetrafluoropropanol.

$^1$H-NMR (CDCl$_3$, 400 MHz) δ=7.12 (dd, J=5.8, 3.1 Hz, 1H), 6.95 (t, J=9.3 Hz, 1H), 6.76 (dt, J=8.8, 3.6 Hz, 1H), 5.49 (dd, J=8.8, 3.6 Hz, 1H), 4. 08-4. 00 (m, 2H), 3. 29-3. 15 (m, 2H), 2. 94-2. 77 (m, 6H), 2.52 (s, 3H), 2. 29-2. 20 (m, 2H), 1. 95-1. 83 (m, 4H), 1. 63-1. 54 (m, 2H).

Example 36: Synthesis of 1-[5-[3-(dimethylamino)propoxy]-2-fluoro-phenyl]-2-(5-methyl-1,3,4-oxadiazol-2-yl)ethanol

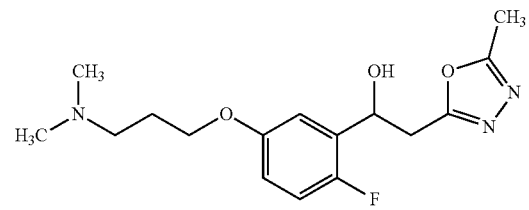 [SMILES: Cc1nnc(CC(O)c2cc(OCCCN(C)C)ccc2F)o1]

The title compound was synthesized in the same manner as in Example 8, except that 2-fluoro-5-hydroxybenzaldehyde was used as the starting material in Example 8-1, and 3-(dimethylamino)propan-1-ol was used instead of 2,2,3,3-tetrafluoropropanol.

$^1$H-NMR (CDCl$_3$, 400 MHz) δ=7.13 (dd, J=5.8, 3.2 Hz, 1H), 6.96 (t, J=9.3 Hz, 1H), 6.77 (dt, J=8.8, 3.6 Hz, 1H), 5.49 (dd, J=8.8, 3.2 Hz, 1H), 4. 09-4. 04 (m, 2H), 3. 29-3. 14 (m, 2H), 3.00 (t, J=3.6 Hz, 2H), 2.67 (s, 6H), 2.52 (s, 3H), 2. 28-2. 21 (m, 2H).

Example 37: Synthesis of 4-fluoro-3-[1-hydroxy-2-(5-methyl-1,3,4-oxadiazol-2-yl)ethyl]-N-(3,3,3-trifluoropropyl)benzamide

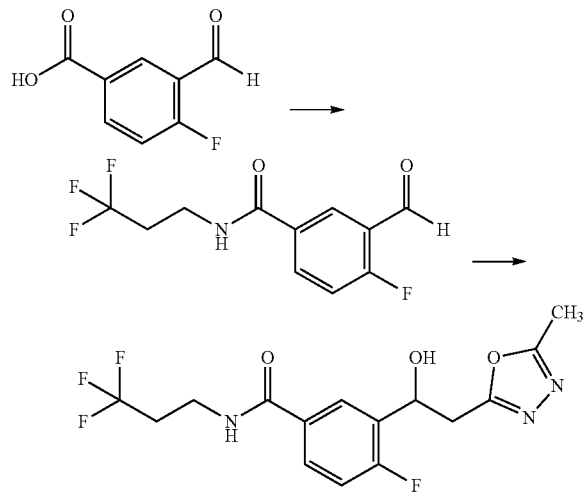

Example 37-1: Synthesis of 4-fluoro-3-formyl-N-(3,3,3-trifluoropropyl)benzamide N,N,N',N'-tetramethyl-O-(benzotriazol-1-yl)uronium tetrafluoroborate (2.3 g, 7.1 mmol) was added to 20 mL of methylene chloride in which 4-fluoro-3-formyl-benzoic acid (1.0 g, 5.9 mmol), N,N-diisopropylethylamine (3.1 mL, 17.8 mmol), and 3,3,3-trifluoropropylamine (0.8 g, 7.1 mmol) were dissolved and stirred at room temperature for 1 hour. The reaction mixture was sequentially washed with saturated aqueous ammonium chloride solution, saturated aqueous sodium bicarbonate solution and saturated aqueous sodium chloride solution once each, and dried over anhydrous magnesium sulfate. Light yellow oil liquid obtained by removing the solvent by evaporation under reduced pressure was purified by flash chromatography to obtain the title compound in light yellow.

Example 37-2: Synthesis of 4-fluoro-3-[1-hydroxy-2-(5-methyl-1,3,4-oxadiazol-2-yl)ethyl]-N-(3,3,3-trifluoropropyl)benzamide To 10 mL of dried tetrahydrofuran in which 2,5-dimethyl-1,3,4-oxadiazole (0.4 g, 3.8 mmol) was dissolved, a temperature was lowered to −78° C., lithium diisopropylamide (1.0 M n-hexane solution, 4.5 mL, 4.5 mmol) was added and stirred for 30 minutes, followed by slowly dropwise addition of 20 mL of dried tetrahydrofuran in which 4-fluoro-3-formyl-N-(3,3,3-trifluoropropyl)benzamide (1.0 g, 3.8 mmol) obtained in Example 37-1 was dissolved while maintaining the temperature. The reaction mixture was slowly raised to room temperature, stirred for 10 hours, washed with saturated ammonium chloride aqueous solution, saturated sodium bicarbonate aqueous solution and saturated sodium chloride aqueous solution sequentially each once, and dried over anhydrous magnesium sulfate. Light yellow oil liquid obtained by removing the solvent by evaporation under reduced pressure was purified by flash chromatography to obtain the title compound as a white solid.

$^1$H-NMR (CDCl$_3$, 400 MHz) δ=8.06 (d, J=2.5 Hz, 1H), 8.05-7.84 (m, 1H), 7.14 (t, J=12.0 Hz, 1H), 7.00 (brs, 1H, NH), 5.54 (m, 1H), 4.44 (d, J=8.0 Hz, 1H), 3.75-3.70 (m, 2H), 3.30 (dd, J1=20.0 Hz, J2=4.0 Hz, 1H), 3.20 (dd, J1=20.0 Hz, J2=11.5 Hz, 1H), 2.55 (s, 3H), 2.50 (m, 2H).

Example 38: Synthesis of [1-[2-fluoro-5-(3,3,3-trifluoropropylcarbamoyl)phenyl]-2-(5-methyl-1,3,4-oxadiazol-2-yl)ethyl] carbamate

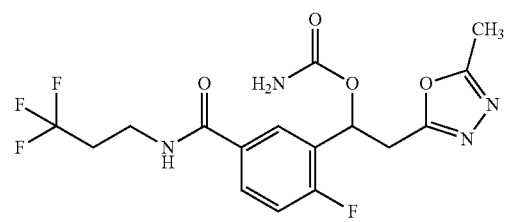 [SMILES: Cc1nnc(CC(OC(N)=O)c2cc(C(=O)NCCC(F)(F)F)ccc2F)o1]

4-Fluoro-3-[1-hydroxy-2-(5-methyl-1,3,4-oxadiazol-2-yl)ethyl]-N-(3,3,3-trifluoropropyl)benzamide, which is the final compound of Example 37, as a starting material was used in the same manner as in Example 3 to obtain the title compound.

$^1$H-NMR (CDCl$_3$, 400 MHz) δ=7.86 (d, J=3.0 Hz, 1H), 7.86-7.71 (m, 1H), 7.12 (t, J=10.5 Hz, 1H), 6.74 (brs, 1H, NH), 6.31 (dd, J1=10.0 Hz, J2=6.5 Hz, 1H) 5.0 (brs, 2H, NH2), 3.68 (dd, J1=16.0 Hz, J2=8.0 Hz, 2H), 3.45 (dd, J1=19.0 Hz, J2=10.0 Hz, 1H), 3.33 (dd, J1=19.0 Hz, J2=6.5 Hz, 1H), 2.50-2.44 (m, 5H).

Example 39: Synthesis of 1-[2-chloro-5-(4,4,4-trifluorobutoxy)phenyl]-2-(5-methyl-1,3,4-oxadiazol-2-yl)ethanol

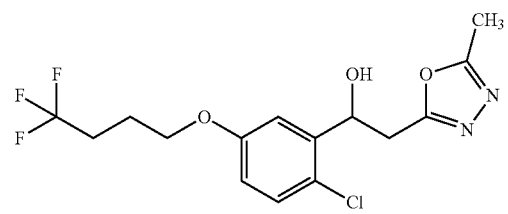 [SMILES: Cc1nnc(CC(O)c2cc(OCCCC(F)(F)F)ccc2Cl)o1]

The title compound was synthesized in the same manner as in Example 8, except that 2-chloro-5-hydroxybenzaldehyde was used as a starting material in Example 8-1 and 4,4,4-trifluorobutanol was used instead of 2,2,3,3-tetrafluoropropanol.

$^1$H-NMR (CDCl$_3$, 400 MHz) δ=7.25 (d, J=8.8 Hz, 1H), 7.22 (d, J=3.0 Hz, 1H), 6.79 (dd, J=8.8, 3.0 Hz, 1H), 5.55 (dt, J=9.4, 3.2 Hz, 1H), 4.05-3.99 (m, 2H), 3.58 (d, J=3.6 Hz, 1H), 3.35-3.29 (m, 1H), 3.08-3.01 (m, 1H), 2.53 (s, 3H), 2.35-2.28 (m, 2H), 2.09-2.02 (m, 2H).

Example 40: Synthesis of [1-[5-[3-(dimethylamino)propoxy]-2-fluoro-phenyl]-2-(5-methyl-1,3,4-oxadiazol-2-yl)ethyl] carbamate

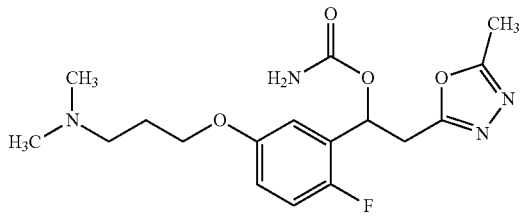 [SMILES: Cc1nnc(CC(OC(N)=O)c2cc(OCCCN(C)C)ccc2F)o1]

1-[5-[3-(Dimethylamino)propoxy]-2-fluoro-phenyl]-2-(5-methyl-1,3,4-oxadiazol-2-yl)ethanol, which is the final compound of Example 36, as a starting material was used in the same manner as in Example 3 to obtain the title compound.

$^1$H-NMR (CDCl$_3$, 400 MHz) δ=6.97 (t, J=9.6 Hz, 1H), 6.89 (dd, J=5.6, 3.2 Hz, 1H), 6.80 (dt, J=8.8, 3.6 Hz, 1H), 6.27 (dd, J=8.4, 4.8 Hz, 1H), 4.74 (brs, 2H, NH2), 3.97 (t, J=6.6 Hz, 2H), 3. 47-3. 29 (m, 2H), 2. 53-2. 47 (m, 2H), 2.50 (s, 3H), 2.29 (s, 6H), 1. 98-1. 94 (m, 2H).

Example 41: Synthesis of [1-[2-chloro-5-(4,4,4-trifluorobutoxy)phenyl]-2-(5-methyl-1,3,4-oxadiazol-2-yl)ethyl] carbamate

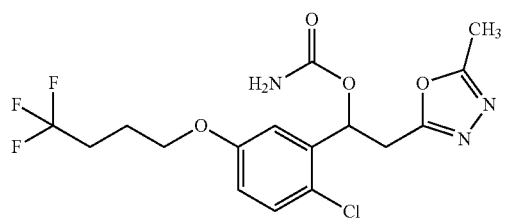 [SMILES: Cc1nnc(CC(OC(N)=O)c2cc(OCCCC(F)(F)F)ccc2Cl)o1]

1-[2-Chloro-5-(4,4,4-trifluorobutoxy)phenyl]-2-(5-methyl-1,3,4-oxadiazol-2-yl)ethanol, which is the final compound of Example 39, as a starting material was used in the same manner as in Example 3 to obtain the title compound.

$^1$H-NMR (CDCl$_3$, 400 MHz) δ=7.28 (d, J=8.8 Hz, 1H), 6.94 (d, J=3.0 Hz, 1H), 6.78 (dd, J=8.8, 3.0 Hz, 1H), 6.34 (dd, J=7.4, 5.3 Hz, 1H), 4.77 (brs, 2H, NH2), 3.98 (t, J=5.8 Hz, 2H), 3. 36-3. 33 (m, 2H), 2.51 (s, 3H), 2. 37-2. 25 (m, 2H), 2. 09-2. 01 (m, 2H).

Example 42: Synthesis of 2-(5-methyl-1,3,4-oxadiazol-2-yl)-1-[2-methyl-5-[4-(trifluoromethyl)phenyl]phenyl]ethanol

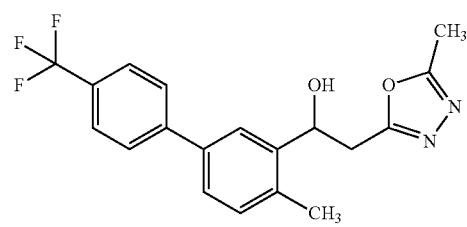 [SMILES: Cc1nnc(CC(O)c2cc(-c3ccc(C(F)(F)F)cc3)ccc2C)o1]

The title compound was synthesized in the same manner as in Example 1, except that 5-bromo-2-methyl-benzaldehyde was used as a starting material in Example 1-1 and 4-trifluoromethylboronic acid was used instead of 4-chlorophenylboronic acid in Example 1-2.

$^1$H-NMR (DMSO, 400 MHz) δ=7.88 (d, J=8.0 Hz, 2H), 7. 85-7. 84 (m, 1H), 7.82 (d, J=8.0 Hz, 2H), 7.56 (dd, J=1.6, 8.0 Hz, 1H), 7.30 (d, J=8.0 Hz, 1H), 5.66 (d, J=4.8 Hz, 1H), 5. 26-5. 22 (m, 1H), 3. 18-3. 14 (m, 2H), 2.46 (s, 3H), 2.37 (s, 3H).

Example 43: Synthesis of 1-[2-methoxy-5-[4-(trifluoromethyl)phenyl]phenyl]-2-(5-methyl-1,3,4-oxadiazol-2-yl)ethanol

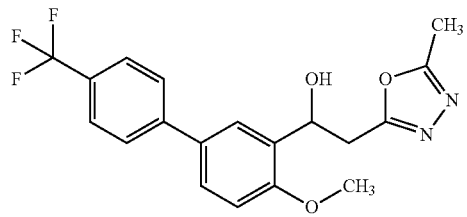 [SMILES: COc1ccc(-c2ccc(C(F)(F)F)cc2)cc1C(O)Cc1nnc(C)o1]

The title compound was synthesized in the same manner as in Example 1, except that 5-bromo-2-methoxy-benzaldehyde was used as a starting material in Example 1-1 and 4-trifluoromethylboronic acid was used instead of 4-chlorophenylboronic acid in Example 1-2.

$^1$H-NMR (DMSO, 400 MHz) δ=7. 86-7. 79 (m, 5H), 7.67 (dd, J=2.4, 8.4 Hz, 1H), 7.12 (d, J=8.4 Hz, 1H), 5.63 (d, J=5.2 Hz, 1H), 5. 33-5. 29 (m, 1H), 3.84 (s, 3H), 3. 18-3. 14 (m, 2H), 2.47 (s, 3H).

Example 44: Synthesis of [2-(5-methyl-1,3,4-oxadiazol-2-yl)-1-[2-methyl-5-[4-(trifluoromethyl)phenyl]phenyl]ethyl] carbamate

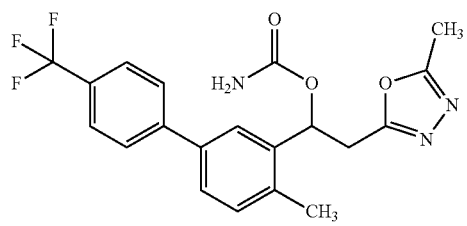 [SMILES: Cc1nnc(CC(OC(N)=O)c2cc(-c3ccc(C(F)(F)F)cc3)ccc2C)o1]

2-(5-methyl-1,3,4-oxadiazol-2-yl)-1-[2-methyl-5-[4-(trifluoromethyl)phenyl]phenyl]ethanol, which is the final compound of Example 42, as a starting material was used in the same manner as in Example 3 to obtain the title compound.

$^1$H-NMR (CDCl$_3$, 400 MHz) δ=7. 70-7. 63 (m, 4H), 7.59 (d, J=1.6 Hz, 1H), 7.45 (dd, J=2.0, 8.0 Hz, 1H), 7. 28-7. 26 (m, 1H), 6. 32-6. 29 (m, 1H), 4.72 (brs, 2H, NH2), 3. 48-3. 24 (m, 2H), 2.50 (s, 3H), 2.49 (s, 3H).

Example 45: Synthesis of [1-[2-methoxy-5-[4-(trifluoromethyl)phenyl]phenyl]-2-(5-methyl-1,3,4-oxadiazol-2-yl)ethyl] carbamate

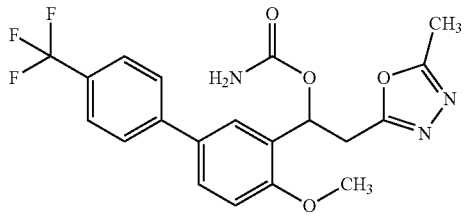 [SMILES: COc1ccc(-c2ccc(C(F)(F)F)cc2)cc1C(Cc1nnc(C)o1)OC(N)=O]

1-[2-Methoxy-5-[4-(trifluoromethyl)phenyl]phenyl]-2-(5-methyl-1,3,4-oxadiazol-2-yl) ethanol, which is the final compound of Example 43, as a starting material was used in the same manner as in Example 3 to obtain the title compound.

$^1$H-NMR (CDCl$_3$, 400 MHz) δ=7. 50-7. 67 (m, 6H), 6.98 (d, J=8.4 Hz, 1H), 6.42 (dd, J=5.2, 7.6 Hz, 1H), 4.84 (brs, 2H, NH2), 3.92 (s, 3H), 3. 38-3. 37 (m, 2H), 2.51 (s, 3H).

Example 46: Synthesis of 1-[2-methyl-5-[4-(trifluoromethyl)phenyl]phenyl]-2-(1,3,4-oxadiazol-2-yl)ethanol

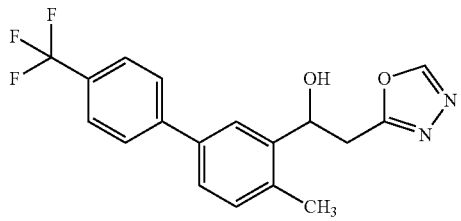 [SMILES: Cc1ccc(-c2ccc(C(F)(F)F)cc2)cc1C(O)Cc1nnco1]

The title compound was synthesized in the same manner as in Example 1, except that 5-bromo-2-methyl-benzaldehyde was used as a starting material in Example 1-1, 4-trifluoromethylboronic acid was used instead of 4-chlorophenylboronic acid in Example 1-2, and N,N'-dimethylformamide dimethylacetal was used instead of N,N'-dimethylacetamide dimethylacetal in Example 1-4.

$^1$H-NMR (CDCl$_3$, 400 MHz) δ=8.37 (s, 1H), 7.82 (d, J=2.0 Hz, 1H), 7. 70-7. 65 (m, 4H), 7.46 (dd, J=2.0, 8.0 Hz, 1H), 7.26 (d, J=7.2 Hz, 1H), 5. 56-5. 54 (m, 1H), 3. 47-3. 21 (m, 3H), 2.14 (s, 3H).

Example 47: Synthesis of 1-[2-methoxy-5-[4-(trifluoromethyl)phenyl]phenyl]-2-(1,3,4-oxadiazol-2-yl)ethanol

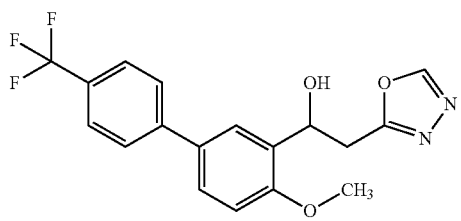 [SMILES: COc1ccc(-c2ccc(C(F)(F)F)cc2)cc1C(O)Cc1nnco1]

The title compound was synthesized in the same manner as in Example 1, except that 5-bromo-2-methoxy-benzaldehyde was used as a starting material in Example 1-1, 4-trifluoromethylboronic acid was used instead of 4-chlorophenylboronic acid in Example 1-2, and N,N'-dimethylformamide dimethylacetal was used instead of N,N'-dimethylacetamide dimethylacetal in Example 1-4.

$^1$H-NMR (CDCl$_3$, 400 MHz) δ=8.37 (s, 1H), 7.72 (d, J=2.4 Hz, 1H), 7. 68-7. 63 (m, 4H), 7.53 (dd, J=2.4, 8.4 Hz, 1H), 6.99 (d, J=8.8 Hz, 1H), 5. 53-5. 52 (m, 1H), 3.92 (s, 3H), 3. 54-3. 29 (m, 3H).

Example 48: Synthesis of 1-[2-chloro-5-[4-(trifluoromethyl)phenyl]phenyl]-2-(5-methyl-1,3,4-oxadiazol-2-yl)ethanol

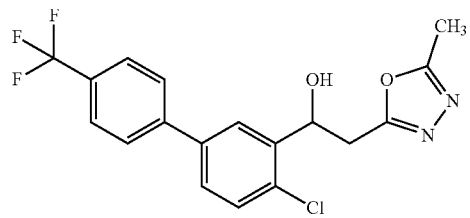 [SMILES: Cc1nnc(CC(O)c2cc(-c3ccc(C(F)(F)F)cc3)ccc2Cl)o1]

The title compound was synthesized in the same manner as in Example 1, except that 5-bromo-2-chloro-benzaldehyde was used as a starting material in Example 1-1, and 4-trifluoromethylboronic acid was used instead of 4-chlorophenylboronic acid in Example 1-2.

$^1$H-NMR (CDCl$_3$, 400 MHz) δ=7.94 (d, J=2.0 Hz, 1H), 7.70 (s, 4H), 7. 51-7. 45 (m, 2H), 5.67 (dt, J=9.2, 3.2 Hz, 1H), 3.75 (d, J=3.9 Hz, 1H), 3. 41-3. 36 (m, 1H), 3. 15-3. 08 (m, 1H), 2.54 (s, 3H).

Example 49: Synthesis of 1-[2-chloro-5-[4-(trifluoromethyl)phenyl]phenyl]-2-(1,3,4-oxadiazol-2-yl)ethanol

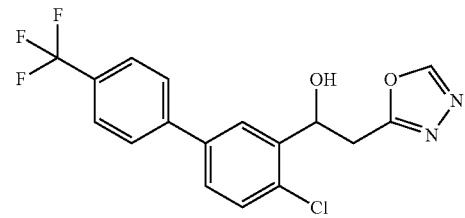

The title compound was synthesized in the same manner as in Example 1, except that 5-bromo-2-chloro-benzaldehyde was used as a starting material in Example 1-1, 4-trifluoromethylboronic acid was used instead of 4-chlorophenylboronic acid in Example 1-2, and N,N'-dimethylformamide dimethylacetal was used instead of N,N'-dimethylacetamide dimethylacetal in Example 1-4.

$^1$H-NMR (CDCl$_3$, 400 MHz) δ=8.41 (s, 1H), 7.93 (s, 1H), 7.70 (d, J=2.0 Hz, 4H), 7. 50-7. 46 (m, 2H), 5.71 (dt, J=9.5, 2.9 Hz, 1H), 3.52 (d, J=3.9 Hz, 1H), 3. 50-3. 45 (m, 1H), 3. 26-3. 19 (m, 1H).

Example 50: Synthesis of [1-[2-chloro-5-[4-(trifluoromethyl)phenyl]phenyl]-2-(5-methyl-1,3,4-oxadiazol-2-yl)ethyl] carbamate

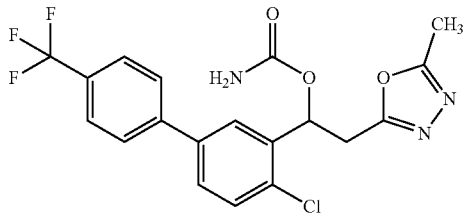 [SMILES: Cc1nnc(CC(OC(N)=O)c2cc(-c3ccc(C(F)(F)F)cc3)ccc2Cl)o1]

1-[2-Chloro-5-[4-(trifluoromethyl)phenyl]phenyl]-2-(5-methyl-1,3,4-oxadiazol-2-yl)ethanol, which is the final compound of Example 48, as a starting material was used in the same manner as in Example 3 to obtain the title compound.
¹H-NMR (CDCl₃, 400 MHz) δ=7. 72-7. 70 (m, 2H), 7. 64-7. 61 (m, 3H), 7.49 (s, 2H), 6.45 (dd, J=7.4, 5.4 Hz, 1H), 4.80 (brs, 2H, NH2), 3. 43-3. 41 (m, 2H), 2.51 (s, 3H).

Example 51: Synthesis of [1-[2-chloro-5-[4-(trifluoromethyl)phenyl]phenyl]-2-(1,3,4-oxadiazol-2-yl)ethyl]carbamate

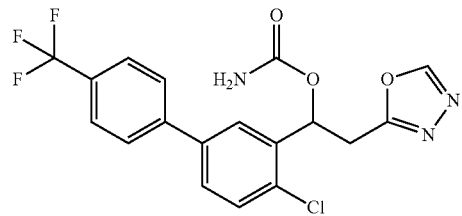 [SMILES: NC(=O)OC(Cc1nnco1)c1cc(-c2ccc(C(F)(F)F)cc2)ccc1Cl]

1-[2-Chloro-5-[4-(trifluoromethyl)phenyl]phenyl]-2-(1,3,4-oxadiazol-2-yl)ethanol, which is the final compound of Example 49, as a starting material was used in the same manner as in Example 3 to obtain the title compound.
¹H-NMR (CDCl₃, 400 MHz) δ=8.38 (s, 1H), 7. 72-7. 70 (m, 2H), 7. 63-7. 60 (m, 3H), 7. 50-7. 49 (m, 2H), 6.49 (dd, J=6.9, 5.4 Hz, 1H), 4.78 (brs, 2H, NH2), 3. 53-3. 51 (m, 2H).

Example 52: Synthesis of 2-(1,3,4-oxadiazol-2-yl)-1-[3-[4-(trifluoromethyl)phenyl]phenyl]ethanol

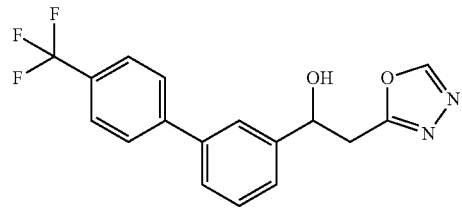 [SMILES: OC(Cc1nnco1)c1cccc(-c2ccc(C(F)(F)F)cc2)c1]

The title compound was synthesized in the same manner as in Example 1, except that 3-bromobenzaldehyde was used as a starting material in Example 1-1, 4-trifluoromethylboronic acid was used instead of 4-chlorophenylboronic acid in Example 1-2, and N,N'-dimethylformamide dimethylacetal was used instead of N,N'-dimethylacetamide dimethylacetal in Example 1-4.

¹H-NMR (CDCl₃, 400 MHz) δ=8.39 (s, 1H), 7.7 (d, J=19.6 Hz, 4H), 7.53 (d, J=15.6 Hz, 1H), 7.48 (s, 1H), 7.46 (d, J=7.6 Hz, 2H), 5.39 (dd, J1=4, 8.4 Hz, 1H), 3. 25-3. 37 (m, 3H).

Example 53: Synthesis of 2-(5-ethyl-1,3,4-oxadiazol-2-yl)-1-[3-[4-(trifluoromethyl)phenyl]phenyl]ethanol

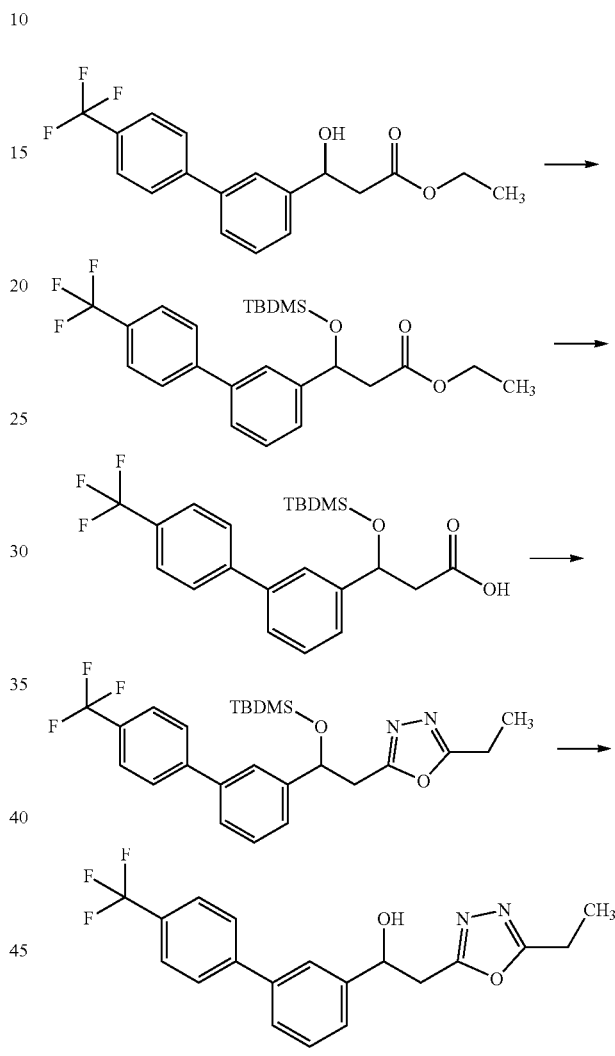

Example 53-1: Synthesis of ethyl 3-[tert-butyl(dimethyl)silyl]oxy-3-[3-[4-(trifluoromethyl)phenyl]phenyl]propanoate Imidazole (0.5 g, 7.7 mmol) and tert-butyldimethylsilyl chloride (1.1 g, 7.7 mmol) were sequentially added to 20 mL of methylene chloride containing ethyl 3-hydroxy-3-[3-[4-(trifluoromethyl)phenyl]phenyl]propanoate (1.3 g, 3.8 mmol) obtained in Example 1-2 by the use of 4-trifluoromethyl boronic acid instead of 4-chlorophenylboronic acid, and the mixture was stirred at room temperature for one day. 100 mL of ethyl acetate was added to the reaction mixture, and the reaction mixture was sequentially washed with saturated ammonium chloride aqueous solution, saturated sodium bicarbonate aqueous solution, and saturated sodium chloride aqueous solution, and then the organic layer was dried over anhydrous magnesium sulfate. The yellow oil liquid obtained by removing the solvent by evaporation under reduced pressure was purified by flash chromatography to obtain the title compound as light yellow liquid.

Example 53-2: Synthesis of 3-[tert-butyl(dimethyl)silyl]oxy-3-[3-[4-(trifluoromethyl)phenyl]phenyl]propanoic acid 2N sodium hydroxide aqueous solution (1.1 mL, 5.7 mmol) was added to 20 mL of ethanol dissolved with ethyl 3-[tert-butyl(dimethyl)silyl]oxy-3-[3-[4-(trifluoromethyl)phenyl]phenyl]propanoate (1.3 g, 2.9 mmol) obtained in Example 53-1, and the mixture was stirred at room temperature for 5 hours. The reaction mixture was adjusted to pH 2 with 1N aqueous hydrochloric acid solution, extracted with 100 mL of ethyl acetate, and dried over anhydrous magnesium sulfate. The solvent was removed by evaporation under reduced pressure to obtain the title compound as a white solid.

Example 53-3: Synthesis of tert-butyl-[2-(5-ethyl-1,3,4-oxadiazol-2-yl)-1-[3-[4-(trifluoromethyl)phenyl]phenyl]ethoxy]-dimethyl-silane 1,1'-carbonyldiimidazole (0.1 g, 1.0 mmol) was added to 20 mL of methylene chloride solution containing 3-[tert-butyl(dimethyl)silyl]oxy-3-[3-[4-(trifluoromethyl)phenyl]phenyl]propanoic acid (0.4 g, 1.0 mmol) obtained in Example 53-2, and the mixture was stirred at room temperature for 30 minutes. Propanoic hydrazide (88 mg, 1.0 mmol) was added to the reaction mixture and stirred for 1 hour at the same temperature, and carbon tetrabromide (663 mg, 2.0 mmol) and triphenylphosphine (525 mg, 2 mmol) were sequentially added thereto, followed by stirring for 2 hours. 100 mL of ethyl acetate was added to the reaction mixture, and the reaction mixture was sequentially washed with saturated ammonium chloride aqueous solution, saturated sodium bicarbonate aqueous solution and saturated sodium chloride aqueous solution, and then the organic layer was dried over anhydrous magnesium sulfate. A yellow liquid obtained by removing the solvent by vacuum evaporation was purified by flash chromatography to obtain the title compound in pale yellow.

Example 53-4: Synthesis of 2-(5-ethyl-1,3,4-oxadiazol-2-yl)-1-[3-[4-(trifluoromethyl)phenyl]phenyl]ethanol Tetra-N-butylammonium fluoride (0.1 mL, 0.3 mmol) was slowly added to 10 mL of tetrahydrofuran containing tert-butyl-[2-(5-ethyl-1,3,4-oxadiazol-2-yl)-1-[3-[4-(trifluoromethyl)phenyl]ethoxy]-dimethyl-silane (70 mg, 0.2 mmol) obtained in Example 53-3 while maintaining the temperature at 0° C. under ice bath. The reaction mixture was stirred at the same temperature for 1 hour, 20 mL of ethyl acetate was added thereto, washed with saturated aqueous ammonium chloride solution, saturated aqueous sodium bicarbonate solution and saturated aqueous sodium chloride solution, and dried over anhydrous magnesium sulfate. Light brown oil liquid obtained by removing the solvent by evaporation under reduced pressure was purified by flash chromatography to obtain the title compound as white solid.

$^1$H-NMR (CDCl$_3$, 400 MHz) δ=7.7 (d, J=19.6 Hz, 4H), 7.56 (d, J=7.2 Hz, 2H), 7. 44-7. 51 (m, 2H), 5.39 (dd, J=4.8, 8 Hz, 1H), 3.39 (s, 1H), 3. 28-3. 26 (m, 2H), 2.86 (q, J=7.6 Hz, 2H), 1.36 (t, J=7.6 Hz, 3H).

Example 54: Synthesis of 2-(5-tert-butyl-1,3,4-oxadiazol-2-yl)-1-[3-[4-(trifluoromethyl)phenyl]phenyl]ethanol

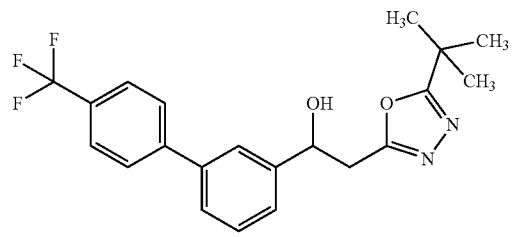 [SMILES: CC(C)(C)c1nnc(CC(O)c2cccc(-c3ccc(C(F)(F)F)cc3)c2)o1]

The title compound was synthesized in the same manner as Example 53, except that 2,2-dimethylpropanhydrazide was used instead of propanobrohydrazide in Example 53-3.

$^1$H-NMR (CDCl$_3$, 400 MHz) δ=7.7 (d, J=19.6 Hz, 4H), 7.54 (d, J=7.6 Hz, 2H), 7. 44-7. 50 (m, 2H), 5.35 (dd, J1=8.8 Hz J2=4.8 Hz, 1H), 3.44 (s, 1H), 3. 22-3. 33 (m, 2H).

Example 55: Synthesis of [2-(5-methyl-1,3,4-oxadiazol-2-yl)-1-[3-[4-(trifluoromethyl)phenyl]phenyl]ethyl]acetate

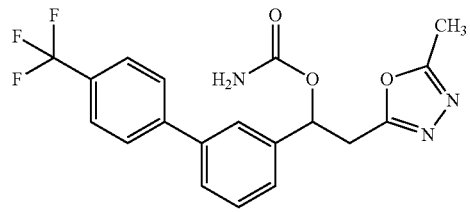 [SMILES: Cc1nnc(CC(OC(N)=O)c2cccc(-c3ccc(C(F)(F)F)cc3)c2)o1]

As a starting material, acetyl chloride (0.3 g, 4.35 mmol) was added to 20 mL of methylene chloride dissolved with 2-(5-methyl-1,3,4-oxadiazol-2-yl)-1-[3-[4-(trifluoromethyl)phenyl]phenyl]ethanol (1.0 g, 2.9 mmol) which is the final compound of Example 6 and triethylamine (1.1 mL, 8.6 mmol), and the resulting solution was stirred at room temperature for about 6 hours. The reaction mixture was washed with saturated aqueous sodium bicarbonate solution and saturated aqueous sodium chloride solution once each, and dried over anhydrous magnesium sulfate. Light yellow oil liquid obtained by removing the solvent by evaporation under reduced pressure was purified by flash chromatography to obtain the title compound.

$^1$H-NMR (CDCl$_3$, 400 MHz) δ=7. 72-7. 65 (m, 4H), 7. 55-7. 46 (m, 3H), 7. 42-7. 40 (m, 1H), 6. 26-6. 23 (m, 1H), 3.53 (dd, J=15.6, J=8.8, 1H), 3.35 (dd, J=15.6, J=5.2, 1H), 2.50 (s, 3H), 2.08 (s, 3H).

Example 56: Synthesis of 2-[2-methoxy-2-[3-[4-(trifluoromethyl)phenyl]phenyl]ethyl]-5-methyl-1,3,4-oxadiazole

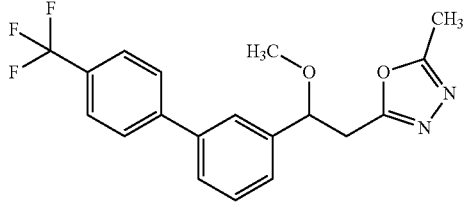 [SMILES: COC(Cc1nnc(C)o1)c1cccc(-c2ccc(C(F)(F)F)cc2)c1]

2-(5-Methyl-1,3,4-oxadiazol-2-yl)-1-[3-[4-(trifluoromethyl)phenyl]phenyl]ethanol (1.0 g, 2.9 mmol), which is the final compound of Example 6, and iodomethane (0.8 g, 5.8 mmol) were sequentially added to 20 mL of tetrahydrofuran containing sodium hydride (60% dispersion in mineral oil, 0.2 g, 5.8 mmol) as starting materials, and heated and refluxed for about 1 hour. The temperature was lowered to room temperature, and the reaction mixture was dissolved in 100 mL of ethyl acetate, washed with saturated aqueous sodium bicarbonate solution and saturated aqueous sodium chloride solution once each, and the organic layer was dried over anhydrous magnesium sulfate. Light yellow oil liquid obtained by removing the solvent by evaporation under reduced pressure was purified by flash chromatography to obtain the title compound.

$^1$H-NMR (CDCl$_3$, 400 MHz) δ=7. 72-7. 67 (m, 4H), 7. 55-7. 47 (m, 3H), 7. 39-7. 37 (m, 1H), 4. 75-4. 72 (m, 1H), 3.36 (dd, J=15.6, J=8.8, 1H), 3.27 (s, 3H), 3.18 (dd, J=15.6, J=4.8, 1H), 2.50 (s, 3H).

Example 57: Synthesis of 1-[3-(4-fluorophenyl)phenyl]-2-(5-methyl-1,3,4-oxadiazol-2-yl)ethanol

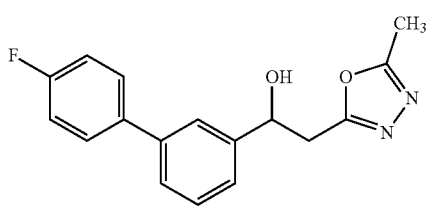 [SMILES: Cc1nnc(CC(O)c2cccc(-c3ccc(F)cc3)c2)o1]

The title compound was synthesized in the same manner as in Example 1, except that 3-bromobenzaldehyde was used as the starting material and 4-fluorophenylboronic acid was used instead of 4-chlorophenylboronic acid in Example 1-2.

$^1$H-NMR (CDCl$_3$, 400 MHz) δ=7.60 (s, 1H), 7. 53-7. 57 (m, 2H), 7. 38-7. 51 (m, 3H), 5.33 (dd, J1=8.4 Hz J2=4 Hz, 1H), 3. 23-3. 27 (m, 3H), 2.50 (s, 3H).

Example 58: Synthesis of 1-[3-(3,4-difluorophenyl)phenyl]-2-(5-methyl-1,3,4-oxadiazol-2-yl)ethanol

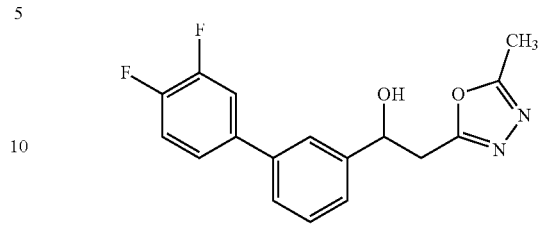

The title compound was synthesized in the same manner as in Example 1, except that 3-bromobenzaldehyde was used as a starting material and 3,4-difluorophenyl boronic acid was used instead of 4-chlorophenylboronic acid in Example 1-2.

$^1$H-NMR (CDCl$_3$, 400 MHz) δ=7.60 (s, 1H), 7. 39-7. 47 (m, 4H), 7. 22-7. 39 (m, 1H), 5.33 (dd, J1=8.4 Hz J2=4.4 Hz, 1H), 3.32 (d, J=4 Hz, 1H), 3.25 (d, J=7.6 Hz, 2H), 2.50 (s, 3H).

Example 59: Synthesis of 2-(5-methyl-1,3,4-oxadiazol-2-yl)-1-[3-[4-(trifluoromethoxy)phenyl]phenyl]ethanol

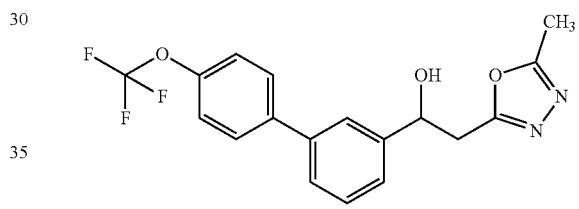

The title compound was synthesized in the same manner as in Example 1, except that 3-bromobenzaldehyde was used as a starting material and 4-trifluoromethoxyphenylboronic acid was used instead of 4-chlorophenylboronic acid in Example 1-2.

$^1$H-NMR (CDCl$_3$, 400 MHz) δ=7. 59-7. 63 (m, 3H), 7. 43-7. 51 (m, 3H), 7.3 (d, J=8.4 Hz, 2H), 5.33 (dd, J1=8.4 Hz J2=4 Hz, 1H), 3.26 (m, 3H), 2.50 (s, 3H).

Example 60: Synthesis of 1-[3-(2-methoxy-4-(trifluoromethoxy)phenyl)phenyl]-2-(5-methyl-1,3,4-oxadiazol-2-yl)ethanol

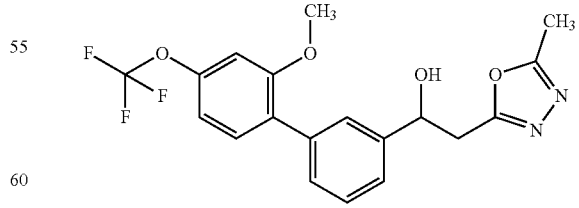

The title compound was synthesized in the same manner as in Example 1, except that 3-bromobenzaldehyde was used as a starting material and 2-methoxy-4-trifluoromethoxyphenylboronic acid was used instead of 4-chlorophenylboronic acid in Example 1-2.

¹H-NMR (CDCl₃, 400 MHz) δ=7. 53-7. 29 (m, 5H), 6.90 (d, J=8.4 Hz, 1H), 6.82 (s, 1H), 5. 31-5. 27 (m, 1H), 3.81 (s, 3H), 3. 30-3. 18 (m, 3H), 2.51 (s, 3H).

Example 61: Synthesis of 1-[3-(4-chloro-2-(trifluoromethyl)phenyl)phenyl]-2-(5-methyl-1,3,4-oxadiazol-2-yl)ethanol

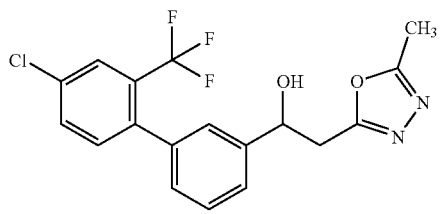 [SMILES: Cc1nnc(CC(O)c2cccc(-c3ccc(Cl)cc3C(F)(F)F)c2)o1]

The title compound was synthesized in the same manner as in Example 1, except that 3-bromobenzaldehyde was used as a starting material and 4-chloro-2-trifluoromethylphenyl boronic acid was used instead of 4-chlorophenylboronic acid in Example 1-2.

¹H-NMR (CDCl₃, 400 MHz) δ=7.73 (s, 1H), 7. 55-7. 23 (m, 6H), 5. 30-5. 28 (m, 1H), 3.49 (d, J=3.2 Hz, 1H), 3. 28-3. 17 (m, 2H), 2.49 (s, 3H).

Example 62: Synthesis of 1-[3-(4-chloro-2-methoxy-phenyl)phenyl]-2-(5-methyl-1,3,4-oxadiazol-2-yl)ethanol

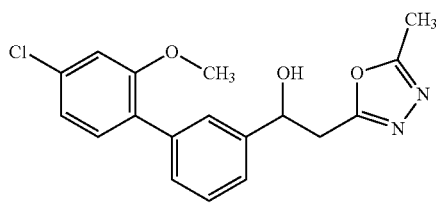 [SMILES: COc1cc(Cl)ccc1-c1cccc(C(O)Cc2nnc(C)o2)c1]

The title compound was synthesized in the same manner as in Example 1, except that 3-bromobenzaldehyde was used as a starting material and 4-chloro-2-methoxyphenylboronic acid was used instead of 4-chlorophenylboronic acid in Example 1-2.

¹H-NMR (CDCl₃, 400 MHz) δ=7. 59-6. 96 (m, 7H), 5. 29-5. 25 (m, 1H), 3.79 (s, 3H), 3.47 (d, J=3.6 Hz, 1H), 3. 29-3. 16 (m, 2H), 2.49 (s, 3H).

Example 63: Synthesis of 1-[3-(2-chlorophenyl)phenyl]-2-(5-methyl-1,3,4-oxadiazol-2-yl)ethanol

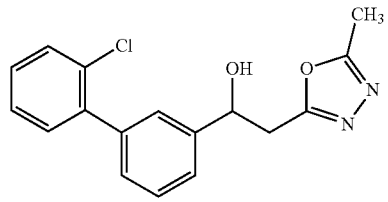 [SMILES: Cc1nnc(CC(O)c2cccc(-c3ccccc3Cl)c2)o1]

The title compound was synthesized in the same manner as in Example 1, except that 3-bromobenzaldehyde was used as a starting material and 2-chlorophenylboronic acid was used instead of 4-chlorophenylboronic acid in Example 1-2.

¹H-NMR (CDCl₃, 400 MHz) δ=7. 50-7. 45 (m, 4H), 7. 42-7. 41 (m, 1H), 7. 34-7. 29 (m, 3H), 5. 34-5. 30 (m, 1H), 3.27 (d, J=10.5 Hz, 1H), 3.25 (d, J=5.5 Hz, 1H), 3.18 (d, J=4.5 Hz, 1H), 2.52 (s, 3H).

Example 64: Synthesis of 1-[3-(3-chlorophenyl)phenyl]-2-(5-methyl-1,3,4-oxadiazol-2-yl)ethanol

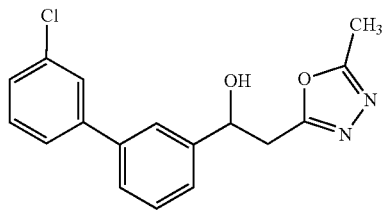 [SMILES: Cc1nnc(CC(O)c2cccc(-c3cccc(Cl)c3)c2)o1]

The title compound was synthesized in the same manner as in Example 1, except that 3-bromobenzaldehyde was used as a starting material and 3-chlorophenylboronic acid was used instead of 4-chlorophenylboronic acid in Example 1-2.

¹H-NMR (CDCl₃, 400 MHz) δ=7. 67-7. 63 (m, 1H), 7. 58-7. 52 (m, 2H), 7. 48-7. 44 (m, 3H), 7. 42-7. 33 (m, 2H), 5. 36-5. 32 (m, 1H), 3. 27-3. 24 (m, 3H), 2.53 (s, 3H).

Example 65: Synthesis of 1-[3-(4-chlorophenyl)phenyl]-2-(5-methyl-1,3,4-oxadiazol-2-yl)ethanol

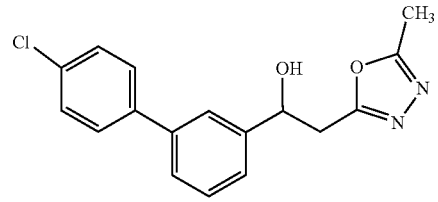 [SMILES: Cc1nnc(CC(O)c2cccc(-c3ccc(Cl)cc3)c2)o1]

3-Bromobenzaldehyde as a starting material was used in the same manner as in Example 1 to obtain the title compound.

¹H-NMR (CDCl₃, 400 MHz) δ=7. 70-7. 62 (m, 2H), 7. 53-7. 51 (m, 3H), 7. 48-7. 41 (m, 3H), 5. 34-5. 32 (m, 1H), 3. 27-3. 23 (m, 3H), 2.53 (s, 3H).

Example 66: Synthesis of 2-fluoro-2-(5-methyl-1,3,4-oxadiazol-2-yl)-1-[3-(4,4,4-trifluorobutoxy)phenyl]ethanol

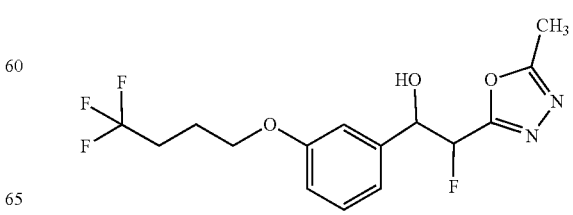

The title compound was synthesized in the same manner as in Example 8, except that 4,4,4-trifluorobutanol was used instead of 2, 2, 3, 3-tetrafluoropropanol in Example 8-1, and ethyl 2-bromo-2-fluoroacetate was used instead of ethyl iodoacetate in Example 8-2.

$^1$H-NMR (CDCl$_3$, 400 MHz) δ=7. 33-7. 22 (m, 1H), 7. 03-6. 83 (m, 3H), 5. 71-5. 51 (m, 1H), 5. 34-5. 27 (m, 1H), 4. 04-3. 98 (m, 2H), 3. 10-3. 09 (m, 1H), 2. 59-2. 55 (m, 3H), 2. 36-2. 26 (m, 2H), 2. 09-2. 02 (m, 2H).

Example 67: Synthesis of 2-(5-methyl-1,3,4-oxadiazol-2-yl)-1-[3-(4,4,4-trifluorobutoxy)phenyl]propan-1-ol

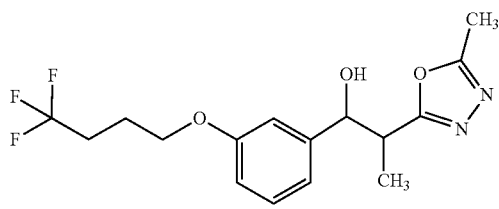 [SMILES: Cc1nnc(C(C)C(O)c2cccc(OCCCC(F)(F)F)c2)o1]

The title compound was synthesized in the same manner as in Example 8, except that 4,4,4-trifluorobutanol was used instead of 2,2,3,3-tetrafluoropropanol in Example 8-1, and ethyl 2-bromo-2-methylacetate was used instead of ethyl iodoacetate in Example 8-2.

$^1$H-NMR (CDCl$_3$, 400 MHz) δ=7.28 (t, J=7.7 Hz, 1H), 6. 96-6. 92 (m, 2H), 6.85 (d, J=7.9 Hz, 1H), 4.86 (dd, J=8.3, 4.0 Hz, 1H), 4.03 (t, J=5.8 Hz, 2H), 3. 39-3. 32 (m, 1H), 3.28 (d, J=4.0 Hz, 1H), 2.53 (s, 3H), 2. 36-2. 28 (m, 2H), 2. 09-2. 02 (m, 2H), 1.18 (d, J=7.2 Hz, 3H).

Example 68: Synthesis of [1-[3-[2-methoxy-4-(trifluoromethoxy)phenyl]phenyl]-2-(5-methyl-1,3,4-oxadiazol-2-yl)ethyl] carbamate

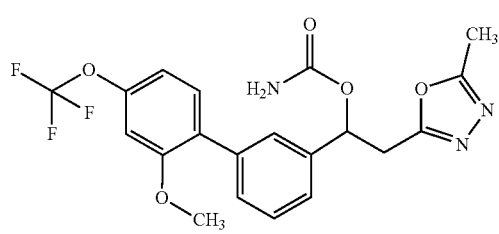 [SMILES: COc1cc(OC(F)(F)F)ccc1-c1cccc(C(Cc2nnc(C)o2)OC(N)=O)c1]

1-[3-(2-Methoxy-4-(trifluoromethoxy)phenyl]phenyl]-2-(5-methyl-1,3,4-oxadiazol-2-yl)ethanol, which is the final compound of Example 60, as a starting material was used in the same manner as in Example 3 to obtain the title compound.

$^1$H-NMR (CDCl$_3$, 400 MHz) δ=7. 48-7. 26 (m, 5H), 6.90 (d, J=8.4 Hz, 1H), 6.82 (s, 1H), 6.12 (dd, J=4.8, 9.2 Hz, 1H), 4.71 (brs, 2H, NH2), 3.81 (s, 3H), 3.48 (dd, J=9.2, 15.2 Hz, 1H), 3.29 (dd, J=4.8, 15.2 Hz, 1H), 2.50 (s, 3H).

Example 69: Synthesis of [1-[3-[4-chloro-2-(trifluoromethyl)phenyl]phenyl]-2-(5-methyl-1,3,4-oxadiazol-2-yl)ethyl] carbamate

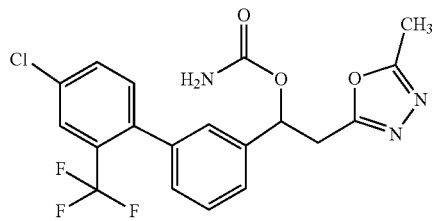 [SMILES: Cc1nnc(CC(OC(N)=O)c2cccc(-c3ccc(Cl)cc3C(F)(F)F)c2)o1]

1-[3-(4-Chloro-2-(trifluoromethyl)phenyl]phenyl]-2-(5-methyl-1,3,4-oxadiazol-2-yl)ethanol, which is the final compound of Example 61, as a starting material was used in the same manner as in Example 3 to obtain the title compound.

$^1$H-NMR (CDCl$_3$, 400 MHz) δ=7.7 (s, 1H), 7.54 (d, J=8.0 Hz, 1H), 7. 41-7. 26 (m, 5H), 6.08 (dd, J=4.8, 8.4 Hz, 1H), 4.86 (brs, 2H, NH2), 3.47 (dd, J=8.4, 15.2 Hz, 1H), 3.29 (dd, J=4.8, 15.2 Hz, 1H), 2.49 (s, 3H).

Example 70: Synthesis of [1-[3-(4-chloro-2-methoxy-phenyl)phenyl]-2-(5-methyl-1,3,4-oxadiazol-2-yl)ethyl] carbamate

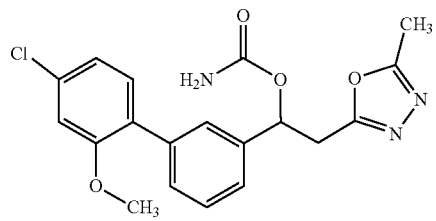 [SMILES: COc1cc(Cl)ccc1-c1cccc(C(Cc2nnc(C)o2)OC(N)=O)c1]

1-[3-(4-Chloro-2-methoxy-phenyl)phenyl]-2-(5-methyl-1,3,4-oxadiazol-2-yl)ethanol, which is the final compound of Example 62, as a starting material was used in the same manner as in Example 3 to obtain the title compound.

$^1$H-NMR (CDCl$_3$, 400 MHz) δ=7. 52-7. 19 (m, 5H), 7.00 (d, J=8.0 Hz, 1H), 6.96 (s, 1H), 6.09 (dd, J=4.4, 9.2 Hz, 1H), 4.86 (brs, 2H, NH2), 3.80 (s, 3H), 3.47 (dd, J=9.2, 15.2 Hz, 1H), 3.29 (dd, J=4.4, 15.2 Hz, 1H), 2.48 (s, 3H).

Example 71: Synthesis of [1-[3-(3, 4-difluorophenyl)phenyl]-2-(5-methyl-1,3,4-oxadiazol-2-yl)ethyl] carbamate

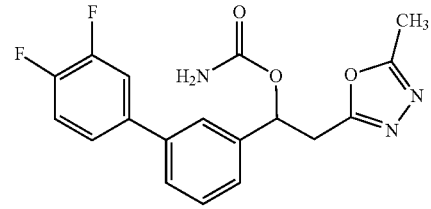 [SMILES: Cc1nnc(CC(OC(N)=O)c2cccc(-c3ccc(F)c(F)c3)c2)o1]

1-[3-(3,4-Difluorophenyl)phenyl]-2-(5-methyl-1, 3, 4-oxadiazole-2-yl)ethanol, which is the final of Example 58, as a starting material was used in the same manner as in Example 3 to obtain the title compound.

¹H-NMR (CDCl₃, 400 MHz) δ=7. 37-7. 51 (m, 6H), 7. 22-7. 34 (m, 1H), 6.13 (dd, J=4.8, 8 Hz, 1H), 4.66 (brs, 1H), 3. 29-3. 53 (m, 2H), 2.50 (s, 3H).

Example 72: Synthesis of [1-[3-(4-fluorophenyl)phenyl]-2-(5-methyl-1,3,4-oxadiazol-2-yl)ethyl] carbamate

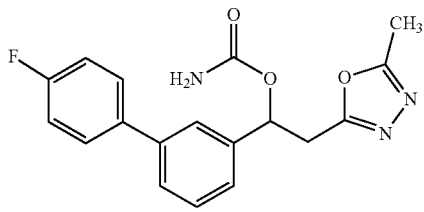 [SMILES: Cc1nnc(CC(OC(N)=O)c2cccc(-c3ccc(F)cc3)c2)o1]

1-[3-(4-Fluorophenyl)phenyl]-2-(5-methyl-1,3,4-oxadiazol-2-yl)ethanol, which is the final compound of Example 57, as a starting material was used in the same manner as in Example 3 to obtain the title compound.

¹H-NMR (CDCl₃, 400 MHz) δ=7. 35-7. 58 (m, 6H), 7. 12-7. 16 (m, 2H), 6.13 (dd, J=5.2, 9.6 Hz, 1H), 4.66 (brs, 1H), 3. 29-3. 53 (m, 2H), 2.50 (s, 3H).

Example 73: Synthesis of [1-[3-(2-chlorophenyl)phenyl]-2-(5-methyl-1,3,4-oxadiazol-2-yl)ethyl] carbamate

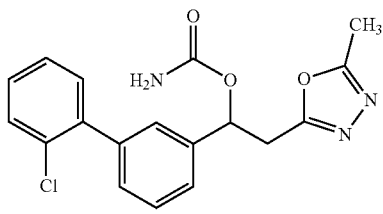 [SMILES: Cc1nnc(CC(OC(N)=O)c2cccc(-c3ccccc3Cl)c2)o1]

1-[3-(2-Chlorophenyl)phenyl]-2-(5-methyl-1, 3, 4-oxadiazole-2-yl)ethanol, which is the final compound of Example 63, as a starting material was used in the same manner as in Example 3 to obtain the title compound.

¹H-NMR (CDCl₃, 400 MHz) δ=7. 52-7. 38 (m, 6H), 7. 32-7. 30 (m, 2H), 6. 15-6. 11 (m, 1H), 4.64 (brs, 2H, NH2), 3.50 (dd, J=11, 19.5, 1H), 3.32 (dd, J=6, 19.5 Hz, 1H), 2.50 (s, 3H).

Example 74: Synthesis of [1-[3-(3-chlorophenyl)phenyl]-2-(5-methyl-1,3,4-oxadiazol-2-yl)ethyl]carbamate

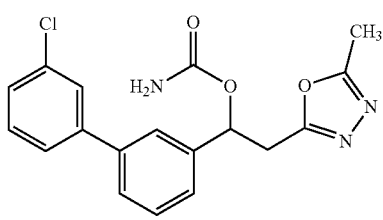 [SMILES: Cc1nnc(CC(OC(N)=O)c2cccc(-c3cccc(Cl)c3)c2)o1]

1-[3-(3-Chlorophenyl)phenyl]-2-(5-methyl-1,3,4-oxadiazol-2-yl)ethanol, which is the final compound of Example 64, as a starting material was used in the same manner as in Example 3 to obtain the title compound.

¹H-NMR (CDCl₃, 400 MHz) δ=7. 54-7. 47 (m, 4H), 7. 45-7. 36 (m, 4H), 6. 15-6. 11 (m, 1H), 4.67 (brs, 2H, NH2), 3.50 (dd, J=11.5, 19 Hz, 1H), 3.32 (dd, J=6, 19 Hz, 1H), 2.50 (s, 3H).

Example 75: Synthesis of [1-[3-(4-chlorophenyl)phenyl]-2-(5-methyl-1,3,4-oxadiazole-2-yl)ethyl] carbamate

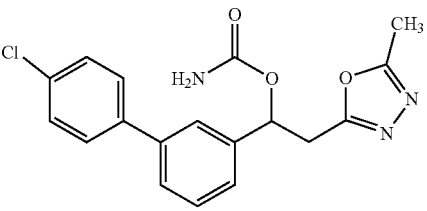 [SMILES: Cc1nnc(CC(OC(N)=O)c2cccc(-c3ccc(Cl)cc3)c2)o1]

1-[3-(4-Chlorophenyl)phenyl]-2-(5-methyl-1,3,4-oxadiazol-2-yl)ethanol, which is the final compound of Example 65, as a starting material was used in the same manner as in Example 3 to obtain the title compound.

¹H-NMR (CDCl₃, 400 MHz) δ=7. 55-7. 52 (m, 3H), 7. 47-7. 40 (m, 2H), 7. 40-7. 26 (m, 3H), 6. 15-6. 12 (m, 1H), 4.67 (brs, 2H, NH2), 3.50 (dd, J=11, 20 Hz, 1H), 3.32 (dd, J=6, 19 Hz, 1H), 2.51 (s, 3H).

Example 76: Synthesis of 1-[3-[2,4-bis(trifluoromethyl)phenyl)phenyl]-2-(5-methyl-1,3,4-oxadiazol-2-yl)ethanol

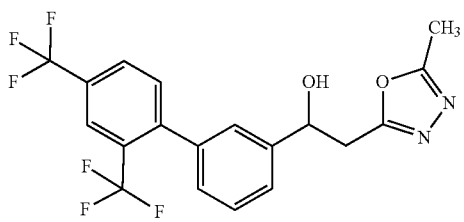 [SMILES: Cc1nnc(CC(O)c2cccc(-c3ccc(C(F)(F)F)cc3C(F)(F)F)c2)o1]

The title compound was synthesized in the same manner as in Example 1, except that 3-bromobenzaldehyde was used as a starting material and 2, 4-bistrifluoromethylphenylboronic acid was used instead of 4-chlorophenylboronic acid in Example 1-2.

¹H-NMR (CDCl₃, 400 MHz) δ=8.01 (s, 1H), 7.84 (d, J=9.5 Hz, 1H), 7. 50-7. 43 (m, 3H), 7.38 (s, 1H), 7. 29-7. 28 (m, 1H), 5. 33-5. 30 (m, 1H), 3. 29-3. 22 (m, 3H), 2.51 (s, 3H).

Example 77: Synthesis of [1-[3-[2,4-bis(trifluoromethyl)phenyl]phenyl]-2-(5-methyl-1,3,4-oxadiazol-2-yl)ethyl] carbamate

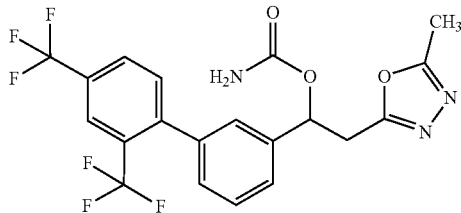 [SMILES: Cc1nnc(CC(OC(N)=O)c2cccc(-c3ccc(C(F)(F)F)cc3C(F)(F)F)c2)o1]

1-[3-[2,4-Bis(trifluoromethyl)phenyl)phenyl]-2-(5-methyl-1,3,4-oxadiazol-2-yl)ethanol, which is the final compound of Example 76, as a starting material was used in the same manner as in Example 3 to obtain the title compound.
¹H-NMR (CDCl₃, 400 MHz) δ=8.01 (s, 1H), 7.84 (d, J=9.5 Hz, 1H), 7. 50-7. 44 (m, 3H), 7.32 (s, 1H), 7. 29-7. 27 (m, 1H), 6. 13-6. 10 (m, 1H), 4.65 (brs, 2H, NH2), 3.48 (dd, J=10.5, 19 Hz, 1H), 3.31 (dd, J=6, 19 Hz, 1H), 2.48 (s, 3H).

Example 78: Synthesis of [1-[3-[4-(trifluoromethoxy)phenyl]phenyl]-2-(5-methyl-1,3,4-oxadiazol-2-yl)ethyl] carbamate

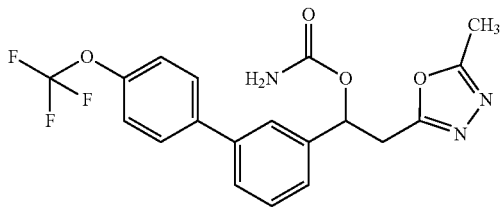 [SMILES: Cc1nnc(CC(OC(N)=O)c2cccc(-c3ccc(OC(F)(F)F)cc3)c2)o1]

2-(5-Methyl-1,3,4-oxadiazol-2-yl)-1-[3-[4-(trifluoromethoxy)phenyl]phenyl]ethanol, which is the final compound of Example 59, as a starting material was used in the same manner as in Example 3 to obtain the title compound.
¹H-NMR (CDCl₃, 400 MHz) δ=7. 51-7. 59 (m, 4H), 7.46 (t, J=7.2 Hz, 1H), 7.38 (d, J=7.2 Hz, 1H), 7.28 (d, J=8.0 Hz, 2H), 6.13 (dd, J=4.4, 8.8 Hz, 1H), 4.66 (brs, 1H), 3. 29-3. 53 (m, 2H), 2.50 (s, 3H).

Example 79: Synthesis of [2-fluoro-2-(5-methyl-1,3,4-oxadiazol-2-yl)-1-[3-(4,4,4-trifluorobutoxy)phenyl]ethyl] carbamate

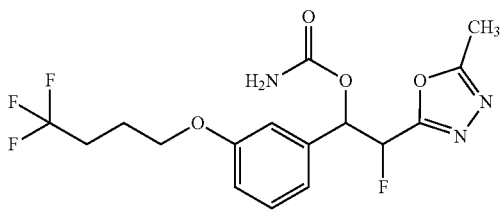 [SMILES: Cc1nnc(C(F)C(OC(N)=O)c2cccc(OCCCC(F)(F)F)c2)o1]

2-Fluoro-2-(5-methyl-1,3,4-oxadiazol-2-yl)-1-[3-(4,4,4-trifluorobutoxy)phenyl]ethanol, which is the final compound of Example 66, as a starting material was used in the same manner as in Example 3 to obtain the title compound.
¹H-NMR (CDCl₃, 400 MHz) δ=7. 33-7. 22 (m, 1H), 7. 02-6. 82 (m, 3H), 6. 24-6. 10 (m, 1H), 5. 90-5. 74 (m, 1H), 4.72 (brs, 2H, NH2), 4. 03-3. 93 (m, 2H), 2. 58-2. 53 (m, 3H), 2. 36-2. 24 (m, 2H), 2. 09-2. 00 (m, 2H).

Example 80: Synthesis of [2-(5-methyl-1,3,4-oxadiazol-2-yl)-1-[3-(4,4,4-trifluorobutoxy)phenyl]propyl] carbamate

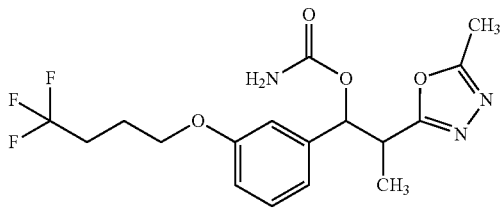 [SMILES: Cc1nnc(C(C)C(OC(N)=O)c2cccc(OCCCC(F)(F)F)c2)o1]

2-(5-Methyl-1,3,4-oxadiazol-2-yl)-1-[3-(4,4,4-trifluorobutoxy)phenyl]propan-1-ol, which is the final compound of Example 67, as a starting material was used in the same manner as in Example 3 to obtain the title compound.
¹H-NMR (CDCl₃, 400 MHz) δ=7.29 (t, J=7.9 Hz, 1H), 6.94 (d, J=7.9 Hz, 1H), 6. 88-6. 84 (m, 2H), 5.74 (d, J=9.4 Hz, 1H), 4.59 (brs, 2H, NH2), 4.01 (t, J=5.9 Hz, 2H), 3. 63-3. 55 (m, 1H), 2.53 (s, 3H), 2. 38-2. 28 (m, 2H), 2. 09-2. 04 (m, 2H), 1.19 (d, J=7.2 Hz, 3H).

Example 81: Synthesis of 2-(3-methyl-1,2,4-oxadiazol-5-yl)-1-[3-[4-(trifluoromethyl)phenyl]phenyl]ethanol

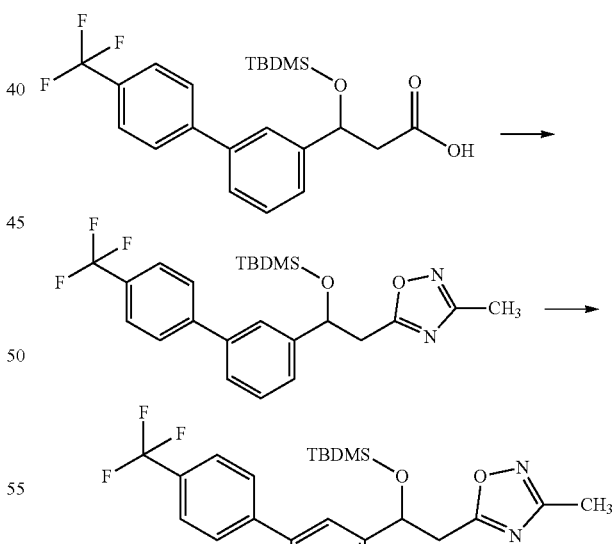

Example 81-1: Synthesis of tert-butyl-dimethyl-[2-(3-methyl-1,2,4-oxadiazol-5-yl)-1-[3-[4-(trifluoromethyl)phenyl]phenyl]ethoxy]silane N-hydroxyacetamidine (74 mg, 1.0 mmol), 1-(3-dimethylaminopropyl)-3-ethylcarbodiimide (186 mg, 1.2 mmol), and triethylamine (0.4 mL, 3.0 mmol) were sequentially added to 20 mL of methylene chloride containing 3-[tert-butyl(dimethyl)silyl]oxy-3-[3-[4-(trifluoromethyl)phenyl]phenyl]propanoic acid (0.4 g, 1.0 mmol) obtained in Example 53-2, and the mixture was stirred at room temperature for 2 hours. 100 mL of ethyl acetate was added to the reaction mixture, and the reaction mixture was sequentially washed with saturated ammonium chloride aqueous solution, saturated sodium bicarbonate aqueous solution, and saturated sodium chloride aqueous solution, and then the organic layer was dried over anhydrous magnesium sulfate. A yellow liquid obtained by removing the solvent by vacuum evaporation was purified by flash chromatography to obtain the title compound in pale yellow.

Example 81-2: Synthesis of 2-(3-methyl-1,2,4-oxadiazol-5-yl)-1-[3-[4-(trifluoromethyl)phenyl]phenyl]ethanol Tetra-N-butylammonium fluoride (16.7 mL, 5.0 mmol) was slowly added to 10 mL of tetrahydrofuran containing tert-butyl-dimethyl-[2-(3-methyl-1, 2, 4-oxadiazole-5-yl)-1-[3-[4-(trifluoromethyl)phenyl]phenyl]ethoxy]silane (1.0 g, 2.48 mmol) obtained in Example 81-1 while maintaining the temperature at 0° C. under ice bath. The reaction mixture was stirred at the same temperature for 1 hour, 20 mL of ethyl acetate was added thereto, washed with saturated aqueous ammonium chloride solution, saturated aqueous sodium bicarbonate solution and saturated aqueous sodium chloride solution, and dried over anhydrous magnesium sulfate. Light brown oil liquid obtained by removing the solvent by evaporation under reduced pressure was purified by flash chromatography to obtain the title compound as white solid.

$^1$H-NMR (CDCl$_3$, 400 MHz) δ=7. 70-7. 68 (m, 4H), 7. 57-7. 55 (m, 1H), 7. 51-7. 45 (m, 3H), 5. 37-5. 33 (m, 1H), 3. 44-3. 34 (m, 3H), 2.43 (s, 3H).

Example 82: Synthesis of [2-(3-methyl-1,2,4-oxadiazol-5-yl)-1-[3-[4-(trifluoromethyl)phenyl]phenyl]ethyl] carbamate

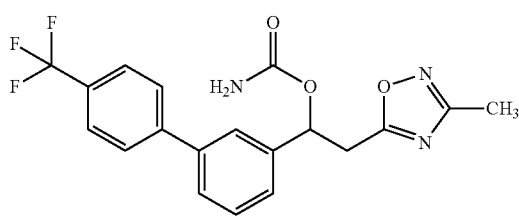 [SMILES: Cc1noc(CC(OC(N)=O)c2cccc(-c3ccc(C(F)(F)F)cc3)c2)n1]

2-(3-Methyl-1,2,4-oxadiazol-5-yl)-1-[3-[4-(trifluoromethyl)phenyl]phenyl]ethanol, which was the final compound of Example 81, as the starting material was used in the same manner as in Example 3 to obtain the title compound.

$^1$H-NMR (CDCl$_3$, 400 MHz) δ=7.67 (dd, J=10.0, 17.5 Hz, 4H), 7. 58-7. 39 (m, 4H), 6.13 (s, 1H), 4.95 (brs, 2H, NH2), 3. 42-3. 39 (m, 2H), 2.39 (s, 3H).

Example 83: Synthesis of 2-(5-methyl-1,2,4-oxadiazol-3-yl)-1-[3-[4-(trifluoromethyl)phenyl]phenyl]ethanol

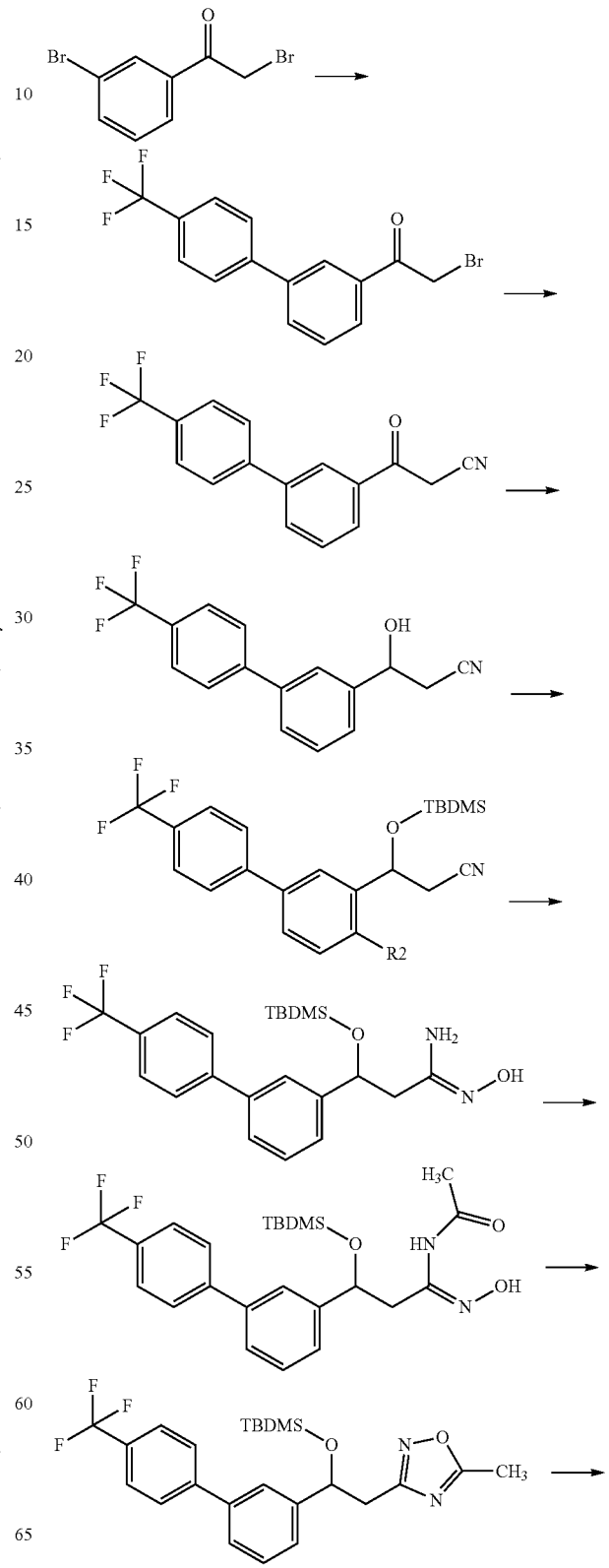

-continued

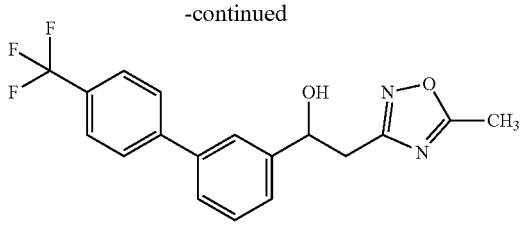

Example 83-1: Synthesis of 2-bromo-1-[3-[4-(trifluoromethyl)phenyl]phenyl]ethanone 4-Chlorophenylboronic acid (0.8 g, 5.1 mmol), Pd(PPh$_3$)$_2$Cl$_2$ (0.2 g, 0.3 mmol) and 3.6 mL of 2M potassium carbonate aqueous solution were sequentially added to 20 mL of 1,4-dioxane containing 2-bromo-1-(3-bromophenyl)ethanone (1.0 g, 3.6 mmol) dissolved therein, and the mixture was stirred at 90° C. for 1 hour. The temperature was lowered to room temperature, 50 mL of ethyl acetate was added to the reaction mixture, and then the mixture was washed with saturated aqueous sodium bicarbonate solution and saturated aqueous sodium chloride solution one time each, and the organic layer was dried over anhydrous magnesium sulfate. The dark brown oil liquid obtained by removing the solvent by evaporation under reduced pressure was purified by flash chromatography to obtain the title compound as yellow solid.

Example 83-2: Synthesis of 1-[3-[4-(trifluoromethyl)phenyl]phenyl]propan-1-one Sodium cyanate (0.2 g, 5.8 mmol) was added to 10 mL of acetonitrile containing 2-bromo-1-[3-[4-(trifluoromethyl)phenyl]phenyl]ethanone (1.0 g, 2.9 mmol), obtained in Example 83-1, and heated and refluxed at 90° C. for about 10 hours. 20 mL of ethyl acetate was added to the reaction mixture, and the mixture was washed with saturated aqueous ammonium chloride solution, saturated aqueous sodium bicarbonate solution, and saturated aqueous sodium chloride solution one time each, and dried over anhydrous magnesium sulfate. Light brown oil liquid obtained by removing the solvent by evaporation under reduced pressure was purified by flash chromatography to obtain the title compound as white solid.

Example 83-3: Synthesis of 1-[3-[4-(trifluoromethyl)phenyl]phenyl]propan-1-ol Sodium borohydride (0.2 g, 7.0 mmol) was slowly added to 20 mL of methanol dissolved with 1-[3-[4-(trifluoromethyl)phenyl]phenyl]propan-1-one (1.3 g, 4.7 mmol) obtained in Example 83-2 while maintaining the temperature at 0° C. under ice bath. The reaction mixture was stirred at the same temperature for 1 hour, 20 mL of ethyl acetate was added thereto, washed with saturated aqueous ammonium chloride solution, saturated aqueous sodium bicarbonate solution and saturated aqueous sodium chloride solution, and dried over anhydrous magnesium sulfate. Light brown oil liquid obtained by removing the solvent by evaporation under reduced pressure was purified by flash chromatography to obtain the title compound as white solid.

Example 83-4: Synthesis of tert-butyl-dimethyl-[1-[2-methyl-5-[4-(trifluoromethyl) phenyl]phenyl]propoxy]silane Imidazole (0.5 g, 7.7 mmol) and tert-butyldimethylsilyl chloride (1.1 g, 7.7 mmol) were sequentially added to 20 mL of methylene chloride dissolved with 1-[3-[4-(trifluoromethyl)phenyl]phenyl]propan-1-ol (1.3 g, 4.6 mmol) obtained in Example 83-3, and the mixture was stirred at room temperature for one day. 100 mL of ethyl acetate was added to the reaction mixture, and the reaction mixture was sequentially washed with saturated ammonium chloride aqueous solution, saturated sodium bicarbonate aqueous solution and saturated sodium chloride aqueous solution, and then the organic layer was dried over anhydrous magnesium sulfate. The yellow oil liquid obtained by removing the solvent by evaporation under reduced pressure was purified by flash chromatography to obtain the title compound as light yellow liquid.

Example 83-5: Synthesis of 3-[tert-butyl(dimethyl)silyl]oxy-N'-hydroxy-3-[3-[4-(trifluoromethyl)phenyl]phenyl]propanamidine Hydroxylamine (66 mg, 2.0 mmol) and potassium carbonate (0.4 g, 3.0 mmol) were added to 20 mL of methanol containing tert-butyl-dimethyl-[1-[2-methyl-5-[4-(trifluoromethyl)phenyl]phenyl]propoxy]silane (0.4 g, 1.0 mmol) obtained in Example 83-4, and heated and refluxed at 70° C. for about 10 hours. 100 mL of ethyl acetate was added to the reaction mixture, and the reaction mixture was sequentially washed with saturated ammonium chloride aqueous solution, saturated sodium bicarbonate aqueous solution and saturated sodium chloride aqueous solution, and then the organic layer was dried over anhydrous magnesium sulfate. A yellow liquid obtained by removing the solvent by vacuum evaporation was purified by flash chromatography to obtain the title compound in pale yellow.

Example 83-6: Synthesis of N—[(Z)-[2-[tert-butyl(dimethyl)silyl]oxy-2-[3-[4-(trifluoromethyl)phenyl]phenyl]ethyl]-N-hydroxy-carbonimidoyl]acetamide Acetyl chloride (0.1 g, 1.9 mmol) and triethylamine (0.7 mL, 4.8 mmol) were slowly added to 10 mL of toluene containing 3-[tert-butyl(dimethyl)silyl]oxy-N'-hydroxy-3-[3-[4-(trifluoromethyl)phenyl]phenyl]propanamidine (700 mg, 1.6 mmol) obtained in Example 83-5 while keeping the temperature at 0° C. under ice bath. The reaction mixture was stirred at the same temperature for 1 hour, 20 mL of ethyl acetate was added thereto, washed with saturated aqueous ammonium chloride solution, saturated aqueous sodium bicarbonate solution and saturated aqueous sodium chloride solution, and dried over anhydrous magnesium sulfate. Light brown oil liquid obtained by removing the solvent by evaporation under reduced pressure was purified by flash chromatography to obtain the title compound as white solid.

Example 83-7: Synthesis of tert-butyl-dimethyl-[2-(5-methyl-1,2,4-oxadiazol-3-yl)-1-[3-[4-(trifluoromethyl)phenyl]phenyl]ethoxy]silane 20 mL of toluene containing N—[(Z)-[2-[tert-butyl(dimethyl)silyl]oxy-2-[3-[4-(trifluoromethyl)phenyl]phenyl]ethyl]-N-hydroxy-carbonimidoyl]acetamide (1.3 g, 2.7 mmol) obtained in Example 83-6 was heated and refluxed at 110° C. for about 1 hour. 100 mL of ethyl acetate was added to the reaction mixture, and the reaction mixture was sequentially washed with saturated ammonium chloride aqueous solution, saturated sodium bicarbonate aqueous solution and sodium chloride aqueous solution, and then the organic layer was dried over anhydrous magnesium sulfate. The yellow oil liquid obtained by removing the solvent by evaporation under reduced pressure was purified by flash chromatography to obtain the title compound as light yellow liquid.

Example 83-8: Synthesis of 2-(5-methyl-1,2,4-oxadiazol-3-yl)-1-[3-[4-(trifluoromethyl) phenyl]phenyl]ethanol Tetra-N-butylammonium fluoride (16.7 mL, 5.0 mmol) was slowly added to 10 mL of tetrahydrofuran containing tert-butyl-dimethyl-[2-(5-methyl-1,2,4-oxadiazol-3-yl)-1-[3-[4-(trifluoromethyl)phenyl]phenyl]ethoxy]silane (1.0 g, 2.48 mmol) obtained in Example 83-7 while maintaining the temperature at 0° C. under ice bath. The reaction mixture was stirred at the same temperature for 1 hour, 20 mL of ethyl acetate was added thereto, washed with saturated aqueous ammonium chloride solution, saturated aqueous sodium bicarbonate solution and saturated aqueous sodium chloride solution, and dried over anhydrous magnesium sulfate. Light brown oil liquid obtained by removing the solvent by evaporation under reduced pressure was purified by flash chromatography to obtain the title compound as white solid.

$^1$H-NMR (CDCl$_3$, 400 MHz) δ=7. 70-7. 68 (m, 4H), 7. 57-7. 55 (m, 1H), 7. 51-7. 45 (m, 3H), 5. 37-5. 33 (m, 1H), 3. 34-3. 24 (m, 3H), 2.63 (s, 3H).

Example 84: Synthesis of [2-(5-methyl-1,2,4-oxadiazol-3-yl)-1-[3-[4-(trifluoromethyl) phenyl]phenyl]ethyl]carbamate

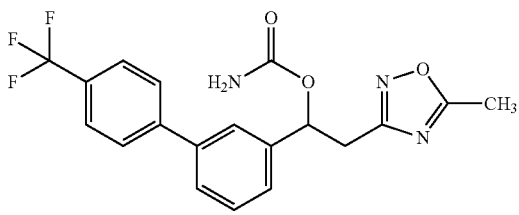 [SMILES: Cc1nc(CC(OC(N)=O)c2cccc(-c3ccc(C(F)(F)F)cc3)c2)no1]

2-(5-Methyl-1,2,4-oxadiazol-3-yl)-1-[3-[4-(trifluoromethyl)phenyl]phenyl]ethanol, which is the final compound of Example 83, as a starting material was used in the same manner as in Example 3 to obtain the title compound.

$^1$H-NMR (CDCl$_3$, 400 MHz) δ=7.67 (dd, J=10.0, 17.5 Hz, 4H), 7. 58-7. 39 (m, 4H), 6.13 (s, 1H), 4.95 (brs, 2H, NH2), 3. 32-3. 29 (m, 2H), 2.59 (s, 3H).

Example 85: Synthesis of (1R)-1-[2-fluoro-5-(4,4,4-trifluorobutoxy)phenyl]-2-(5-methyl-1,3,4-oxadiazol-2-yl)ethanol

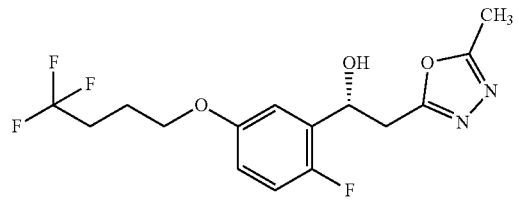 [SMILES: Cc1nnc(C[C@@H](O)c2cc(OCCCC(F)(F)F)ccc2F)o1]

1-[2-Fluoro-5-(4,4,4-trifluorobutoxy)phenyl]-2-(5-methyl-1,3,4-oxadiazol-2-yl)ethanol, which is the final compound of Example 15, as a starting material was used to separate the optical isomer compound by the use of a preparative HPLC device on a ChiralPak OD column (2×20 cm), normal hexane:ethyl acetate=70:30 at a flow rate of 25 mL/min.

$^1$H-NMR (CDCl$_3$, 400 MHz) δ=7. 11-7. 09 (m, 1H), 6.99 (d, J=9.6 Hz, 1H), 6. 79-6. 76 (m, 1H), 5. 51-5. 48 (m, 1H), 4. 01-3. 98 (m, 2H), 3.52 (d, J=4.0 Hz, 1H), 3. 28-3. 12 (m, 2H), 2.52 (s, 3H), 2. 34-2. 27 (m, 2H), 2. 07-2. 02 (m, 2H).

Example 86: Synthesis of (1S)-1-[2-fluoro-5-(4,4,4-trifluorobutoxy)phenyl]-2-(5-methyl-1,3,4-oxadiazol-2-yl)ethanol

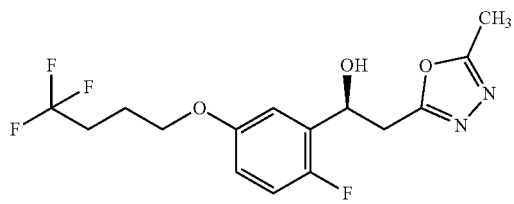 [SMILES: Cc1nnc(C[C@H](O)c2cc(OCCCC(F)(F)F)ccc2F)o1]

1-[2-Fluoro-5-(4,4,4-trifluorobutoxy)phenyl]-2-(5-methyl-1,3,4-oxadiazole-2-yl)ethanol, which is the final compound of Example 15, as a starting material was used to separate the optical isomer compound by the use of a preparative HPLC device on a ChiralPak OD column (2×20 cm), normal hexane:ethyl acetate=70:30 at a flow rate of 25 mL/min.

$^1$H-NMR (CDCl$_3$, 400 MHz) δ=7. 11-7. 09 (m, 1H), 6.99 (d, J=9.6 Hz, 1H), 6. 79-6. 76 (m, 1H), 5. 51-5. 48 (m, 1H), 4. 01-3. 98 (m, 2H), 3.52 (d, J=4.0 Hz, 1H), 3. 28-3. 12 (m, 2H), 2.52 (s, 3H), 2. 34-2. 27 (m, 2H), 2. 07-2. 02 (m, 2H).

Experimental Example

The utility of the compounds according to the present invention as an anticonvulsant agent has been investigated by the 6 Hz method, which has been well established as pharmacological screening methods of convulsant agents for focal onset seizures. The procedure of the 6 Hz method for screening anticonvulsant was as follows:
1) Preparation of Experimental Animals Male ICR mice are purchased from Orient Bio, Inc. of Korea, and are stored and managed according to laboratory animal management standards of the Institutional Animal Care and Use Committee (IACUC) by putting the same in a wire net cage under an environment in which an ambient temperature of 19 to 25° C., 40 to 60% relative humidity and 12 hour periods of light/dark were auto-controlled, and water was freely taken. After stabilization for a week, mice with a body weight of 18 to 23 g were used in the experiment.
2) Evaluation of the Anticonvulsant Effect of a Compound 5% Tetracaine (Sigma) was added to both eyes to provide a local anesthetic effect at 5 to 10 minutes before the period of electrical stimulation at the animal ICR mouse. The compounds to be tested were dissolved in distilled water in which 30% polyethylene glycol 300+5% dimethylsulfoxide+5% Cremophor was dissolved and administered intraperitoneally (ip) to the animal at a dosage volume of 10 mL/kg. Then, electrostimulation of 44 mA, 6 Hz, and 3 sec was applied to the eye to induce focus-generating seizures. After the electrical stimulation, the presence of seizures due to drug effects was confirmed, and the ratio of animals showing no seizures was expressed as a protection rate (the number of non-seizure animals/the number of animals used in experiments=protection rate). Based on a protection rate is "0" when all objects show seizures, and a protection rate is "1" when all objects do not show seizures, the protection rates 0 to 0.2 are scored as '−', 0.2 to 0.6 are scored as '+', 0.6 to 0.8 are scored as '++', and 0.8 to 0.8 are scored as '+++'. The results are represented in Table 2. It is determined that the compound having a high protection rate exhibits a stronger anticonvulsant effect.

TABLE 2

| Compound | 6 Hz, 44 mA protection rate |
| --- | --- |
| Levitiracetam | − |
| Topiramate | − |
| Lamotrigine | − |
| Example 1 | ++ |
| Example 2 | ++ |
| Example 3 | ++ |
| Example 4 | ++ |
| Example 5 | + |
| Example 6 | +++ |
| Example 7 | ++ |
| Example 10 | + |
| Example 11 | + |
| Example 13 | +++ |
| Example 14 | +++ |
| Example 15 | +++ |
| Example 16 | ++ |
| Example 17 | + |
| Example 18 | + |
| Example 19 | + |
| Example 20 | + |
| Example 22 | + |
| Example 23 | + |
| Example 24 | ++ |
| Example 28 | ++ |
| Example 32 | + |
| Example 33 | + |
| Example 34 | ++ |
| Example 37 | + |
| Example 39 | + |
| Example 41 | +++ |
| Example 42 | ++ |
| Example 43 | + |
| Example 48 | ++ |
| Example 49 | +++ |
| Example 50 | ++ |
| Example 51 | + |
| Example 52 | + |
| Example 53 | + |
| Example 55 | + |
| Example 56 | ++ |
| Example 59 | ++ |
| Example 65 | ++ |
| Example 72 | + |
| Example 75 | + |
| Example 78 | ++ |
| Example 85 | +++ |
| Example 86 | +++ |

The invention claimed is:

1. A method for treating epilepsy comprising administering to a subject in need thereof a therapeutically effective amount of Chemical Formula 1, or optical isomer, stereoisomer or pharmaceutically acceptable salt thereof,

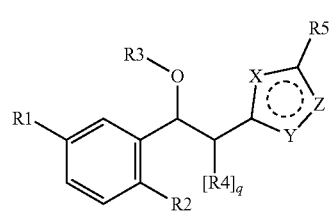

[Chemical Formula 1]

wherein
R1 is selected from the group consisting of the following formulas:

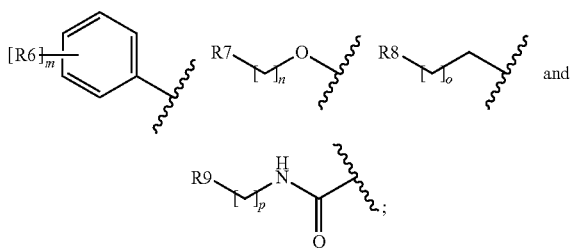

R2 is hydrogen, halo, hydroxy, alkyl, haloalkyl, hydroxyalkyl, alkoxyalkyl, carbamoyloxy, alkoxy, alkylthio, haloalkoxy, or hydroxyalkoxy;
R3 is hydrogen, alkyl, cycloalkyl, haloalkyl, hydroxyalkyl, alkoxyalkyl, carbamoyl, alkylcarbamoyl, dialkylcarbamoyl, carbonyl, or alkylcarbonyl;
R4 is hydrogen, halo, hydroxy, alkyl, haloalkyl, hydroxyalkyl, alkoxyalkyl, carbamoyl, alkylcarbamoyl, or dialkylcarbamoyl;
R5 is hydrogen, halo, hydroxy, alkyl, haloalkyl, hydroxyalkyl, alkoxyalkyl, carbamoyl, alkylcarbamoyl, or dialkylcarbamoyl;
R6, R7, R8 and R9 are each independently hydrogen, halo, alkyl, haloalkyl, hydroxyalkyl, alkoxyalkyl, carbamoyloxyalkyl, alkyl-C(O)O-alkyl, alkoxy, alkylthio, haloalkoxy, hydroxyalkoxy, alkoxy-alkoxy, carbamoyloxyalkoxy, alkyl-C(O)O-alkoxy, amino, dialkylamino, carbonylamino, alkylcarbonylamino, haloalkyl-carbonylamino, or heterocycloalkyl having 1 to 3 nitrogen (N) atoms;
X, Y and Z are each independently selected from the group consisting of nitrogen (N) and oxygen (O), wherein at least one of X, Y or Z is oxygen (O);
m is an integer of 0 to 3;
n, o, and p are each independently an integer of 0 to 5; and
q is an integer of 0 to 2.

2. A pharmaceutical composition comprising a therapeutically effective amount of a compound of Chemical Formula 1 or pharmaceutically acceptable salt thereof, and a pharmaceutically acceptable carrier,

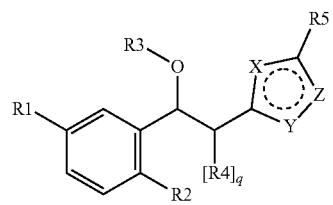

[Chemical Formula 1]

wherein
R1 is selected from the group consisting of the following formulas:

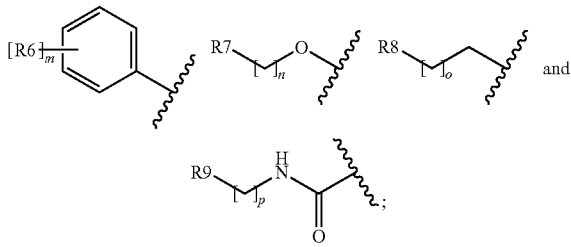

R2 is hydrogen, halo, hydroxy, alkyl, haloalkyl, hydroxyalkyl, alkoxyalkyl, carbamoyloxy, alkoxy, alkylthio, haloalkoxy, or hydroxyalkoxy;
R3 is hydrogen, alkyl, cycloalkyl, haloalkyl, hydroxyalkyl, alkoxyalkyl, carbamoyl, alkylcarbamoyl, dialkylcarbamoyl, carbonyl, or alkylcarbonyl;
R4 is hydrogen, halo, hydroxy, alkyl, haloalkyl, hydroxyalkyl, alkoxyalkyl, carbamoyl, alkylcarbamoyl, or dialkylcarbamoyl;
R5 is hydrogen, halo, hydroxy, alkyl, haloalkyl, hydroxyalkyl, alkoxyalkyl, carbamoyl, alkylcarbamoyl, or dialkylcarbamoyl;
R6, R7, R8 and R9 are each independently hydrogen, halo, alkyl, haloalkyl, hydroxyalkyl, alkoxyalkyl, carbamoyloxyalkyl, alkyl-C(O)O-alkyl, alkoxy, alkylthio, haloalkoxy, hydroxyalkoxy, alkoxy-alkoxy, carbamoyloxyalkyl, alkyl-C(O)O-alkoxy, amino, dialkylamino, carbonylamino, alkylcarbonylamino, haloalkyl-carbonylamino, or heterocycloalkyl having 1 to 3 nitrogen (N) atoms;
X, Y and Z are each independently selected from the group consisting of nitrogen (N) and oxygen (O), wherein at least one of X, Y or Z is oxygen (O);
m is an integer of 0 to 3;
n, o, and p are each independently an integer of 0 to 5; and
q is an integer of 0 to 2.

3. The pharmaceutical composition of claim 2, wherein the pharmaceutically acceptable carrier is a diluent selected from the group consisting of lactose, dextrose, sucrose, mannitol, sorbitol, cellulose, and glycine.

4. The pharmaceutical composition of claim 2, wherein the pharmaceutically acceptable carrier is a lubricant selected from the group consisting of silica, talc, stearic acid, magnesium or calcium salt thereof, and polyethylene glycol.

5. The pharmaceutical composition of claim 2, wherein the pharmaceutically acceptable carrier is a binder selected from the group consisting of magnesium aluminum silicate, starch paste, gelatin, tragacanth, methylcellulose, sodium carboxymethyl cellulose, and polyvinylpyrrolidine.

6. The pharmaceutical composition of claim 2, wherein the pharmaceutically acceptable carrier is a disintegrant selected from the group consisting of starch, agar, alginic acid and a sodium salt thereof.

7. The pharmaceutical composition of claim 2, wherein the pharmaceutically acceptable carrier is an absorbent, a colorant, a flavoring agent, or a sweetening agent.

8. The pharmaceutical composition of claim 2, wherein the pharmaceutical composition is a tablet form.

9. The pharmaceutical composition of claim 2, wherein the pharmaceutical composition is a parenteral dosage form.

10. The pharmaceutical composition of claim 2, wherein the pharmaceutical composition is a solution or a suspension prepared by mixing the compound of Chemical Formula 1 or a pharmaceutically acceptable salt thereof with a stabilizer or a buffer in water.

11. The pharmaceutical composition of claim 10, wherein the solution or the suspension is in a unit dosage form of an ampoule or a vial.

12. The pharmaceutical composition of claim 2, wherein the therapeutically effective amount of the compound of Formula 1 is 0.5 to 100 mg/kg.

13. The pharmaceutical composition of claim 2, wherein R1 is represented by the following formula:

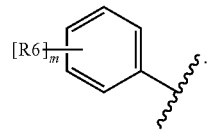

14. The pharmaceutical composition of claim 2, wherein the compound is selected from the group consisting of:
1-[5-(4-chlorophenyl)-2-fluoro-phenyl]-2-(5-methyl-1,3,4-oxadiazol-2-yl)ethanol;
1-[2-fluoro-5-[4-(trifluoromethyl)phenyl]phenyl]-2-(5-methyl-1,3,4-oxadiazol-2-yl)ethanol;
[1-[2-fluoro-5-[4-(trifluoromethyl)phenyl]phenyl]-2-(5-methyl-1,3,4-oxadiazol-2-yl)ethyl]carbamate;
[1-[5-(4-chlorophenyl)-2-fluoro-phenyl]-2-(5-methyl-1,3,4-oxadiazol-2-yl)ethyl]carbamate;
1-[2-fluoro-5-[4-(trifluoromethyl)phenyl]phenyl]-2-(1,3,4-oxadiazol-2-yl)ethanol;
2-(5-methyl-1,3,4-oxadiazol-2-yl)-1-[3-[4-(trifluoromethyl)phenyl]phenyl]ethanol;
[2-(5-methyl-1,3,4-oxadiazol-2-yl)-1-[3-[4-(trifluoromethyl)phenyl]phenyl]ethyl]carbamate;
(1R)-2-(5-methyl-1,3,4-oxadiazol-2-yl)-1-[3-[4-(trifluoromethyl)phenyl]phenyl]ethanol;
(1S)-2-(5-methyl-1,3,4-oxadiazol-2-yl)-1-[3-[4-(trifluoromethyl)phenyl]phenyl]ethanol;
2-(5-methyl-1,3,4-oxadiazol-2-yl)-1-[2-methyl-5-[4-(trifluoromethyl)phenyl]phenyl]ethanol;
1-[2-methoxy-5-[4-(trifluoromethyl)phenyl]phenyl]-2-(5-methyl-1,3,4-oxadiazol-2-yl)ethanol;
[2-(5-methyl-1,3,4-oxadiazol-2-yl)-1-[2-methyl-5-[4-(trifluoromethyl)phenyl]phenyl]ethyl]carbamate;
[1-[2-methoxy-5-[4-(trifluoromethyl)phenyl]phenyl]-2-(5-methyl-1,3,4-oxadiazol-2-yl)ethyl]carbamate;
1-[2-methyl-5-[4-(trifluoromethyl)phenyl]phenyl]-2-(1,3,4-oxadiazol-2-yl)ethanol;
1-[2-methoxy-5-[4-(trifluoromethyl)phenyl]phenyl]-2-(1,3,4-oxadiazol-2-yl)ethanol;
1-[2-chloro-5-[4-(trifluoromethyl)phenyl]phenyl]-2-(5-methyl-1,3,4-oxadiazol-2-yl)ethanol;
1-[2-chloro-5-[4-(trifluoromethyl)phenyl]phenyl]-2-(1,3,4-oxadiazol-2-yl)ethanol;
[1-[2-chloro-5-[4-(trifluoromethyl)phenyl]phenyl]-2-(5-methyl-1,3,4-oxadiazol-2-yl)ethyl]carbamate;
[1-[2-chloro-5-[4-(trifluoromethyl)phenyl]phenyl]-2-(1,3,4-oxadiazol-2-yl)ethyl]carbamate;
2-(1,3,4-oxadiazol-2-yl)-1-[3-[4-(trifluoromethyl)phenyl]phenyl]ethanol;
2-(5-ethyl-1,3,4-oxadiazol-2-yl)-1-[3-[4-(trifluoromethyl)phenyl]phenyl]ethanol;

2-(5-tert-butyl-1,3,4-oxadiazol-2-yl)-1-[3-[4-(trifluoromethyl)phenyl]phenyl]ethanol;
[2-(5-methyl-1,3,4-oxadiazol-2-yl)-1-[3-[4-(trifluoromethyl)phenyl]phenyl]ethyl]acetate;
2-[2-methoxy-2-[3-[4-(trifluoromethyl)phenyl]phenyl]ethyl]-5-methyl-1,3,4-oxadiazole;
1-[3-(4-fluorophenyl)phenyl]-2-(5-methyl-1,3,4-oxadiazol-2-yl)ethanol;
1-[3-(3,4-difluorophenyl)phenyl]-2-(5-methyl-1,3,4-oxadiazole-2-yl)ethanol;
2-(5-methyl-1,3,4-oxadiazol-2-yl)-1-[3-[4-(trifluoromethoxy)phenyl]phenyl]ethanol;
1-[3-(2-methoxy-4-(trifluoromethoxy)phenyl)phenyl]-2-(5-methyl-1,3,4-oxadiazol-2-yl)ethanol;
1-[3-(4-chloro-2-(trifluoromethyl)phenyl)phenyl]-2-(5-methyl-1,3,4-oxadiazol-2-yl)ethanol;
1-[3-(4-chloro-2-methoxy-phenyl)phenyl]-2-(5-methyl-1,3,4-oxadiazol-2-yl)ethanol;
1-[3-(2-chlorophenyl)phenyl]-2-(5-methyl-1,3,4-oxadiazol-2-yl)ethanol;
1-[3-(3-chlorophenyl)phenyl]-2-(5-methyl-1,3,4-oxadiazol-2-yl)ethanol;
1-[3-(4-chlorophenyl)phenyl]-2-(5-methyl-1,3,4-oxadiazol-2-yl)ethanol;
[1-[3-[2-methoxy-4-(trifluoromethoxy)phenyl]phenyl]-2-(5-methyl-1,3,4-oxadiazol-2-yl)ethyl]carbamate;
[1-[3-[4-chloro-2-(trifluoromethyl)phenyl]phenyl]-2-(5-methyl-1,3,4-oxadiazol-2-yl)ethyl]carbamate;
[1-[3-(4-chloro-2-methoxy-phenyl)phenyl]-2-(5-methyl-1,3,4-oxadiazol-2-yl)ethyl]carbamate;
[1-[3-(3,4-difluorophenyl)phenyl]-2-(5-methyl-1,3,4-oxadiazol-2-yl)ethyl]carbamate;
[1-[3-(4-fluorophenyl)phenyl]-2-(5-methyl-1,3,4-oxadiazol-2-yl)ethyl]carbamate;
[1-[3-(2-chlorophenyl)phenyl]-2-(5-methyl-1,3,4-oxadiazol-2-yl)ethyl]carbamate;
[1-[3-(3-chlorophenyl)phenyl]-2-(5-methyl-1,3,4-oxadiazol-2-yl)ethyl]carbamate;
[1-[3-(4-chlorophenyl)phenyl]-2-(5-methyl-1,3,4-oxadiazol-2-yl)ethyl]carbamate;
1-[3-[2,4-bis(trifluoromethyl)phenyl)phenyl]-2-(5-methyl-1,3,4-oxadiazol-2-yl)ethanol;
[1-[3-[2,4-bis(trifluoromethyl)phenyl]phenyl]-2-(5-methyl-1,3,4-oxadiazol-2-yl)ethyl]carbamate;
[1-[3-[4-(trifluoromethoxy)phenyl]phenyl]-2-(5-methyl-1,3,4-oxadiazol-2-yl)ethyl]carbamate;
2-(3-methyl-1,2,4-oxadiazol-5-yl)-1-[3-[4-(trifluoromethyl)phenyl]phenyl]ethanol;
[2-(3-methyl-1,2,4-oxadiazol-5-yl)-1-[3-[4-(trifluoromethyl)phenyl]phenyl]ethyl]carbamate;
2-(5-methyl-1,2,4-oxadiazol-3-yl)-1-[3-[4-(trifluoromethyl)phenyl]phenyl]ethanol; and
[2-(5-methyl-1,2,4-oxadiazol-3-yl)-1-[3-[4-(trifluoromethyl)phenyl]phenyl]ethyl]carbamate.

15. The pharmaceutical composition of claim 2, wherein the compound is selected from the group consisting of:
2-(5-methyl-1,3,4-oxadiazol-2-yl)-1-[3-(2,2,3,3-tetrafluoropropoxy)phenyl]ethanol;
[2-(5-methyl-1,3,4-oxadiazol-2-yl)-1-[3-(2,2,3,3-tetrafluoropropoxy)phenyl]ethyl]carbamate;
1-[2-fluoro-5-(4,4,4-trifluorobutoxy)phenyl]-2-(5-methyl-1,3,4-oxadiazol-2-yl)ethanol;
[1-[2-fluoro-5-(4,4,4-trifluorobutoxy)phenyl]-2-(5-methyl-1,3,4-oxadiazol-2-yl)ethyl]carbamate;
1-[2-fluoro-5-(2,2,2-trifluoroethoxy)phenyl]-2-(5-methyl-1,3,4-oxadiazol-2-yl)ethanol;
[1-[2-fluoro-5-(2,2,2-trifluoroethoxy)phenyl]-2-(5-methyl-1,3,4-oxadiazol-2-yl)ethyl carbamate;
2-(5-methyl-1,3,4-oxadiazol-2-yl)-1-[3-(4,4,4-trifluorobutoxy)phenyl]ethanol;
[2-(5-methyl-1,3,4-oxadiazol-2-yl)-1-[3-(4,4,4-trifluorobutoxy)phenyl]ethyl]carbamate;
1-(5-butoxy-2-fluoro-phenyl)-2-(5-methyl-1,3,4-oxadiazol-2-yl)ethanol;
[1-(5-butoxy-2-fluoro-phenyl)-2-(5-methyl-1,3,4-oxadiazol-2-yl)ethyl]carbamate;
1-[2-fluoro-5-(4,4,4-trifluorobutoxy)phenyl]-2-(1,3,4-oxadiazol-2-yl)ethanol;
[1-[2-fluoro-5-(4,4,4-trifluorobutoxy)phenyl]-2-(1,3,4-oxadiazol-2-yl)ethyl]carbamate;
1-[2-fluoro-5-[3-(1-piperidyl)propoxy]phenyl]-2-(5-methyl-1,3,4-oxadiazol-2-yl)ethanol;
1-[5-[3-(dimethylamino)propoxy]-2-fluoro-phenyl]-2-(5-methyl-1,3,4-oxadiazol-2-yl)ethanol;
1-[2-chloro-5-(4,4,4-trifluorobutoxy)phenyl]-2-(5-methyl-1,3,4-oxadiazol-2-yl)ethanol;
[1-[5-[3-(dimethylamino)propoxy]-2-taluo-phenyl]-2-(5-methyl-1,3,4-oxadiazol-2-yl)ethyl]carbamate;
[1-[2-chloro-5-(4,4,4-trifluorobutoxy)phenyl]-2-(5-methyl-1,3,4-oxadiazol-2-yl)ethyl]carbamate;
2-fluoro-2-(5-methyl-1,3,4-oxadiazol-2-yl)-1-[3-(4,4,4-trifluorobutoxy)phenyl]ethanol;
2-(5-methyl-1,3,4-oxadiazol-2-yl)-1-[3-(4,4,4-trifluorobutoxy)phenyl]propane-1-ol;
[2-fluoro-2-(5-methyl-1,3,4-oxadiazol-2-yl)-1-[3-(4,4,4-trifluorobutoxy)phenyl]ethyl]carbamate;
[2-(5-methyl-1,3,4-oxadiazol-2-yl)-1-[3-(4,4,4-trifluorobutoxy)phenyl]propyl]carbamate;
(1R)-1-[2-fluoro-5-(4,4,4-trifluorobutoxy)phenyl]-2-(5-methyl-1,3,4-oxadiazol-2-yl)ethanol; and
(1S)-1-[2-fluoro-5-(4,4,4-trifluorobutoxy)phenyl]-2-(5-methyl-1,3,4-oxadiazol-2-yl)ethanol.

16. The pharmaceutical composition of claim 2, wherein the compound is selected from the group consisting of:
1-[2-fluoro-5-(3,3,3-trifluoropropyl)phenyl]-2-(5-methyl-1,3,4-oxadiazol-2-yl)ethanol;
[1-[2-fluoro-5-(3,3,3-trifluoropropyl)phenyl]-2-(5-methyl-1,3,4-oxadiazol-2-yl)ethyl]carbamate;
1-[2-fluoro-5-(3,3,3-trifluoropropyl)phenyl]-2-(1,3,4-oxadiazol-2-yl)ethanol;
1-(2-fluoro-5-propyl-phenyl)-2-(5-methyl-1,3,4-oxadiazol-2-yl)ethanol;
1-(2-fluoro-5-pentyl-phenyl)-2-(5-methyl-1,3,4-oxadiazol-2-yl)ethanol;
[1-(2-fluoro-5-propyl-phenyl)-2-(5-methyl-1,3,4-oxadiazol-2-yl)ethyl]carbamate;
[1-(2-fluoro-5-pentyl-phenyl)-2-(5-methyl-1,3,4-oxadiazol-2-yl)ethyl]carbamate;
1-[2-fluoro-5-(4,4,4-trifluorobutyl)phenyl]-2-(1,3,4-oxadiazol-2-yl)ethanol;
1-[2-fluoro-5-(5,5,5-trifluoropentyl)phenyl]-2-(1,3,4-oxadiazol-2-yl)ethanol;
1-[2-fluoro-5-(4,4,4-trifluorobutyl)-phenyl]-2-(5-methyl-1,3,4-oxadiazol-2-yl)ethanol;
1-[2-fluoro-5-(5,5,5-trifluoropentyl)-phenyl]-2-(5-methyl-1,3,4-oxadiazol-2-yl)ethanol;
[1-[2-fluoro-5-(4,4,4-trifluorobutyl)-phenyl]-2-(5-methyl-1,3,4-oxadiazol-2-yl)ethyl] carbamate; and
[1-[2-fluoro-5-(5,5,5-trifluoropentyl)phenyl]-2-(5-methyl-1,3,4-oxadiazol-2-yl)ethyl]carbamate.

17. The pharmaceutical composition of claim 2, wherein the compound is selected from the group consisting of:

4-fluoro-3-[1-hydroxy-2-(5-methyl-1,3,4-oxadiazol-2-yl)ethyl]-N-(3,3,3-trifluoropropyl)benzamide; and

[1-[2-fluoro-5-(3,3,3-trifluoropropylcarbamoyl)phenyl]-2-(5-methyl-1,3,4-oxadiazol-2-yl)ethyl]carbamate.

* * * * *